(12) United States Patent
Zhou et al.

(10) Patent No.: US 12,240,860 B2
(45) Date of Patent: *Mar. 4, 2025

(54) HETEROBICYCLIC CARBOXYLIC ACIDS AND SALTS THEREOF

(71) Applicants: SHENZHEN IONOVA LIFE SCIENCE CO., LTD., Shenzhen (CN); FOSHAN IONOVA BIOTHERAPEUTICS CO., INC., Foshan (CN)

(72) Inventors: Gang Zhou, Bridgewater, NJ (US); Yongkui Sun, Shenzhen (CN); Zhaoyin Wang, Richmond (CA)

(73) Assignee: FOSHAN IONOVA BIOTHERAPEUTICS CO., INC., Foshan (CN)

( * ) Notice: Subject to any disclaimer, the term of this patent is extended or adjusted under 35 U.S.C. 154(b) by 997 days.

This patent is subject to a terminal disclaimer.

(21) Appl. No.: 16/975,134

(22) PCT Filed: Mar. 4, 2019

(86) PCT No.: PCT/CN2019/076882
§ 371 (c)(1),
(2) Date: Aug. 23, 2020

(87) PCT Pub. No.: WO2019/166022
PCT Pub. Date: Sep. 6, 2019

(65) Prior Publication Data
US 2021/0079013 A1    Mar. 18, 2021

(30) Foreign Application Priority Data

Mar. 2, 2018 (WO) ................ PCT/CN2018/077875

(51) Int. Cl.
*C07D 495/04* (2006.01)
*A61K 31/407* (2006.01)
*A61K 45/06* (2006.01)

(52) U.S. Cl.
CPC .......... *C07D 495/04* (2013.01); *A61K 31/407* (2013.01); *A61K 45/06* (2013.01)

(58) Field of Classification Search
CPC .................................................. C07D 495/04
See application file for complete search history.

(56) References Cited

U.S. PATENT DOCUMENTS 3,703,544 A * 11/1972 Morozowich ......... C07C 405/00
562/503
8,404,736 B2 * 3/2013 Yuan ...................... A61P 25/16
548/452

FOREIGN PATENT DOCUMENTS

| CN | 102149384 A | 8/2011 |
|---|---|---|
| CN | 111727044 A | 9/2020 |
| JP | 2009539886 A | 11/2009 |
| JP | 2010519260 A | 6/2010 |
| JP | 2012500211 A | 1/2012 |
| KR | 10-2020-0118037 A | 10/2020 |
| WO | 2007121578 A1 | 11/2007 |
| WO | 2007143825 A1 | 12/2007 |
| WO | 2008052898 A1 | 5/2008 |
| WO | 2009139373 A1 | 11/2009 |
| WO | 2010019796 A1 | 2/2010 |
| WO | 2010121382 A1 | 10/2010 |
| WO | 2017066633 A1 | 4/2017 |
| WO | 2019149286 A1 | 8/2019 |

OTHER PUBLICATIONS

Korn et al, Compound selection for development—is salt formation the ultimate answer? Experiences with an extended concept of the "100 mg approach", 2013, European Journal of Pharmaceutical Sciences, vol. 57, p. 257-263. (Year: 2013).*
"Polymorphic Drugs", Lu Yang et al., People's Medical Publishing House, 1st Edition, Oct. 2009, pp. 5-13.
Gould, Philip L., Salt selection for basic drugs, International Journal of Pharmaceutics, 1986, vol. 33, pp. 201-217.
C. G. Wermuth ed., Latest Medicinal Chemistry, vol. 2, Technomic Co., Ltd., 1999.
Journal of Pharmaceutical Sciences, 1977, vol. 66, No. 1, p. 1-19.

(Continued)

*Primary Examiner* — Kamal A Saeed
*Assistant Examiner* — Karen Cheng
(74) *Attorney, Agent, or Firm* — Weisun Rao; Lili Huang; Venture Partner, LLC

(57) ABSTRACT

The present invention provides pharmaceutically acceptable salts of compounds of Formula I that are potent EP4 receptor antagonists and can be used for treating cancer or inflammatory diseases alone or in combination with antibody therapy, radiation therapy, anti-metabolite chemotherapy to a subject in need thereof.

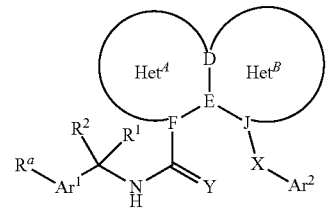

5 Claims, 2 Drawing Sheets

(56) References Cited

OTHER PUBLICATIONS

Boyd Michael J et al: A novel series of potent and selective EP4receptor ligands: Facile modulation of agonism and antagonism11 , Bioorganic & Medicinal Chemistry Letters, vol. 21, No. 1, Oct. 28, 2010 (Oct. 28, 2010), pp. 484-487, XP029121223,ISSN: 0960-894X, DOI:10.1016/J.BMCL.2010.10.106.
Colucci John et al: Discovery of 4-{1-[({1-[4-(trifluoromethyl)benzyl]-IH-i ndol-7-yl}carbonyl)amino]cyclopropyl} benzo ic acid (MF-766), a highly potent and selective EP4antagonist for treating inflammatory pain11 , Bioorganic & Medicinal Chemistry Letters, vol. 20, No. 12, Apr. 18, 2010 (Apr. 18, 2010), pp. 3760-3763, XP029212954, ISSN: 0960-894X, DOI: 10.1016/J.BMCL.2010.04.065.

\* cited by examiner

HETEROBICYCLIC CARBOXYLIC ACIDS AND SALTS THEREOF

CROSS-REFERENCE TO RELATED APPLICATION

This application is the United States national phase of PCT/CN2019/076882, filed on Mar. 2, 2019, which claims priority of PCT application number PCT/CN2018/077875, filed on Mar. 2, 2018, the contents of both of which are incorporated herein by reference in their entirety.

BACKGROUND OF THE INVENTION

Prostaglandins are mediators of pain, fever and other symptoms associated with inflammation. Especially prostaglandin $E_2$ ($PGE_2$) is the predominant eicosanoid detected in inflammation conditions. In addition, it is also involved in various physiological and/or pathological conditions and such as hyperalgesia, uterine contraction, digestive peristalsis, awakeness, suppression of gastric acid secretion, blood pressure, platelet function, bone metabolism, angiogenesis or the like. Four $PGE_2$ receptor subtypes ($EP_1$, $EP_2$, $EP_3$ and $EP_4$) displaying different pharmacological properties have been cloned. $EP_4$ subtype, a Gs-coupled receptor, stimulates cAMP production and is distributed in a wide variety of tissue suggesting major role in $PGE_2$-mediated biological events. Patent application publications WO 96/06822, WO 96/11902, EP 752421-A1, WO03/16254, WO05/021508, and WO 07/121578 disclose compounds as being useful in the treatment of prostaglandin mediated diseases. Three review articles describe the characterization and therapeutic relevance of the prostanoid receptors as well as the most commonly used selective agonists and antagonists: *Eicosanoids: From Biotechnology to Therapeutic Applications*, Folco, Samuelsson, Maclouf, and Velo eds, Plenum Press, New York, 1996, chap. 14, 137-154; *Journal of Lipid Mediators and Cell Signaling*, 1996, 14, 83-87; and Prostaglandins and Other Lipid Mediators, 2002, 69, 557-573.

PGE2 favors a pro-inflammatory immune response; however, PGE2 has been implicated as an important constituent in the immunosuppressive environment created by many solid tumors (Whiteside, Expert Opinion in Biological Therapy, 2010. 10, 1019-1035), sustained levels in tumor microenvironment promote the accumulation and enhance the activity of multiple immunosuppressor cells, including tumor associated macrophages (TAM), Treg cells, and myeloid-derived suppressor cells (MDSCs), and consequently promote tumor immune escape. Accumulating evidence has demonstrated that elevated cAMP levels through EP4 are the primary signal leading to immunosuppression in immune cells (Yokoyama U et al., Pharmacol. Rev., 2013, 65:1010-1052). Studies have also shown that antagonists of prostaglandin E receptor 4 (EP4) can effectively induce inflammation (Chen et al., British J Pharmacol., 2010, 160, 292-310) by blocking of prostaglandin E2 (PGE2) signaling through the interaction of PGE2 with prostaglandin E receptor 4 subtype. Knockout of EP4 in mice showed delayed tumorigenesis compared to wild-type animals in the background of APCmin mutation, indicating a tumor-promoting activity of PGE2-EP4 signaling in host immune cells (Mutoh M et al., Cancer Res., 2002, 62:28-32). Consistently, selective EP4 receptor antagonists have been shown to slow tumor progression and tumor metastasis in various preclinical tumor models without affecting the cancer cell proliferation in vitro (Yang et al., Cancer Res., 2006, 66:9665-9672; Mao Y et al., Clin. Cancer Res., 2014, 20:4096-4106).

Based on such research, antagonists of the EP4 subtype of PGE2 receptors would therefore have therapeutic value in the treatment of diseases or conditions mediated by the EP4 receptor, such as cancer and inflammatory diseases or conditions (e.g., acute and chronic pain, osteoarthritis, rheumatoid arthritis).

BRIEF SUMMARY OF THE INVENTION

The invention in general relates to pharmaceutically acceptable salts or prodrugs that are effective EP4 receptor antagonists and can be used for treating inflammatory diseases, neoplasia and cancer, as well as pharmaceutical compositions containing such salts.

By way of example and without being limiting, the compounds described herein may be used for cancer immune therapy targeting host immunosuppressive cells in the tumor microenvironment that can be of either myeloid or lymphoid lineage. In an embodiment, the compounds described herein may be used to treat patients with a variety of tumor types, including those that harbor high levels of myeloid infiltrate. Such levels of myeloid infiltrate may be identified, for example, based on the Cancer Genome Atlas (TCGA) and other sources. Such tumor types may also be identified based on protein or genetic (e.g., mRNA) expression analysis.

Tumor types may include but are not limited to pancreatic adenocarcinoma, renal Clear cell carcinoma, squamous cell carcinoma of head and neck (SCCHN), non-small cell lung cancer (NSCLC), colorectal cancer (CRC), hepatocellular carcinoma (HCC), serous epithelial ovarian cancer, cervical cancer, transitional cell bladder cancer, and triple-negative breast cancer (TNBC).

In one particular aspect, the invention provides pharmaceutically acceptable salts or prodrugs of compounds of Formula (I):

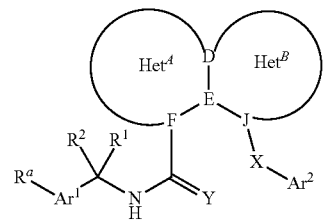

Formula I wherein:

$R^1$ and $R^2$ are independently selected from the group consisting of hydrogen, $C_{1-6}$alkyl, $C_{1-6}$cyclolkyl, $C_{1-6}$fluorocycloalkyl, $C_{1-6}$fluoroalkyl; or, $R^1$ and $R^2$, together with the carbon atom to which they are both attached, complete a three- to six-membered carbocyclic ring which is optionally substituted with $R^c$; or, $R^1$ and $R^2$, together with the carbon atom to which they are both attached, complete a three- to six-membered ring which contains one or two heteroatom(s) such as S, O or $NR^b$, wherein $R^b$ is selected from the group consisting of hydrogen, $C_{1-6}$alkyl, $C_{1-6}$cyclolkyl, $C_{1-6}$fluorocycloalkyl, $C_{1-6}$fluoroalkyl, aryl, heteroaryl, $C(O)C_{1-6}$alkyl, C(O)aryl, $S(O)_2$alkyl, $S(O)_2$aryl;

Y is O or S;

X is a bond, =CH—, CH2, O, or S;

$Ar^1$ and $Ar^2$ are independently selected from the group consisting of $C_{3-6}$cycloalkyl, aryl, heteroaryl and heterocyclyl, or a fused analog of $C_{3-6}$cycloalkyl, aryl, heteroaryl and heterocyclyl, wherein $Ar^1$ and $Ar^2$ are optionally substituted with one to three $R^c$ groups;

$R^c$ is independently selected from halo or $R^1$;

$R^a$ represents —$CO_2H$, —$CO_2M$, —$C(O)NHS(O)_2R^{aa}$, or

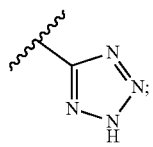

$R^{aa}$ is selected from $C_{1-6}$ alkyl, $C_{1-6}$ haloalkyl, $C_{1-6}$ cycloalkyl, $C_{1-6}$cyclohaloalkyl, aryl and heteroaryl;

M is an ester prodrug group; and

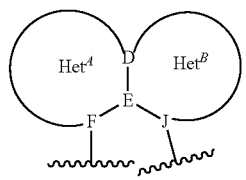

is a 6,6- 5,5- 5,6- or 6,5-bicyclic template.

A basic compound of Formula I possesses one or more functional groups sufficiently basic to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like.

The invention also encompasses other acceptable forms of prodrugs of Formula I formed in a conventional manner with a functional group of the compound such as with an amino, hydroxy, or carboxy group.

In one embodiment,

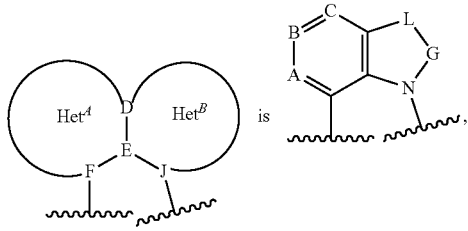

wherein each of A, B and C is independently selected from N, CH and $C(R^c)$; G is selected from —C(O)—, —C(S)—, or —$S(O)_2$—; and L is selected from —$CH_2$—, S, O and NRc.

In another embodiment,

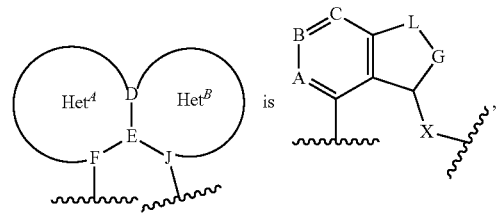

wherein each of A, B and C is independently selected from N, CH and $C(R^c)$; X, L and G are independently selected from a bond, —$CH_2$—, O, S, or $N(R^d)$; and $R^d$ is H, aryl or alkyl.

In another embodiment,

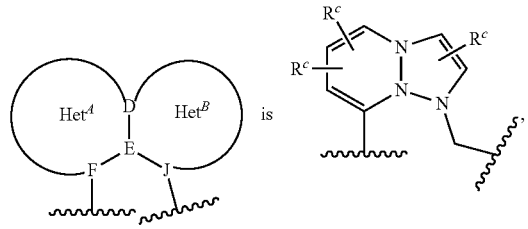

is wherein $R^c$ is as previously defined.

In another embodiment,

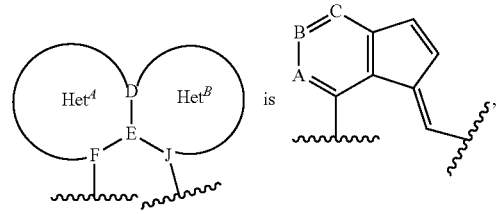

wherein each of A, B and C is independently selected from N, CH and $C(R^c)$.

In another embodiment,

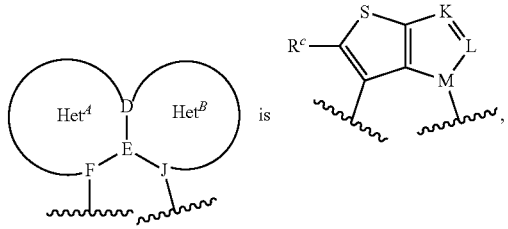

is wherein -K-L-M- is selected from the group consisting of: —C(R$^3$)=C(R$^4$)—N—, —C(R$^4$)=N—C(R$^4$)—, —C(R$^4$)=N—N—, —N=C(R$^4$)—N—, —N=N—N—, —C(R$^4$)$_2$—N=CR$^3$—, —N(R$^4$)—C(R$^4$)=CR$^3$—, —N(R$^4$)—N=CR$^3$—, —N=CR$^3$— and —S—N=CR$^3$—, wherein R$^3$ is selected from the group consisting of hydrogen, halo, C$_{1-6}$alkyl, C$_{1-6}$fluoroalkyl, C$_{1-6}$alkoxy, C$_{1-6}$ fluoroalkoxy and acetyl; each R$^4$ is independently selected from the group consisting of hydrogen, C$_{1-6}$alkyl, C$_{1-6}$fluoroalkyl, C$_{1-6}$alkoxy, C$_{1-4}$ fluoroalkoxy and acetyl.

In another embodiment,

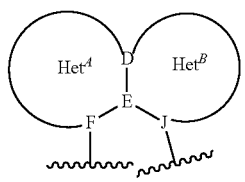

is selected from the following 6,5-hetero-bicyclic moieties:

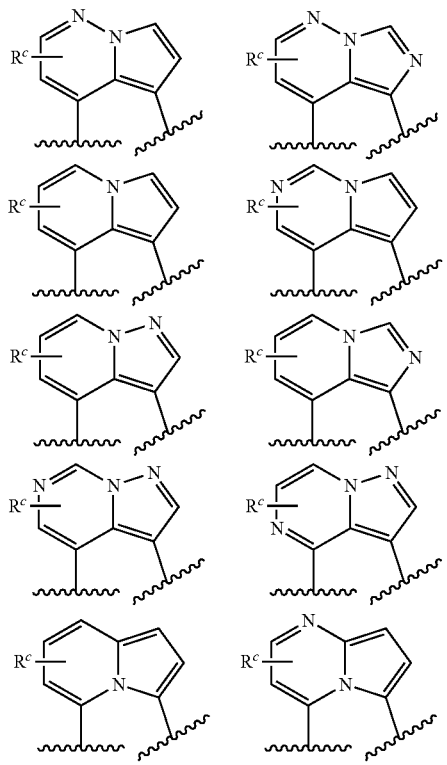

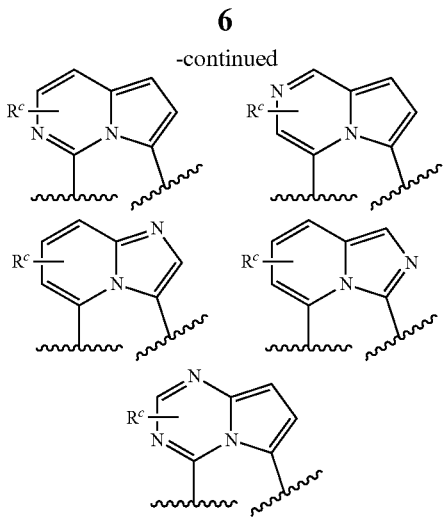

In one embodiment, the present invention relates to compounds of Formula I wherein R$^1$ is methyl and R$^2$ is hydrogen; or wherein R$^1$ is methyl and R$^2$ is methyl; or wherein R$^1$ and R$^2$, together with the carbon atom to which they both are attached, form a three- to six-membered carbocyclic ring.

In another embodiment, the present invention relates to compounds of Formula I wherein Ar$^1$ is phenyl, optionally substituted with one to three R$^c$ groups; or compounds of Formula I wherein Ar$^2$ is phenyl, optionally substituted with one to three R$^c$ groups.

The present invention also encompasses a prodrug of a compound of Formula I. The prodrug can be an ester or amide or other suitable group. Preferred prodrugs include ester derivatives of Formula Ia.

Formula Ia

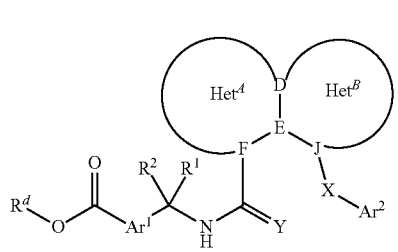

wherein R$^d$ represents an alkyl group having 1 to 10 carbon atoms or an arylalkyl group having from 7 to 12 carbon atoms, aryl, or heteroaryl.

Examples of nitric oxide-releasing prodrugs of EP4 antagonists include those of Formula Ic or a pharmaceutically acceptable salt thereof:

Formula Ic

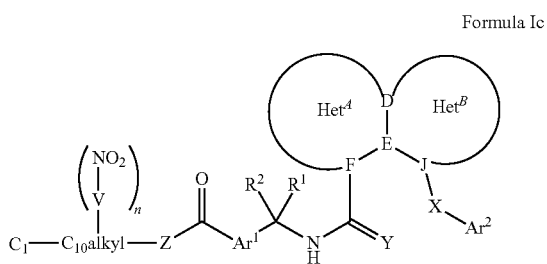

wherein

Z is O, S or $NR^e$; $R^e$ is hydrogen, alkyl or aryl;

each V is independently selected from the group consisting of O and S, and each V is independently attached to any one carbon atom of the $C_{1-10}$alkyl;

n is 1, 2, 3 or 4.

Another embodiment of compounds of nitric oxide-releasing prodrugs of EP4 antagonists are those of Formula Id, Formula Id

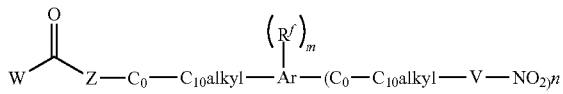

wherein

Z is O, S or $NR^e$; $R^e$ is hydrogen, alkyl or aryl;

V is O or S; each V is independently attached to one carbon atom of $C_{1-6}$alkyl;

$R^f$ is selected from the group consisting of hydrogen, halo, alkoxy, alkylthio, CN, $CF_3$, alkyl, alkylsulfonyl, $S(O)_2NH_2$, and $S(O)_2NH$-alkyl; and W is

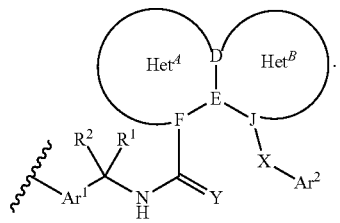

The pharmaceutically acceptable salts of the present invention are useful for treating or preventing a neoplasia in a subject in need of such treatment or prevention. The treatment includes partial or total inhibition of the neoplasia growth, spreading or metastasis, as well as partial or total destruction of the neoplastic cells. The term "prevention" includes either preventing the onset of clinically evident neoplasia altogether or preventing the onset of a preclinically evident stage of neoplasia in individuals at risk. Also intended to be encompassed by this definition is the prevention of initiation for malignant cells or to arrest or reverse the progression of premalignant cells to malignant cells. This includes prophylactic treatment of those at risk of developing the neoplasia. The term "subject" for purposes of treatment includes any human or mammal subject who has any one of the known neoplasia, and preferably is a human subject. For methods of prevention, the subject is any human or animal subject, and preferably is a human subject who is at risk for obtaining a neoplasia. The subject may be at risk due to exposure to carcinogenic agents, being genetically predisposed to have the neoplasia, and the like.

The anti-tumor activities of various combinations of an EP4 antagonist with: radiation; antibodies to cytotoxic t-lymphocyte antigen 4 (anti-CTLA4); antibodies to programmed death ligand 1 (anti-PDL1); antibodies to programmed cell death protein 1 (anti-PD1); and antimetabolites have been examined. The results from this examination have indicated improved and/or synergistic anti-tumor activities by the combination of the EP4 antagonist with the other therapies as compared to single agent treatment alone, and in some embodiments this may result in a memory immune response against the tumor, even as against a different cancer. Thus, in one aspect of the invention, provided is a method of treating cancer in a subject in need thereof comprising administering an EP4 antagonist in combination with a therapy selected from the group consisting of radiation therapy, antibody therapy and anti-metabolite chemotherapy. In a more particular aspect of the invention, the antibody therapy is selected from the group consisting of CTLA4 antibody therapy, PDL1 antibody therapy, and PD1 antibody therapy. In some embodiments, the cancer is metastatic cancer. In another aspect of the invention, provided is a method of generating a memory immune response in a subject in need thereof comprising administering an amount of an EP4 antagonist in combination with a therapy selected from the group consisting of radiation therapy, antibody therapy and anti-metabolite chemotherapy. In another more particular aspect of the invention, the antibody therapy is selected from the group consisting of CTLA4 antibody therapy, PDL1 antibody therapy and PD1 antibody therapy.

DETAILED DESCRIPTION OF THE INVENTION

Definitions

Figure 1:
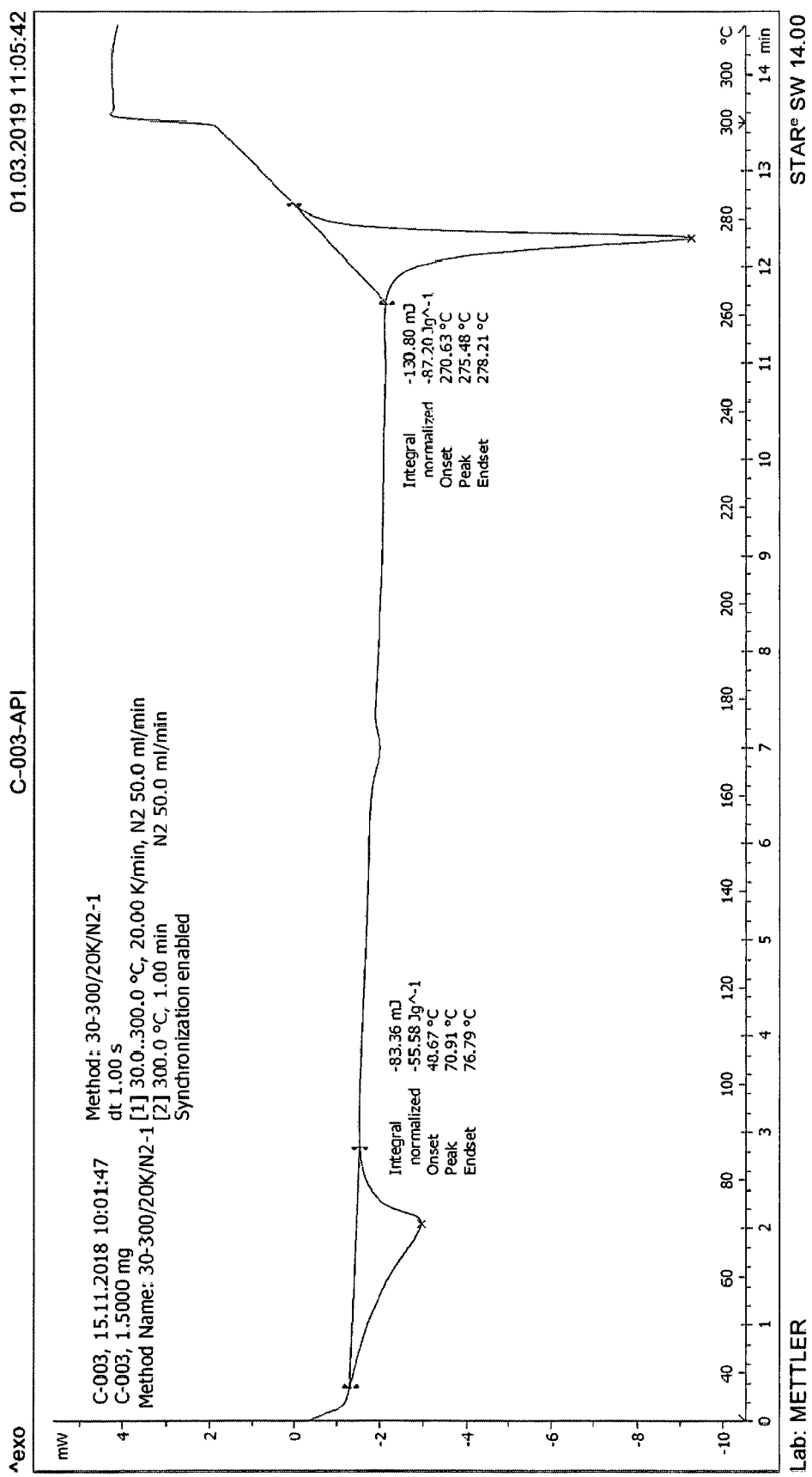
FIG. 1 shows DSC data of C003 free acid.

Abbreviations used herein have their conventional meaning within the chemical and biological arts.

"EP4 antagonist" refers to a compound which inhibits or blocks the cellular signaling triggered by the interaction of PGE2 with the EP4 receptor. Examples of EP4 antagonists include, but not limited to, ER-819762, MK-2894, MF 498, ONO-AE3-208, evatanepag, ONO-AE2-227, CJ-042794, EP4A, BGC201531, CJ-023423, ONO-AE3-240, GW 627368 and AH23848, such as are listed in the IUPHAR database as antagonists of the EP4 receptor. Further examples include, but not limited to, compounds of Formula I as taught herein, including ER-885290, ER-885740, ER-885741, ER-886045, ER-886046(E7046), ER-886074, ER-885290, ER-885740 and ER-885741, which are described in WO 2012/039972.

"Treatment," "treat," and "treating" refer to alleviating, inhibiting and/or reversing the progress of a cancer in a subject in need thereof. The term "treating" is inclusive of any indicia of success in the treatment or amelioration of the cancer, including any objective or subjective parameter such as abatement; remission; diminishing of symptoms or making the injury, pathology or condition more tolerable to the subject; delaying or slowing in the rate of progression, etc. Measurement of the treatment or amelioration may be based on, e.g., the results of a physical examination, a pathological test and/or a diagnostic test as known in the art. Treating may also refer to reducing the incidence or onset of a cancer, or a recurrence thereof (such as a lengthening in time of remission), as compared to that which would occur in the absence of the measure taken.

The terms "neoplasia" and "cancer," as used herein, are interchangeable and include both benign and cancerous tumors, growths and polyps. Thus, the compounds of the invention are useful for treating or preventing benign tumors, growths and polyps including squamous cell papilloma, basal cell tumor, transitional cell papilloma, adenoma, gastrinoma, cholangiocellular adenoma, hepatocellular adenoma, renal tubular adenoma, oncocytoma, glomus tumor, melanocytic nevus, fibroma, myxoma, lipoma, leiomyoma, rhabdomyoma, benign teratoma, hemangioma, osteoma, chondroma and meningioma. The compounds of the invention are also useful for treating or preventing cancerous tumors, growths and polyps including squamous cell carcinoma, basal cell carcinoma, transitional cell carcinoma, adenocarcinoma, malignant gastrinoma, cholangiocelleular carcinoma, hepatocellular carcinoma, renal cell carcinoma, malignant melanoma, fibrosarcoma, myxosarcoma, liposarcoma, leimyosarcoma, rhabdomyosarcoma, malignant teratoma, hemangiosarcoma, Kaposi sarcoma, lymphangiosarcoma, ostreosarcoma, chondrosarcoma, malignant meningioma, non-Hodgkin lymphoma, Hodgkin lymphoma and leukemia. For purposes of this specification, "neoplasia" includes brain cancer, bone cancer, epithelial cell-derived neoplasia (epithelial carcinoma), basal cell carcinoma, adenocarcinoma, gastrointestinal cancer such as lip cancer, mouth cancer, esophogeal cancer, small bowel cancer and stomach cancer, colon cancer, rectal cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that affect epithelial, mesenchymal or blood cells throughout the body. The compounds of the invention are useful for treating or preventing any of the aforementioned cancers. The compounds of the invention are useful for treating or preventing benign and cancerous tumors, growths and polyps of the following cell types: squamous epithelium, basal cells, transitional epithelium, glandular epithelium, G cells, bile ducts epithelium, hepatocytes, tubules epithelium, melanocytes, fibrous connective tissue, cardiac skeleton, adipose tissue, smooth muscle, skeletal muscle, germ cells, blood vessels, lymphatic vessels, bone, cartilage, meninges, lymphoid cells and hematopoietic cells. The compounds can be used to treat subjects having adenomatous polyps, including those with familial adenomatous polyposis (FAP). Additionally, the compounds can be used to prevent polyps from forming in patients at risk of FAP. Preferably, the compounds of the invention are useful for treating or preventing the following cancers: colorectal, esophagus stomach, breast, head and neck, skin, lung, liver, gall bladder, pancreas, bladder, endometrium cervix, prostate, thyroid and brain.

"Alkyl" by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals. Having the number of carbon atoms designated, e.g., $C_{1-10}$ or $C_{1-6}$, means one to ten or one to six carbon atoms. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

"Fluoroalkyl" means alkyl as defined above wherein one or more hydrogen atoms have been replaced by fluoro atoms.

"Alkylene" by itself or as part of another substituent means a divalent radical derived from an alkyl, as exemplified by but not limited to, —$CH_2CH_2CH_2CH_2$—, —$CH_2CH$=$CHCH_2$—, —$CH_2C$≡$CCH_2$—, —$CH_2CH_2CH$ ($CH_2CH_2CH_3$)$CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. A "fused analog" of cycloalkyl means a monocyclic ring fused to an aryl or heteroaryl group in which the point of attachment is on the non-aromatic portion.

Examples of cycloalkyl and fused analogs thereof include cyclopropyl, cyclobutyl, cyclopentyl, cyclohexyl, cycloheptyl, tetrahydronaphthyl, decahydronaphthyl, indanyl, and the like.

"Alkoxy" means alkoxy groups of a straight or branched chain having the indicated number of carbon atoms. $C_{1-6}$alkoxy, for example, includes methoxy, ethoxy, propoxy, isopropoxy, and the like.

"Heteroalkyl," by itself or in combination with another term, means, unless otherwise stated, a stable straight or branched chain, or cyclic hydrocarbon radical, or combinations thereof, consisting of at least one carbon atom and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule.

Examples include but are not limited to —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_3$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both -C(O) OR'- and —R'OC(O)—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cycloalkoxy" means cycloalkyl as defined above bonded to an oxygen atom, such as cyclopropyloxy.

"Fluoroalkoxy" means alkoxy as defined above wherein one or more hydrogen atoms have been replaced by fluoro atoms.

"Aryl" means mono- or bicyclic aromatic rings containing only carbon atoms. A "fused analog" of aryl means an aryl group fused to a monocyclic cycloalkyl or monocyclic heterocyclyl group in which the point of attachment is on the aromatic portion. Examples of aryl and fused analogs thereof include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. A "fused analog" of heteroaryl means a heteroaryl group fused to a monocyclic cycloalkyl or monocyclic heterocyclyl group in which the point of attachment is on the aromatic portion. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

The said aryl groups and said heteroaryl groups referred to in the definitions of Ar1 and Ar2 are unsubstituted or are substituted by at least one substituent selected from the group consisting of substituents a; the said substituents a are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from I to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent-x groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms, aminosulfinyl groups, aminosulfonyl groups, hydroxy groups, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from I to 4 carbon atoms, alkanoylamino groups having from 1 to 4 carbon atoms, alkanoyl(alkyl)amino groups having from 1 to 6 carbon atoms, alkanoylaminoalkyl groups having from 1 to 6 carbon atoms in both the alkanoyl and alkyl part, alkanoyl(alkyl)aminoalkyl groups having from 1 to 6 carbon atoms in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part and alkylsulfonylamino groups having from I to 4 carbon atoms.

"Heterocyclyl" means mono- or bicyclic saturated rings containing at least one heteroatom selected from N, S and O, each of said ring having from 3 to 10 atoms in which the point of attachment may be carbon or nitrogen. A "fused analog" of heterocyclyl means a monocyclic heterocycle fused to an aryl or heteroaryl group in which the point of attachment is on the non-aromatic portion. Examples of "heterocyclyl" and fused analogs thereof include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"Halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

A "prodrug" refers to an agent that is converted into the parent drug in vivo. Prodrugs are often useful because, in some situations, they may be easier to administer than the parent drug. They may, for instance, be bioavailable by oral administration whereas the parent is not.

The prodrugs may also have improved solubility in pharmaceutical compositions over the parent drug. An example, without limitation, of a prodrug would be a compound of Formula I, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug, again without intending to limit the scope of the term, might be one in which a short peptide is bonded to an acid group which is converted to the active moiety inside the cell.

The cancer treated is selected from the group consisting of breast cancers, cervical cancers, colorectal cancers, endometrial cancers, glioblastomas, head and neck cancers, kidney cancers, liver cancers, lung cancers, medulloblastomas, ovarian cancers, pancreatic cancers, prostate cancers, skin cancers and urinary tract cancers.

In more particular aspects of the invention, provided are methods of treating cancer and/or generating a memory immune response. Such methods comprises administering a compound of Formula (I) or a pharmaceutically acceptable salt or prodrug thereof to a subject in need thereof such a treatment:

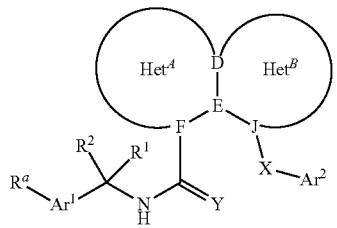

Formula I wherein:

R$^1$ and R$^2$ are independently selected from the group consisting of hydrogen, C$_{1-6}$alkyl, C$_{1-6}$cyclolkyl, C$_{1-6}$fluorocycloalkyl, C$_{1-6}$fluoroalkyl; or, R$^1$ and R$^2$, together with the carbon atom to which they are both attached, complete a three- to six-membered carbocyclic ring which is optionally substituted with R$^c$; or, R$^1$ and R$^2$, together with the carbon atom to which they are both attached, complete a three- to six-membered ring which contains one or two heteroatom(s) such as S, O or NR$^b$, wherein R$^b$ is selected from the group consisting of hydrogen, C$_{1-6}$alkyl, C$_{1-6}$cyclolkyl, C$_{1-6}$fluorocycloalkyl, C$_{1-6}$fluoroalkyl, aryl, heteroaryl, C(O)C$_{1-6}$alkyl, C(O)aryl, S(O)$_2$alkyl, S(O)$_2$aryl;

Y is O or S;

X is a bond, =CH—, CH2, O, or S;

Ar$^1$ and Ar$^2$ are independently selected from the group consisting of C$_{3-6}$cycloalkyl, aryl, heteroaryl and heterocyclyl, or a fused analog of C$_{3-6}$cycloalkyl, aryl, heteroaryl and heterocyclyl, wherein Ar$^1$ and Ar$^2$ are optionally substituted with one to three R$^c$ groups;

R$^c$ is independently selected from halo or R$^1$;

R$^a$ represents —CO$_2$H, —CO$_2$M, —C(O)NHS(O)$_2$R$^{aa}$, or

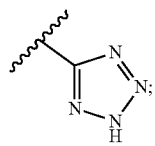 [SMILES: *c1nn[nH]n1]

R$^{aa}$ is selected from C$_{1-6}$ alkyl, C$_{1-6}$ haloalkyl, C$_{1-6}$ cycloalkyl, C$_{1-6}$cyclohaloalkyl, aryl and heteroaryl;

M is an ester prodrug group; and

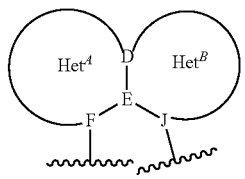

is a 6,6- 5,5- 5,6- or 6,5-bicyclic template.

In one embodiment,

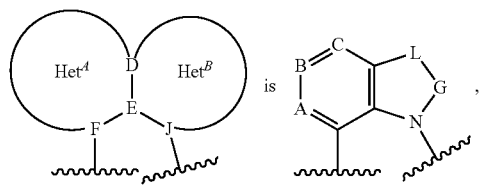

wherein each of A, B and C is independently selected from N, CH and C(R$^c$); G is selected from —C(O), —C(S)—, or —S(O)$_2$—; L is selected from —CH2-, S, O and NRc.

In another embodiment,

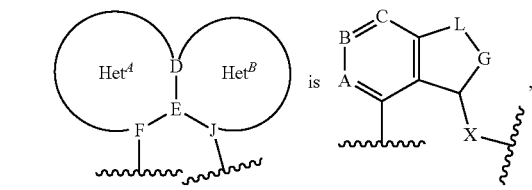

wherein each of A, B and C is independently selected from N, CH and C(R$^c$); X, L and G are each independently selected from a bond, —CH$_2$—, O, S, or N(R$^d$); Rd is H, aryl or alkyl.

In another embodiment,

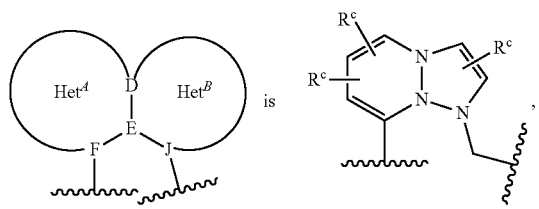

wherein R$^c$ is as previously defined.

In another embodiment

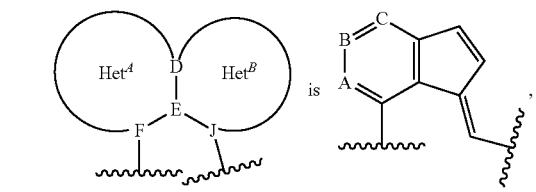

wherein each of A, B and C is independently selected from N, CH and C(R$^c$).

In another embodiment,

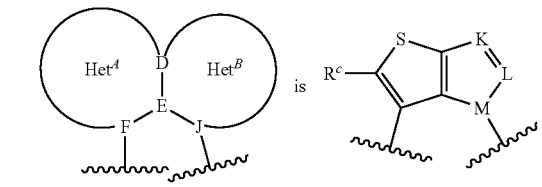

wherein —K-L-M- is selected from the group consisting of: —C(R$^3$)=C(R)—N—, —C(R$^4$)=N—C(R)—, —C(R$^4$)=N—N—, —N=C(R$^4$)—N—, —N=N—N—, —C(R$^4$)$_2$—N=CR$^3$—, —N(R$^4$)—C(R)=CR$^3$—, —N(R$^4$)—N=CR$^3$—, —O—N=CR$^3$— and —S—N=CR$^3$—, wherein R$^3$ is selected from the group consisting of hydrogen, halo, C$_{1-6}$alkyl, C$_{1-6}$fluoroalkyl, C$_{1-6}$alkoxy, C$_{1-6}$fluoroalkoxy and acetyl; each R$^4$ is independently selected from the group consisting of hydrogen, C$_{1-6}$alkyl, C$_{1-6}$fluoroalkyl, C$_{1-6}$alkoxy, C$_{1-4}$ fluoroalkoxy and acetyl.

In another embodiment,

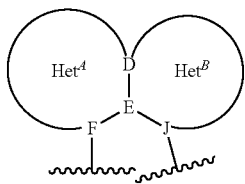

is selected from the following 6,5-hetero-bicyclic moieties:

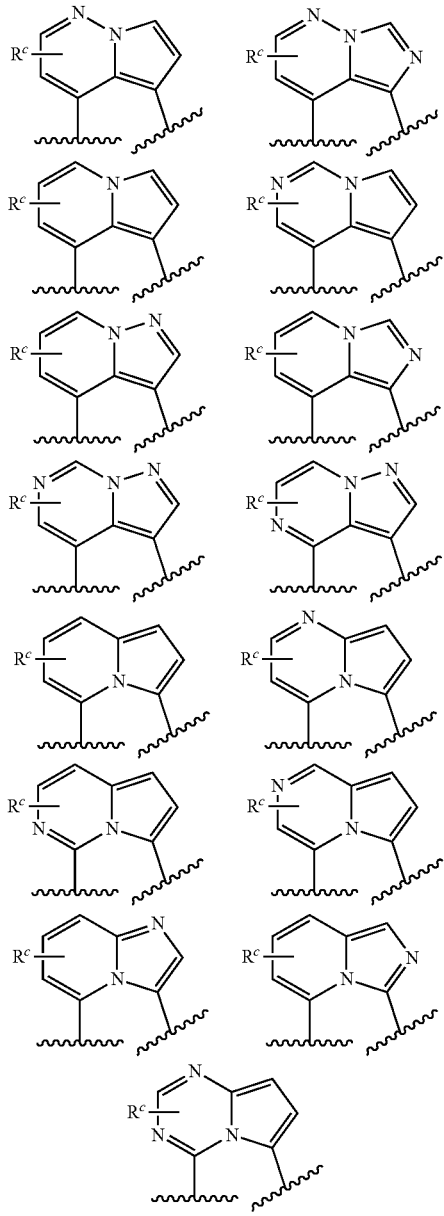

In one embodiment, the present invention relates to compounds of Formula I wherein $R^1$ is methyl and $R^2$ is hydrogen; or wherein $R^1$ is methyl and $R^2$ is methyl; or wherein $R^1$ and $R^2$ together with the carbon atom to which they both are attached form a three- to six-membered carbocyclic ring.

In another embodiment, the present invention relates to compounds of Formula I wherein $Ar^1$ is phenyl, optionally substituted with one to three $R^c$ groups; or compounds of Formula I wherein $Ar^2$ is phenyl, optionally substituted with one to three Rc groups.

The present invention also encompasses a prodrug of Formula I. The prodrug can be an ester or amide or other suitable group. Preferred prodrugs include an ester derivative of Formula Ia:

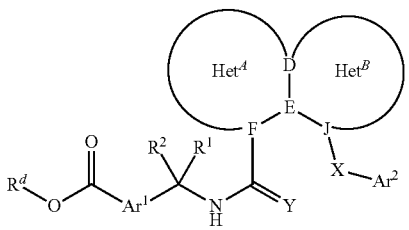

Formula Ia wherein $R^d$ represents an alkyl group having 1 to 10 carbon atoms or an arakly group having from 7 to 12 carbon atoms, aryl, or heteroaryl.

Another preferred prodrug of Formula I is an ester derivative which contains one or more nitric oxide releasing groups (Formula Ib).

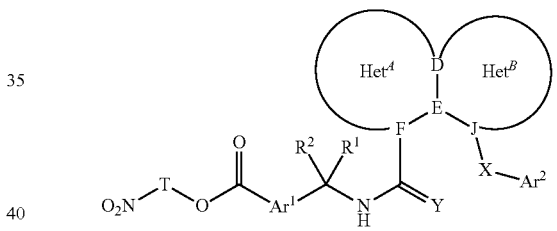

Formula Ib wherein T is any suitable linker.

One embodiment of compounds of nitric oxide-releasing prodrugs of EP4 antagonists are those of Formula Ic or a pharmaceutically acceptable salt thereof:

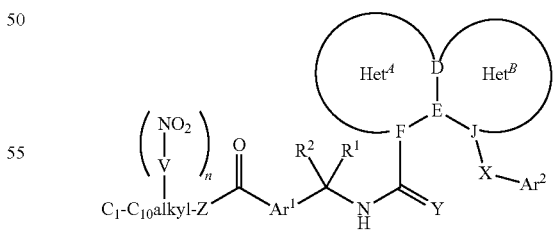

Formula Ic wherein
Z is O, S or $NR^e$, $R^e$ is hydrogen, alkyl or aryl;
each V is independently selected from the group consisting of O and S, and each V is independently attached to any one carbon atom of the $C_{1-10}$alkyl; and
n is 1, 2, 3 or 4.
Another embodiment of compounds of nitric oxide-releasing prodrugs of EP4 antagonists are those of Formula Id.

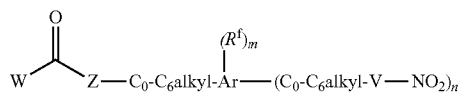

Formula Id wherein

Z is O, S or NRe; Re is hydrogen, alkyl or aryl;

V is O or S; each V is independently attached to one carbon atom of the $C_{1-10}$alkyl;

$R^f$ is selected from the group consisting of hydrogen, halo, alkoxy, alkylthio, CN, $CF_3$, alkyl, alkylsulfonyl, $S(O)_2NH_2$, and $S(O)_2NH$-alkyl; and

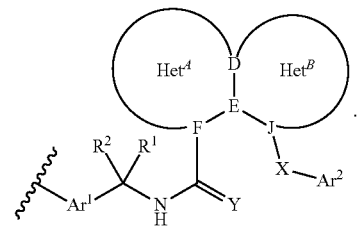

W is

In some embodiments of the pharmaceutically acceptable salts of this invention,

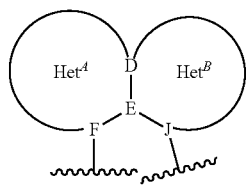

is selected from the following 5,6-heterobicyclic moieties:

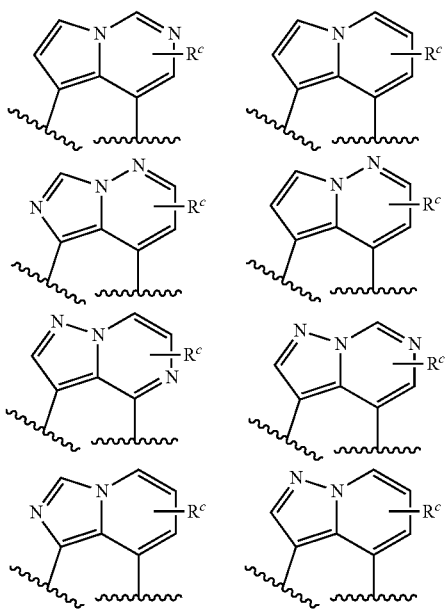

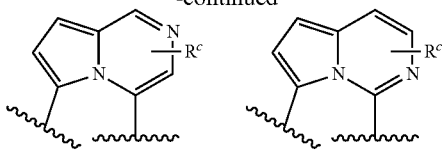

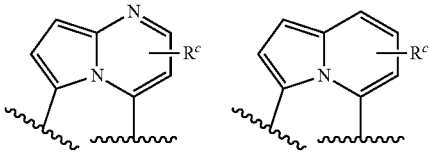

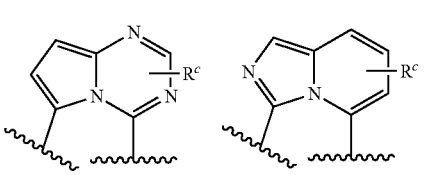

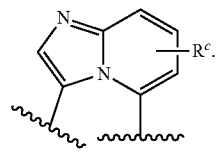

In some embodiments of the pharmaceutically acceptable salts of this invention, —K-L-M- in the compound of Formula I is —C($R^3$)═C($R^4$)—N—, —C($R^3$)═N—N—, —N($R^4$)—C($R^3$)═C—, —N═C($R^3$)—N—, or —N═N—N—.

In some embodiments of the pharmaceutically acceptable salts of this invention, the compound is of Formula Ih, Formula Ih

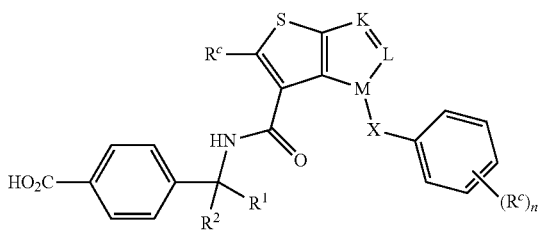

in which:

—K═L-M- is —C($R^3$)═C($R^4$)—N—, —C($R^3$)═N—C($R^4$)—, —C($R^4$)═N—N—, —N═C($R^4$)—N—, —N═N—N—, —C($R^4$)$_2$—N═C—, —N($R^4$)—C($R^3$)═C—, —N($R^4$)—N═C—, —O—N═C—, or —S—N═C—;

n is 1, 2, 3, or 4; and

X is a bond, —$CH_2$—, or —CHR'—.

In some embodiments of the pharmaceutically acceptable salts of this invention, the compound is of Formula Ii, Formula Ii

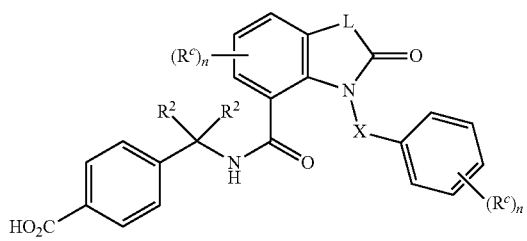

wherein L is —CH$_2$—, O, S, or NR$^1$; n is 1, 2, or 3; and X is a bond, —CH$_2$—, or —CHR$^1$—.

In some embodiments of the pharmaceutically acceptable salts of this invention, the compound is of Formula Ij, Formula Ij

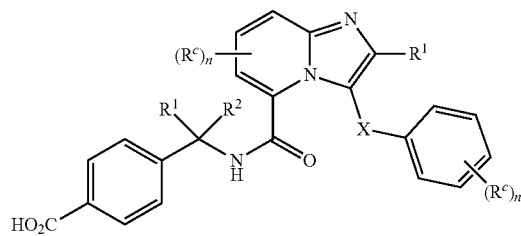

wherein n is 1, 2, or 3; X is a bond, —CH$_2$—, —CHR$^1$—, O, S, or NR$^1$.

In some embodiments of the pharmaceutically acceptable salts of this invention, the compound is of Formula Ik Formula Ik

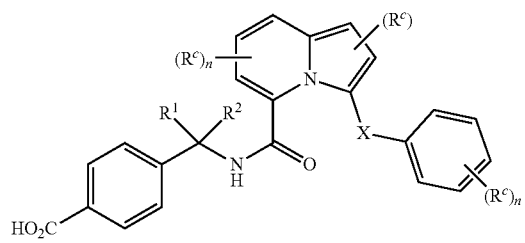

wherein n is 1, 2, or 3; X is a bond, —CH$_2$—, —CHR$^1$—, O, S, or NR$^1$.

In some embodiments of the pharmaceutically acceptable salts of this invention, the compound is of Formula II, Formula II

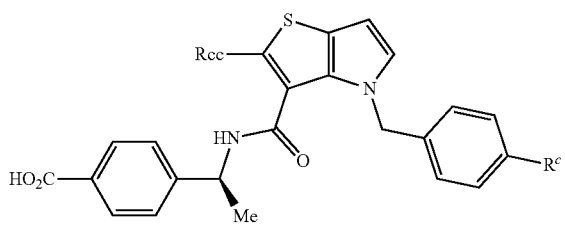

wherein Rcc is hydrogen, C$_{1-6}$ alkyl, or C$_{1-6}$ cycloalkyl;

In some embodiments of the pharmaceutically acceptable salts of this invention, the compound is of Formula Im, Formula Im

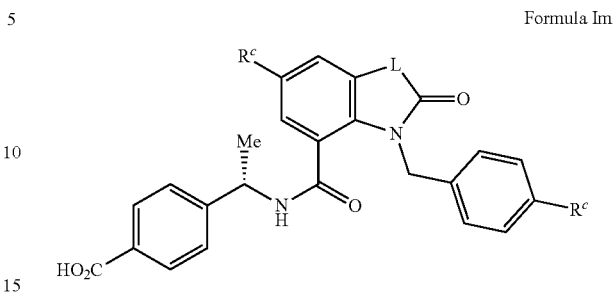

wherein L is O, S, or —CH$_2$—.

In some embodiments of the pharmaceutically acceptable salts of this invention, the compound is of Formula In or a pharmaceutically acceptable salt or prodrug thereof Formula In

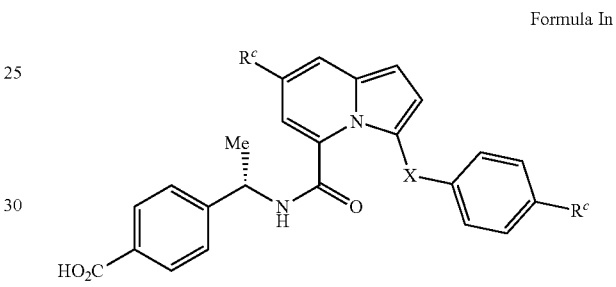

wherein X is a bond, —CH$_2$—, O, or S.

In some embodiments of the pharmaceutically acceptable salts of this invention, the compound is:

4-((1S)-1-{[4-(4-Chlorobenzyl)-4H-thieno[3,2-b]pyrrole-3-carbonyl]amino}ethyl)benzoic acid;

4-((1S)-1-{[4-(4-Chlorobenzyl)-2-methyl-4H-thieno[3,2-b]pyrrole-3-carbonyl]amino}ethyl)benzoic acid;

4-((1S)-1-{[4-(4-trifluoromethylbenzyl)-2-methyl-4H-thieno[3,2-b]pyrrole-3-carbonyl]amino}ethyl)benzoic acid;

4-(1-{[4-(4-Chloro-benzyl)-2-methyl-4H-thieno[3,2-b]pyrrole-3-carbonyl]amino}cyclopropyl)benzoic acid;

4-(1-{[2-Methyl-4-(4-trifluoromethyl-benzyl)-4H-thieno[3,2-b]pyrrole-3-carbonyl]amino}cyclopropyl)benzoic acid;

4-(1-{[5-Oxo-4-(4-trifluoromethylbenzyl)-5,6-dihydro-4H-thieno[3,2-b]pyrrole-3-carbonyl]amino}cyclopropyl)benzoic acid;

4-((1S)-1-{[5-Chloro-1-(4-chlorobenzyl)-2-oxo-2,3-dihydro-1H-indole-7-carbonyl]amino}ethyl)benzoic acid;

4-((1S)-1-{[6-Chloro-3-(4-chlorobenzyl)-2-oxo-2,3-dihydrobenzooxazole-4-carbonyl]amino}ethyl)benzoic acid;

4-(1-{[6-Chloro-2-oxo-3-(4-trifluoromethylbenzyl)-2,3-dihydrobenzooxazole-4-carbonyl]amino}cyclopropyl)benzoic acid;

4-((1S)-1-{[7-Chloro-3-(4-trifluoromethylbenzyl)indolizine-5-carbonyl]amino}ethyl)benzoic acid;

4-(1-{[7-Chloro-3-(4-trifluoromethylphenoxy)indolizine-5-carbonyl]-amino}cyclopropyl)benzoic acid;

4-(1-{[7-Chloro-3-(4-trifluoromethylphenoxy)-imidazo[1,2-a]pyridine-5-carbonyl]amino}cyclopropyl)benzoic acid;

4-((1S)-1-{[7-Chloro-3-(4-trifluoromethylphenoxy)imidazo[1,2-a]pyridine-5-carbonyl]amino}ethyl)benzoic acid;

4-((1S)-1-{[7-Chloro-3-(4-trifluoromethylphenylsulfanyl)-imidazo[1,2-a]pyridine-5-carbonyl]amino}ethyl)benzoic acid;
4-(1-{[7-Chloro-3-(4-trifluoromethylbenzyl)-imidazo[1,2-a]pyridine-5-carbonyl]amino}cyclopropyl)benzoic acid;
4-(1-{[7-Fluoro-3-(4-trifluoromethylbenzyl)-imidazo[1,2-a]pyridine-5-carbonyl]amino}cyclopropyl)benzoic acid;
4-(1-{[7-Fluoro-3-(4-trifluoromethylbenzyl)-indolizine-5-carbonyl]amino}-yclopropyl)benzoic acid;
4-((1S)-1-{[7-Fluoro-3-(4-trifluoromethylbenzyl)indolizine-5-carbonyl]amino}ethyl)benzoic acid;
4-(1-{[7-Fluoro-3-(4-trifluoromethylbenzyl)-indolizine-5-carbonyl]amino}-1-methyl-ethyl)benzoic acid;
4-(1-Methyl-1-{[4-(4-trifluoromethylbenzyl)-4H-thieno[3,2-b]pyrrole-3-carbonyl]amino}ethyl)benzoic acid;
4-(1-{[2-Fluoro-6-(4-trifluoromethylbenzyl)pyrrolo[1,2-a]pyrimidine-4-carbonyl]amino}cyclopropyl)benzoic acid;
4-(1-{[3-Fluoro-7-(4-trifluoromethylbenzyl)pyrrolo[1,2-c]pyrimidine-1-carbonyl]amino}cyclopropyl)benzoic acid;
7-Fluoro-5-(4-trifluoromethylbenzyl)-indolizine-3-carboxylic acid (1-phenylcyclopropyl)amide; and
7-Fluoro-5-(4-trifluoromethylbenzyl)-imidazo[1,2-a]pyridine-3-carboxylic acid (1-phenylcyclopropyl)amide.

In another aspect, the present provide pharmaceutical compositions containing a pharmaceutically acceptable salt described above and a pharmaceutically acceptable carrier.

Also within the scope of this invention are methods for treating cancer or inflammatory diseases in a subject in need thereof with a pharmaceutically acceptable salt or a pharmaceutical composition described above.

Examples of the cancer include but are not limited to breast cancer, endometrial cancer, cervix cancer, ovary cancer, lung cancer, head and neck cancer, brain cancer, thyroid cancer, oesophagus cancer, stomach cancer, colon & rectal cancer, liver cancer, pancreatic cancer, skin cancer, kidney cancer, bladder cancer, prostate cancer, testis cancer, bone cancer, Lymphoma, and blood cancer; and examples of the inflammatory diseases include but are not limited to arthritis, acne vulgaris, asthma, autoimmune diseases, autoinflammatory diseases, Celiac disease, chronic prostatitis, colitis, diverticulitis, glomerulonephritis, hidradenitis suppurativa, hypersensitivities, inflammatory bowel diseases, interstitial cystitis, Mast Cell Activation Syndrome, mastocytosis, otitis, pelvic inflammatory disease, reperfusion injury, rheumatic fever, rheumatoid arthritis, rhinitis, sarcoidosis, and vasculitis.

In some embodiments, the method of this invention may further comprise a second therapeutic agent or action selected from the group consisting of radiation, antibodies to cytotoxic t-lymphocyte antigen 4 (anti-CTLA4), antibodies to programmed death ligand 1 (anti-PDL1), antibodies to programmed cell death protein 1 (anti-PD1), and antimetabolites have been examined.

In some other embodiments, the method of this invention may also comprise another therapeutic agent or action selected from the group consisting of radiation, antibodies to cytotoxic t-lymphocyte antigen 4 (anti-CTLA4), antibodies to programmed death ligand 1 (anti-PDL1), antibodies to programmed cell death protein 1 (anti-PD1), and antimetabolites.

It will be appreciated that certain compounds of Formula I (or salts, prodrugs, or conjugates) may exist in, and be isolated in, isomeric forms, including tautomeric forms, cis- or trans-isomers, as well as optically active, racemic, or diastereomeric forms. It is to be understood that the present invention encompasses a compound of Formula I in any of the tautomeric forms or as a mixture thereof; or as a mixture of diastereomers, as well as in the form of an individual diastereomers, and that the present invention encompasses a compound of Formula I as a mixture of enantiomers, as well as in the form of an individual enantiomer, any of which mixtures or form possesses antagonistic properties against EP4 receptor, it being well known in the art how to prepare or isolate particular forms and how to determine antagonistic properties against EP4 receptor by standard tests including those described herein below.

In addition, a compound of Formula I (or salt, prodrug or conjugate thereof) may exhibit polymorphism or may form a solvate with water or an organic solvent. The present invention also encompasses any such polymorphic form, any solvate or any mixture thereof.

As mentioned above, the invention includes pharmaceutically acceptable salts or prodrugs of compounds of Formula I. A basic compound of Formula I possesses one or more functional groups sufficiently basic to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like.

The invention also encompasses other acceptable forms of prodrugs of Formula I formed in a conventional manner with a functional group of the compound such as with an amino, hydroxy, or carboxy group.

The invention also encompasses a method of treating a human or animal subject suffering from a condition which is mediated by the action of PGE2 at EP4 receptors, which method comprises administering to said subject an effective amount of a compound of Formula I.

The invention also encompasses use of a compound of Formula I for the manufacture of a medicament for the treatment of a disease or condition that is mediated by the action of PGE2 at EP4 receptors.

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I to Formula Ig.

Some of the compounds described herein contain olefinic double bonds, and unless specified otherwise, are meant to include both E and Z geometric isomers.

Compounds described herein may exist with different points of attachment of hydrogen, referred to as tautomers. For example, a ketone and its enol form are known as keto-enol tautomers. The individual tautomers as well as mixtures thereof are encompassed with compounds of Formula I to Formula Ig.

Compounds of Formula I may be separated into diastereoisomeric pairs of enantiomers by, for example, fractional crystallization from a suitable solvent, such as MeOH or EtOAc or a mixture thereof. Enantiomers thus obtained may be separated into individual stereoisomers by conventional means, for example by use of an optically active amine as a resolving agent, or on a chiral HPLC column.

Alternatively, any enantiomer of a compound of Formula I may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility.

Recrystallization solvent, rate of crystallization, storage temperature, and other factors may cause one crystal form to dominate. Crystal polymorphs of the compounds can be prepared by crystallization under different conditions. It is understood that the compounds of the present disclosure may exist in crystalline form, crystal form mixture, or anhydride or hydrate thereof.

Compounds of Formula I can also be used in combination with one or more chemotherapeutic agents such as:

an aromatase inhibitor, an antiestrogen, an anti-androgen (especially in the case of prostate cancer) or a gonadorelin agonist, a topoisomerase I inhibitor or a topoisomerase II inhibitor, a microtubule active agent, an alkylating agent, an antineoplastic antimetabolite or a platin compound, a compound targeting/decreasing a protein or lipid kinase activity or a protein or lipid phosphatase activity, a further anti-angiogenic compound or a compound which induces cell differentiation processes, a bradykinin I receptor or an angiotensin II antagonist, a cyclooxygenase inhibitor, a bisphosphonate, a rapamycin derivative such as everolimus, a heparanase inhibitor (prevents heparan sulphate degradation), e.g. PI 88, a biological response modifier, preferably a lymphokine or interferons, e.g. interferon if, an ubiquitination inhibitor, or an inhibitor which blocks anti-apoptotic pathways, an inhibitor of Ras oncogenic isoforms, e. g. H-Ras, K-Ras or N-Ras, or a farnesyl transferase inhibitor, e.g. L-744, 832 or DK8G557, a telomerase inhibitor, e.g. telomestatin, a protease inhibitor, a matrix metalloproteinase inhibitor, a methionine aminopeptidase inhibitor, e.g. bengamide or a derivative thereof, or a proteasome inhibitor, e.g. PS 341, histone deacetylase inhibitors, e.g. Vorinostat, MG0103 or MS275, or PTP 1B inhibitors, and IDO1 or IDO1/TDO inhibitors.

It is to be understood that reference to treatment includes both treatment of established symptoms and prophylactic treatment, unless explicitly stated otherwise.

The terms "nitric oxide releasing-EP4 antagonist" or "NO-EP4 antagonist," mean a modified version of a selective EP4 antagonist prodrug as defined herein linked to a NO releasing moiety by means of a linking group such as an ester linkage.

The term "amounts that are effective to treat" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician. The NO-EP4 antagonist may be administered at a dosage level up to conventional dosage levels for NSAIDs. Suitable dosage levels will depend upon the anti-inflammatory effect of the chosen EP4 antagonist, but typically suitable levels will be about 0.001 to 50 mg/kg per day, preferably 0.005 to 30 mg/kg per day, and especially 0.05 to 10 mg/kg per day. The compound may be administered on a regimen of once, twice or three times per day.

Formulations

The present invention also provides a pharmaceutical composition for use in the above-described therapeutic methods. Pharmaceutical compositions of the present invention comprise a compound of Formula I or pharmaceutically acceptable salt (e.g., diethanolamino salt, a diethanolamino salt, or a TRIS salt) thereof as an active ingredient or a pharmaceutically acceptable salt, thereof, in an amount sufficient to antagonize EP4 receptor, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that in the discussion of methods of treatment herein references to the compounds of Formula I are meant to also include the pharmaceutically acceptable salts.

Pharmaceutical compositions containing an active ingredient (i.e., a compound of Formula I or pharmaceutically acceptable salt thereof) may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874, the contents of which are herein incorporated by reference, to form osmotic therapeutic tablets for controlled release.

Combination Therapy

Compounds of Formula I may be used in combination with other drugs useful in the treatment/prevention/suppression or cancer or conditions for which compounds of Formula I are useful. Such other drugs may be administered, by a route and in an amount commonly used therefor, contemporaneously or sequentially with a compound of Formula 1. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula 1. When compounds of the invention are used in combination with other therapeutic agents, the compounds may be administered either sequentially or simultaneously by any convenient route.

The invention thus provides, in a further aspect, a combination comprising a compound of Formula I or a pharmaceutically acceptable derivative or salt thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

In some embodiments of the present invention, provided is a method of inhibiting tumor growth or treating cancer wherein an EP4 antagonist is administered in combination with an additional therapy or agent useful for inhibiting tumor growth and/or treating cancer, i.e., a combination therapy. As used herein, the administration of two or more agents/therapies (inclusive of EP4 antagonists, radiation therapy, antibody therapy, anti-metabolite chemotherapy, or any combination thereof) "in combination" means that the therapies are administered closely enough in time that the administration of or presence of one alters the biological effects of the other. The therapies may be administered simultaneously (concurrently) or sequentially. Simultaneous administration may be carried out, e.g., by mixing two or more agents prior to administration, or by administering the agent/therapy at the same point in time but at different anatomic sites or using different routes of administration, or administered at times sufficiently close that the results observed are indistinguishable from those achieved when the agents/therapies are administered at the same point in time. For example, simultaneous administration of one or more agents with radiation may be carried out by administering the agent(s) at the same point in time as the radiation is applied, or at times sufficiently close that the results observed are indistinguishable from those achieved when the agent(s) and radiation are administered at the same point in time. Sequential administration may be carried out by administering the agents/therapies at different points in time, e.g., administering an agent at some point in time prior to or after administration of one or more other agents/therapies, such that the administration of the agents/therapies in combination enhances the therapeutic effect of cancer treatment. In some embodiments, an EP4 antagonist is administered at some point in time prior to the initial administration of radiation therapy, antibody therapy and/or anti-metabolite chemotherapy. Alternatively, the radiation therapy, antibody therapy and/or anti-metabolite chemotherapy may be administered at some point in time prior to the administration of the EP4 antagonist, and optionally, administered again at some point in time after the administration of the EP4 antagonist. In some embodiments, administration of the EP4 antagonist in combination with radiation therapy, antibody therapy and/or anti-metabolite chemotherapy results in an enhancement of said radiation therapy, antibody therapy and/or anti-metabolite chemotherapy such that, for example, a smaller dosage of the radiation, antibody therapy and/or anti-metabolite chemotherapy may be effective for treatment. In some embodiments of the invention, the treatment of cancer may comprise an abscopal effect and/or provide a memory immune response. An "abscopal" effect is a phenomenon in the treatment of a metastatic cancer in which localized treatment of a particular tumor or cancer with, for example, radiation therapy, results in the shrinking and disappearance of non-localized disease, tumors or cancer, such as those resulting from metastasis that are distant from the site of localized treatment, thus leading to the disappearance of disease, tumors or cancer throughout the subject or patient. An abscopic effect differs from effects that may occur on tissues adjacent to the localized treatment, such as, for example, bystander effects that may result from radiation therapy. A "memory immune response" results when the provided treatment for cancer facilitates the adaptation of the immune system and the immune response of the subject or patient in its ability to slow, reduce or prevent the rectum or the recurrence, e.g., lengthening the time of remission, of the disease, tumor or cancer being treated in the subject or patient. In some embodiments, the memory immune response may slow, reduce or prevent the development of tumors or cancers that are different than the cancer being treated, e.g., through epitope spreading. The EP4 antagonist, antibody and/or anti-metabolite as used herein may be formulated for administration in a pharmaceutical carrier in accordance with known techniques. See, for example, Remington, The Science and Practice of Pharmacy (9th Ed. 1995). In the manufacture of a pharmaceutical formulation according to the invention, the active compound (including the physiologically acceptable salts thereof) is typically admixed with, inter alia, an acceptable carrier. The carrier must be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well-known techniques of pharmacy comprising admixing the components, optionally including one or more accessory ingredients and/or excipients. In some embodiments, any of the composition, carrier, accessory ingredient(s) excipient(s) and/or the formulation(s) of the invention comprise ingredients that are from either natural or non-natural sources. In other embodiments, any component of the composition(s), carrier(s), accessory ingredient, excipient(s) and/or the formulation(s) of the invention may be provided in a sterile form. Non-limiting examples of a sterile carrier include endotoxin-free water or pyrogen-free water. The EP4 antagonist, antibody and/or anti-metabolite can be administered to subjects by any suitable route, including orally (inclusive of administration via the oral cavity and further including administration via an orogastric feeding tube), intraperitoneally, parenterally, by inhalation spray, topically (i.e., both skin and mucosal surfaces, including airway surfaces), transdermally, rectally, nasally (including a nasogastric feeding tube), sublingually, buccally, vaginally or via an implanted reservoir. The term "parenteral" as used herein includes subcutaneous, intramuscular, intradermal, intravenous, intra-articular, intra-synovial, intrasternal, intrathecal, intrahepatic, intralesional and intracranial inectionor infusion techniques. In a particular embodiment, the EP4 antagonist, antibody and/or anti-metabolite is administered orally. In another particular embodiment, the EP4 antagonist, antibody and/or anti-metabolite is administered intravenously. In some embodiments, the amount of the EP4 antagonist, antibody and/or anti-metabolite that may be combined with the excipient materials to produce a composition in a single dosage form will vary depending upon the host treated, and the particular route of administration. In some embodiments, the EP4 antagonist, antibody and/or anti-metabolite is provided as part of a sterile composition/formulation comprising the EP4 antagonist, antibody and/or anti-metabolite and an acceptable carrier and/or excipient. In some embodiments, the EP4 antagonist is administered to the subject in an effective amount. An effective amount is generally 0.01 mg/kg to 500 mg/kg body weight per day. In some embodiments, the pharmaceutically acceptable compositions may be formulated so that a dosage of from 0.01 mg/kg to 200 mg/kg or from 0.01 mg/kg to 100 mg/kg body weight per day of the compound can be administered to a patient receiving these compositions (e. g., based on a 75 kg human, a dosage of from 0.75 mg to 7.5 g or 15 g). In certain embodiments, the compositions of the present invention are formulated to provide a dosage of from 0.01 mg/kg to 70 mg/kg (e.g., based on a 75 kg human, a dosage of from 0.75 mg to 5.25 g). In some embodiments, the effective dose of the EP4 antagonist is from about 0.5 to about 250 mg/kg, 1 to about 250 mg/kg, from about 2 to about 200 mg/kg, from about 3 to about 120 mg/kg, from about 5 to about 250 mg/kg, from about 10 to about 200 mg/kg, or from about 20 to about 120 mg/kg. In some embodiments, effective dosages include about 0.5 mg/kg, 1 mg/kg, 2 mg/kg, 3 mg/kg, 4 mg/kg, 5 mg/kg, 6 mg/kg, 8 mg/kg, 10 mg/kg, 20 mg/kg, 25 mg/kg, 40 mg/kg, 50 mg/kg, 60 mg/kg, 75 mg/kg, 100 mg/kg, 120 mg/kg, 150 mg/kg, 175 mg/kg, 200 mg/kg, 225 mgl/kg, 250 mg/kg, and 300 mg/kg. Dosage forms can be in the form, e.g., of tablets or capsules, and the effective dose may be provided in one or more tablets, capsules or the like, and be provided once a day or throughout the day at intervals, e.g., of 4, 8 or 12 hours. Tablets or capsules, for example, could contain, e.g., 10, 25, 50, 75, 100, 150, 200, 250, 300, 350, 400, 450, 500, 600, 700, 800, 900, 1,000, 1,100, or 1,250 mg of compound. For example, administration to a human subject of the EP4 antagonist in some embodiments may comprise a daily dosage of the EP4 antagonist in the range of 100-1,250, 150-1,000, 200-800, or 250-750 mg, which daily dosage can be administered either once a day in its entirely or factions of which are administered throughout the day in intervals. Liquid formulations can also be prepared so that any dosage may readily and conveniently be dispensed. The antibody, e.g., anti-CTLA4, anti-PDL1 or anti-PD1, will generally be mixed, prior to administration, with a non-toxic, pharmaceutically acceptable carrier substance (e.g., normal saline or phosphate-buffered saline), and may be administered using any medically appropriate procedure, for example, including but not limited to, intravenous or intra-arterial administration, and injection into the cerebrospinal fluid. In certain cases, intraperitoneal intradermal, intracavity, intrathecal or direct administration to tumor or to an artery supplying the tumor may be advantageous. In some embodiments, the effective dose of the antibody is from about 5 to about 250 mg/kg, from about 10 to about 200 mg/kg, or from about 20 to about 120 mg/kg. In some embodiments, effective dosages include 5 mg/kg, 10 mg/kg, 20 mg/kg, 25 mg/kg, 40 mg/kg, 50 mg/kg, 60 mg/kg, 75 mg/kg, 100 mg/kg, 120 mg/kg, 150 mg/kg, 175 mg/kg, 200 mg/kg, 225 mg/kg, 250 mg/kg, and 300 mg/kg. Dosage forms can be in the form, e.g., of tablets or capsules, and the effective dose may be provided in one or more tablets, capsules or the like, and be provided once a day or throughout the day at intervals, e.g., of 4, 8 or 12 hours. Tablets or capsules, for example, could contain, e.g., 10, 25, 50, 75, 100, 150, 200, 250, 300, 350, 400, 450, 500, 600, 700, 800, 900, or 1,000 mg of antibody. Liquid formulations can also be prepared so that any dosage may readily and conveniently be dispensed. In some embodiments, the antibody is administered the subject in an effective amount. An effective amount is generally 0.01 mg/kg to 500 mg/kg body weight per day. In some embodiments, the pharmaceutically acceptable compositions may be formulated so that a dosage of from 0.01 mg/kg to 200 mg/kg or from 0.01 mg/kg to 100 mg/kg body weight per day of the compound can be administered to a patient receiving these compositions (e.g., based on a 75 kg human, a dosage of from 0.75 mg to 7.5 g or 15 g). In certain embodiments, the compositions of the present invention pre-formulated to provide a dosage of from 0.01 mg/kg to 70 mg/kg (e.g., based on a 75 kg human, a dosage of from 0.75 mg to 5.25 g). An effective amount of the antibody may be, for example, 0.05 mg/kg, 0.1 mg/kg, 1 mg/kg, 2 mg/kg, 3 mg/kg, 4 mg/kg, 5 mg/kg, 6 mg/kg, 7 mg/kg or 8 mg/kg per dose (e.g., based on a 75 kg human, a dosage of from 3.75 mg to 600 mg). The dosage of the antibody may be administered once, twice, three times, four times, five times or more per week, once every week, once every two weeks, or even once every three weeks during the course of treatment. The timing of the dosing may be daily, once every two days, once every three days, once every four days, once every five days, weekly, once every two weeks or once every three weeks. Formulations comprising the antibody may be prepared so that any dosage may readily and conveniently be dispensed.

The term "concomitantly administering" means administering one or more therapeutic agents substantially concurrently. The term "concomitantly administering" encompasses not only administering two agents in a single pharmaceutical dosage form but also administration of each active agent in its own separate pharmaceutical dosage formulation. Where separate dosage formulations are used, the agents can be administered at essentially the same time, i.e., concurrently.

The term "sequentially administering" means administering agents at separately staggered times. Thus, for example, agents can be sequentially administered such that the beneficial pharmaceutical effect of aspirin and a compound of the present invention are realized by the patient at substantially the same time. Thus, for example, if a compound of the present invention and aspirin are both administered on a once a day basis, the interval of separation between sequential administration of the two agents can be up to twelve hours apart.

"Effective amount" or "treatment-effective amount" refers to amount that is effective for treating a cancer as noted through clinical testing and evaluation, patient observation, and/or the like. An "effective amount" can further designate an amount that causes a detectable change in biological or chemical activity. The detectable changes may be detected and/or further quantified by one skilled in the art for the relevant mechanism or process.

Moreover, an "effective amount" can designate an amount that maintains a desired physiological state, i.e., reduces or prevents significant decline and/or promotes improvement in the condition. An "effective amount" can further refer to a therapeutically effective amount. "Subject" as used herein refers a mammalian subject, and particularly a human subject, including a male or female subject, and including a neonatal, infant, juvenile, adolescent, adult or geriatric subject, and further is inclusive of various races and ethnicities.

The terms "antibody" and "antibodies" as used herein is inclusive of all types of immunoglobulins, including IgG, IgM, IgA, IgD, and IgE, or fragments thereof, that may be appropriate for the medical uses disclosed herein. The antibodies may be monoclonal or polyclonal and may be of any species of origin, including, for example, mouse, rat, rabbit, horse, or human. Antibody fragments that retain specific binding to the protein or epitope, for example, CTLA4, PDL1 or PD1, bound by the antibody used in the present invention are included within the scope of the term "antibody." Such fragments can be produced by known techniques. The antibodies may be chimeric or humanized, particularly when they are used for therapeutic purposes. The antibody may be obtained or prepared using methods known in the art. "Antibody therapy" refers to the medical use of antibodies that bind a target cell or protein to treat cancer and/or stimulate an immune response in a subject that results in the recognition, attack and/or destruction of cancerous cells in the subject, and in some embodiments of the invention, to activate or stimulate a memory immune response in a subject that results in the subsequent recognition, attack and/or destruction of cancerous cells in the subject. "CTLA4 antibody therapy" refers to the use of antibodies directed toward cytotoxic t-lymphocyte antigen 4 (anti-CTLA4) in modulating an immune response in a subject. In some embodiments, the CTLA4 antibody inhibits or blocks the action of CTLA4 signaling that results in the inhibition of T-cell activation in the attack and destruction of cancer cells. Suitable antibodies for this use include, but are not limited to, antibodies that are CTLA4 antagonists or the CTLA4 antibodies as set forth in U.S. Pat. Nos. 8,685,394 and 8,709,417. Some embodiments of the antibody include MDX-010 (Ipilimumab, Bristol-Myers Squibb) and CP-675,206 (Tremelimumab, Pfizer). In a particular embodiment, the antibody is ipilimumab. "PDL1 antibody therapy" refers to the use of antibodies directed toward programmed death ligand 1 (anti-PDL1) in modulating an immune response in a subject. In some embodiments, the PDL1 antibody inhibits or blocks the interaction of PDL1 with programmed cell death protein 1 (PD1), wherein the blockage of the interaction between PDL1 and PD1 inhibits the negative regulation of T-cell activation by PD 1 to attack and destroy cancer cells. Suitable antibodies for this use include, but are not limited to, the antibodies set forth in U.S. Pat. Nos. 8,217,149, 8,383,796, 8,552,154 and 8,617,546. In a particular embodiment, the antibody is MPDL3280A (Roche). "PD 1 antibody therapy" refers to the use of antibodies directed toward programmed cell death protein 1 PD1 (anti-PD1) in modulating an immune response in a subject. In some embodiments, the PD1 antibody inhibits or blocks the interaction of PD1 with PDL1, wherein the inhibition or blockage of the interaction between PDL1 and PD1 inhibits the negative regulation of T-cell activation by PD 1 to attack and destroy cancer cells. Suitable antibodies for this use include, but are not limited to, the antibodies set forth in U.S. Pat. Nos. 7,029,674, 7,488,802, 7,521,051, 8,008,449, 8,354,509, 8,617,546 and 8,709,417. Particular embodiments of the antibody include MDX-I1 06 (nivolurmab, Bristol-Myers Squibb), and pembrolizumab (KEYTRUDA, Merck).

"Anti-metabolite chemotherapy" refers to the use of an anti-metabolite chemotherapeutic in the treatment of a subject. "Anti-metabolite" refers to a group of molecules that impede DNA and RNA synthesis. Examples of anti-metabolites include, but are not limited to, anti-folates, fluoropyrimidines, deoxynucleoside analogues and thiopurines.

Anti-folates include methotrexate and pemetrexed. Fluoropyrimidines include fluorouracil and capecitabine. Deoxynucleoside analogues include cytarabine, gemcitabine, decitabine, 5'-azacytidine (VIDAZA), fludarabine, nelarabine, cladribine, clofarabine and pentostatin. Thiopurines include thioguanine and mercaptopurine. In one embodiment, the anti-metabolite is gemcitabine. In another embodiment, the anti-metabolite is capecitebine. In order that the invention described herein may be more fully understood, the following examples are set forth. It should be understood that these examples are for illustrative purposes only and are not to be construed as limiting this invention in any manner.

Assays for Determining Biological Activity

The compounds of Formula I can be tested using the following assays to determine their prostanoid antagonist or agonist activity in vitro and in vivo and their selectivity. The prostaglandin receptor activities demonstrated are DP, EP1, EP2, EP3, EP4, FP, IP and TP.

Example A. Stable Expression of Prostanoid Receptors in the Human Embryonic Kidney (HEK) 293(Ebna) Cell Line Prostanoid receptor cDNAs corresponding to full length coding sequences were subcloned into the appropriate sites of mammalian expression vectors and transfected into HEK 293 cells. HEK 293 cells expressing the individual cDNAs were grown under selection and individual colonies are isolated after 2-3 weeks of growth using the cloning ring method and subsequently expanded into clonal cell lines.

Example B. Prostanoid Receptor Binding Assays

Transfected HEK 293(ebna) cells were maintained in culture, harvested and membranes are prepared by differential centrifugation, following lysis of the cells in the presence of protease inhibitors, for use in receptor binding assays. Prostanoid receptor binding assays (for DP1, DP2 (CRTH2), EP1, EP2, EP3-III, EP4, FP, IP, and TP) were performed in 10 mM MES/KOH (pH 6.0) (EPs, FP and TP) or 10 mM HEPES/KOH (pH 7.4) (DPs and IP), containing 1 mM EDTA, 2.5-30 mM divalent cation and the appropriate radioligand. Test compounds of this invention were added in dimethylsulfoxide (DMSO) to a concentration kept constant at 1% (v/v) in all incubations. The reaction is initiated by addition of membrane protein. Non-specific binding was determined in the presence of 10 μM of the corresponding non-radioactive prostanoid. Incubation was conducted for 60-90 mins at the room temperature or 30° C. and terminated by rapid filtration. Specific binding was calculated by subtracting non-specific binding from total binding. The residual specific binding at each ligand concentration was calculated and expressed as a function of ligand concentration in order to construct sigmoidal concentration-response curves. The binding affinity of the compounds was determined by calculating the equilibrium inhibition constant (Ki) from the equation Ki=InPt/1+[radioligand]/Kd where Kd is the equilibrium dissociation constant for the radioligand:receptor interaction and InPt is the inflection point of the dose-response curves.

Example C. Prostanoid Receptor Agonist and Antagonist Assays

Whole cell second messenger assays measuring stimulation of intracellular cAMP accumulation in HEK-293(ebna)-hEP4 cells were performed to determine whether receptor ligands are agonists or antagonists. Cells were harvested and re-suspended in HBSS containing 25 mM HEPES, pH 7.4. Incubations contain 0.5 mM IBMX (phosphodiesterase inhibitor, available from Biomol). Samples were incubated at 37° C. for 10 mins, the reaction was terminated and cAMP levels were then measured. Ligands were added into dimethylsulfoxide for a concentration kept constant at 1% (v/v; agonists) or 2% (v/v; antagonists) in all incubations. For agonists, second messenger responses were expressed as a function of ligand concentration and both $EC_{50}$ values and the maximum response as compared to a PGE2 standard were calculated. For antagonists, the ability of a ligand to inhibit an agonist response was determined by carrying out dose-response curves in the presence of PGE2 agonist at a concentration corresponding to its EC70. $IC_{50}$ values were calculated as the concentration of ligand required to inhibit 50% of the PGE2-induced activity.

The data provide evidence that the tested heterocyclic amide EP4 antagonists of this invention had significant anti-tumor growth activity in immunocompetent animal cancer models. Combination treatment of heterocyclic amide EP4 antagonist plus antibody should significantly enhance the anti-tumor activity compared with treatment with antibody alone, and thus is expected to have therapeutic use in the clinic for treating cancer.

ADDITIONAL EXAMPLES

General:

Microwave heating was done using Biotage Emrys Liberator or Initiator microwave.

Column chromatography was carried out using Biotage SP4. Solvent removal was carried out using either a Büchi rotary evaporator or a Genevac centrifugal evaporator. Preparative LCIMS was conducted using a Waters autopurifier and 19×100 mm XTerra 5 micron MS C18 column under acidic mobile phase condition. NMR spectra were recorded using Bruker 400 MHz spectrometer.

When the term "inerted" is used to describe a reactor (e.g., a reaction vessel, flask, glass reactor, and the like), it is meant that the air in the reactor has been replaced with an essentially moisture-free or dry, inert gas (such as nitrogen, argon, and the like).

General methods and experiments for preparing compounds of the present invention are set forth below. In certain cases, a particular compound is described by way of example.

However, it will be appreciated that in each case a series of compounds of the present invention were prepared in accordance with the schemes and experiments described below.

NMR: $^1$H-NMR spectra were taken using $CDCl_3$ unless otherwise stated and were recorded at 400 or 500 MHz using a Varian instrument. Multiplicities indicated are s=singlet, d=doublet, t=triplet, q=quartet, quint=quintet, sxt=sextet, m=multiplet, dd=doublet of doublets, dt=doublet of triplets, b=a broad signal. Mass: Waters Acquity Ultra Performance LC.

Instrument Parameters

Declaration: Listed analytical methods were the general methods and any revised methods were marked in the report.

XRPD (X-ray Powder Diffractometer)

The X-ray powder diffraction (XRPD) pattern was obtained on a Shimadzu XRD-6000 instrument. Samples were run on XRPD using below method:

Tube: Cu: K-Alpha (λ=1.54056 Å)
Generator: Voltage: 40 kV; Current: 30 mA
Scan Scope: 5 to 50 deg. Scanning rate: 5 deg./min
DSC (Differential Scanning Calorimeter)

Exemplary compounds of this invention (~1 mg) were tested in a pinhole aluminum pans under nitrogen purge using a ramp rate of 20° C./min over the range 30° C.~300° C.

TGA (Thermal Gravimetric Analysis)

Samples of compounds (4~6 mg) were weighed into the pan, and heated under nitrogen purge using a ramp rate of 20° C./min over the range of 30° C.~350° C.

DVS (Dynamic Vapor Sorption)

Around 20 mg of samples were used to test its moisture sorption/desorption profiles at 25° C. under 0%~95%~0% relative humidity (RH) cycle with the following parameters:

Temperature: T=25° C.

Equilibrium: dm/dt: 0.01%/min.

RH (%) measurement step scope: 0%95%0%; RH (%) measurement step: 5%

| Hygroscopicity Classification | Water Sorption Criterion* |
|---|---|
| Deliquescent | Sufficient water is absorbed to form a liquid |
| Very hygroscopic | W % ≥ 15% |
| Hygroscopic | W % ≥ 2% |
| Slightly hygroscopic | W % ≥ 0.2% |
| Non-hygroscopic | W % ≥ 0.2% |

*At 25 ± 1° C. and 80 ± 2% RH (European Pharmacopoeia 6.0)

PLM (Polarized Light Microscope)

Samples dispersed in silicone oil were observed using ocular lens: 10× and objective lens: 10× under crossed polarizers, and recorded by camera/computer system with magnification scale.

Example 1. 4-(1-{[4-(4-Trifluoromethyl-benzyl)-4H-thieno[3,2-b]pyrrole-3-carbonyl]-amino}-cyclopropyl)-benzoic acid (C-002)

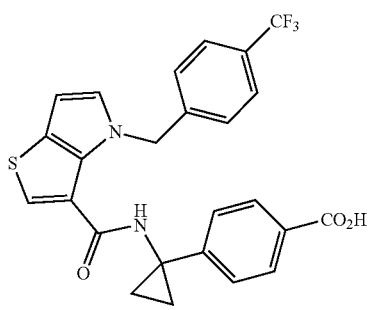 [SMILES: O=C(O)c1ccc(C2(NC(=O)c3csc4ccn(Cc5ccc(C(F)(F)F)cc5)c34)CC2)cc1]

A mixture of 0.33 g of 4-(4-Trifluoromethyl-benzyl)-4H-thieno[3,2-b]pyrrole-3-carboxylic acid, 0.23 g of 4-(1-amino-cyclopropyl)-benzoic acid methyl ester, 0.5 g of HATU and 0.25 mL of Pr$_2$NEt in 8 mL of DMF was stirred at room temperature for 16 h. The reaction was then diluted with 30 mL of water and extracted with 100 mL of EtOAc. The organic layer was washed with 50 mL of water and 50 mL of brine and dried over Na2SO4. The extract was filtered, and concentrated to give the crude methyl ester which was dissolved in 20 mL of 1:1 THF/MeOH and treated with 10 mL of 0.5 N aqueous LiOH solution. After stirring for 15 h at room temperature, 1 mL of AcOH was added and the reaction mixture was extracted with 75 mL of EtOAc. The organic layer was washed with 50 mL of brine, dried over Na$_2$SO$_4$. The extract was filtered and concentrated to give 0.22 g of the title compound as a light brown solid. $^1$H NMR (500 MHz, acetone-d$_6$): δ 11.03 (bs, 1H), 8.49 (s, 1H), 7.40 (d, 2H), 7.83 (s, 1H), 7.57 (d, 2H), 7.32 (d, 2H), 7.23 (d, 1H), 7.19 (d, 2H), 6.51 (d, 1H), 5.35 (s, 2H), 1.35 (m, 2H), 1.32 (m, 2H).

Example 2. 4-(1-{[2-Methyl-4-(4-trifluoromethyl-benzyl)-4H-thieno[3,2-b]pyrrole-3-carbonyl]-amino}-cyclopropyl)-benzoic acid (C-003)

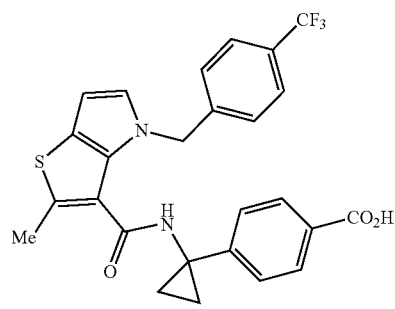 [SMILES: Cc1sc2ccn(Cc3ccc(C(F)(F)F)cc3)c2c1C(=O)NC1(c2ccc(C(=O)O)cc2)CC1]

A mixture of 0.3 g of 2-methyl-4-(4-trifluoromethyl-benzyl)-4H-thieno[3,2-b]pyrrole-3-carboxylic acid, 0.25 g of 4-(1-amino-cyclopropyl)-benzoic acid methyl ester, 0.5 g of HATU and 0.25 mL of Pr$_2$NEt in 8 mL of DMF was stirred at room temperature for 16 h. The reaction was then diluted with 30 mL of water and extracted with 100 mL of EtOAc. The organic layer was washed with 50 mL of water and 50 mL of brine and dried over Na$_2$SO$_4$. The extract was filtered, and concentrated to give the crude methyl ester which was dissolved in 20 mL of 1:1 THF/MeOH and treated with 10 mL of 0.5 M aqueous LiOH solution. After stirring for 15 h at room temperature, 1 mL of AcOH was added and the reaction mixture was extracted with 75 mL of EtOAc. The organic layer was washed with 50 mL of brine, dried over Na$_2$SO$_4$. The extract was filtered and concentrated to give 0.25 g of the title compound as a light brown solid. $^1$H NMR (500 MHz, acetone-d$_6$): δ 11.12 (bs, 1H), 8.17 (s, 1H), 7.85 (d, 2H), 7.57 (d, 2H), 7.35 (d, 2H), 7.11 (d, 2H), 7.05 (d, 1H), 6.42 (d, 1H), 5.58 (s, 2H), 2.62 (s, 3H), 1.31 (m, 2H), 1.20 (m, 2H).

Solid State Characterization of C003 Free Acid

Figure 2:
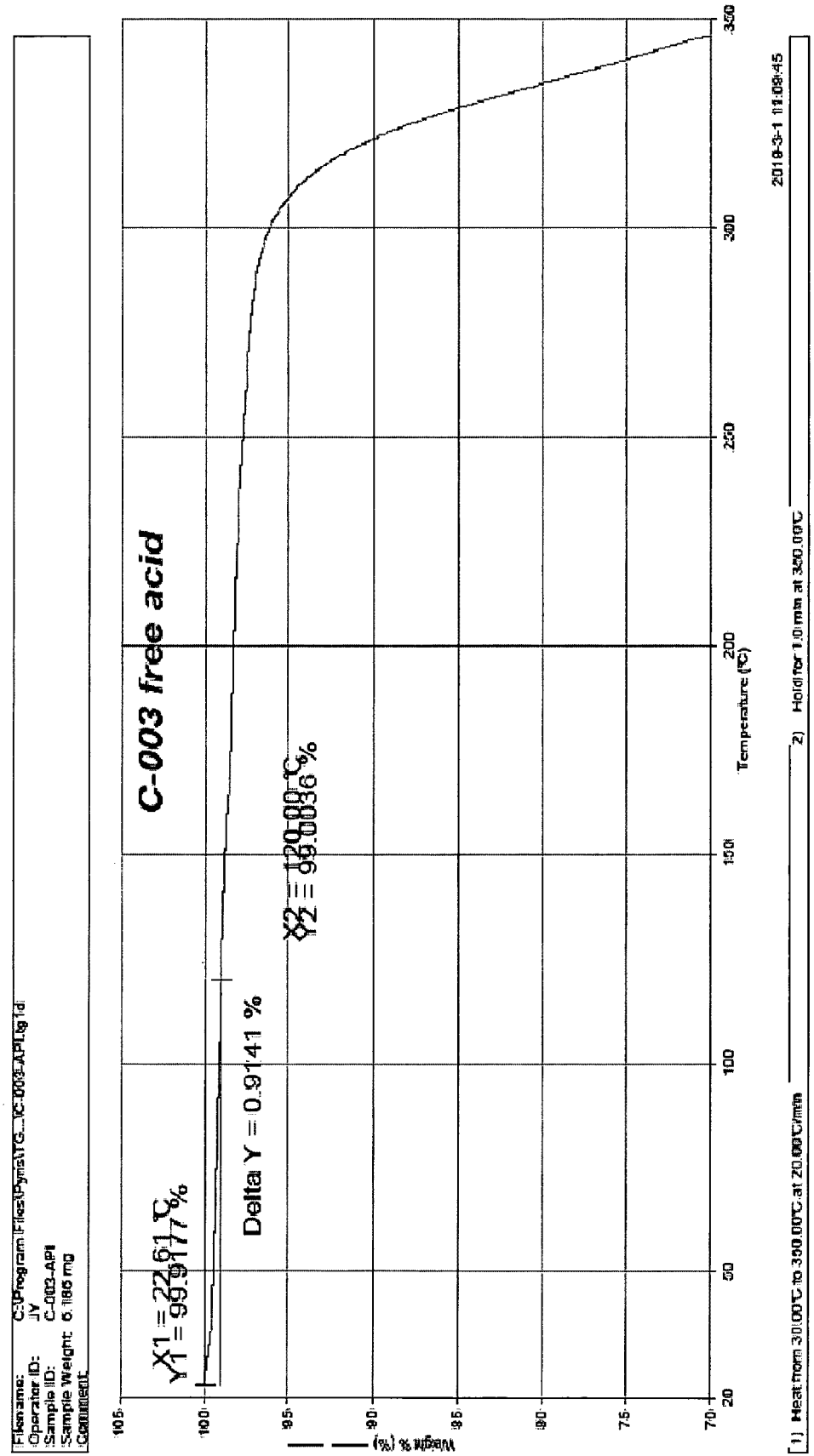
FIG. 2 shows TGA data of C003 free acid.

C003 free acid was characterized by XPRD, TGA, DSC, DVS and PLM. The XRPD, DSC, TGA, DVS and PLM results were showed in Table 1 and FIGS. 1 to 2. The XRPD results showed the compound as a mixture of crystalline and amorphous solids, which was coincident with the PLM result. The TGA results showed the freebase had 0.9% obvious weight loss from room temperature (RT) to 120° C. DVS showed the free base was a hygroscopic with 3.175% moisture at 80% RH.

TABLE 1

| XRPD 2-theta value of C003 free acid | | | | | | | |
|---|---|---|---|---|---|---|---|
| No. | 2-Theta | d(A) | BG | Height | I % | Area | I % | FWHM |
| 1 | 7.86 | 11.24 | 57 | 87 | 18.2 | 2378 | 19.7 | 0.47 |
| 2 | 9.54 | 9.26 | 56 | 188 | 39.3 | 5053 | 41.8 | 0.46 |
| 3 | 11.54 | 7.66 | 55 | 387 | 81 | 10633 | 88 | 0.47 |
| 4 | 14.44 | 6.13 | 107 | 327 | 68.4 | 8146 | 67.4 | 0.42 |
| 5 | 15.38 | 5.76 | 103 | 127 | 26.6 | 2636 | 21.8 | 0.35 |
| 6 | 17.62 | 5.03 | 134 | 146 | 30.5 | 3997 | 33.1 | 0.47 |
| 7 | 18.74 | 4.73 | 188 | 132 | 27.6 | 2440 | 20.2 | 0.31 |
| 8 | 19.56 | 4.53 | 244 | 72 | 15.1 | 968 | 8 | 0.23 |
| 9 | 19.95 | 4.45 | 275 | 65 | 13.6 | 963 | 8 | 0.25 |

TABLE 1-continued

XRPD 2-theta value of C003 free acid

| No. | 2-Theta | d(A) | BG | Height | I % | Area | I % | FWHM |
|---|---|---|---|---|---|---|---|---|
| 10 | 21.18 | 4.19 | 248 | 206 | 43.1 | 7259 | 60.1 | 0.60 |
| 11 | 23.02 | 3.86 | 222 | 478 | 100 | 12078 | 100 | 0.43 |
| 12 | 24.03 | 3.70 | 221 | 73 | 15.3 | 614 | 5.1 | 0.14 |
| 13 | 24.91 | 3.57 | 185 | 49 | 10.3 | 412 | 3.4 | 0.14 |
| 14 | 25.88 | 3.44 | 183 | 107 | 22.4 | 3134 | 25.9 | 0.50 |
| 15 | 26.52 | 3.36 | 193 | 59 | 12.3 | 2578 | 21.3 | 0.74 |
| 16 | 27.68 | 3.22 | 164 | 154 | 32.2 | 3323 | 27.5 | 0.37 |
| 17 | 29.32 | 3.04 | 201 | 127 | 26.6 | 2548 | 21.1 | 0.34 |
| 18 | 30.14 | 2.96 | 105 | 181 | 37.9 | 6346 | 52.5 | 0.60 |
| 19 | 32.26 | 2.77 | 92 | 66 | 13.8 | 2063 | 17.1 | 0.53 |
| 20 | 36.71 | 2.45 | 99 | 49 | 10.3 | 1877 | 15.5 | 0.65 |
| 21 | 39.32 | 2.29 | 98 | 52 | 10.9 | 1041 | 8.6 | 0.34 |
| 22 | 42.09 | 2.15 | 89 | 39 | 8.2 | 595 | 4.9 | 0.26 |
| 23 | 43.64 | 2.07 | 83 | 41 | 8.6 | 1253 | 10.4 | 0.52 |

Preparation of Pharmaceutically Acceptable Salts of Compounds of Formula I

Compounds of Formula I (e.g., those of Examples 1 and 2 described above) can react with a base such as diethylamine, diethanolamine, or tris(hydroxymethyl)aminomethane to prepare pharmaceutically acceptable salts according to methods known in the art.

Example 3. Preparation of C002-Arginine Salt

Compound of Example 1 (100 mg, 0.21 mmol) was added to a flask with EtOH (1.0 mL) to obtain a white suspension. Arginine (43 mg, 0.25 mmol) was added in one portion and the reaction mixture turned clear. After stirring for 30 minutes, a white precipitate was observed. The mixture was further stirred overnight. A white solid was collected to afford the target salt as a white solid (100 mg, at 74% yield). The XRPD data of this salt are listed below in Table 2.

TABLE 2

XRPD 2-theta of C002/Arginine salt

| NO. | Pos.[°2Th.] | Height[cts] | FWHM[°2Th.] | d(A) | Rel.Int.[%] |
|---|---|---|---|---|---|
| 1 | 6.23 | 468 | 0.46 | 14.20 | 19.7 |
| 2 | 7.96 | 849 | 0.41 | 11.10 | 35.8 |
| 3 | 10.99 | 355 | 0.18 | 8.05 | 15.0 |
| 4 | 14.76 | 903 | 0.36 | 6.00 | 38.1 |
| 5 | 15.97 | 1292 | 0.46 | 5.55 | 54.5 |
| 6 | 18.29 | 1932 | 0.15 | 4.85 | 81.5 |
| 7 | 19.05 | 1625 | 0.15 | 4.66 | 68.6 |
| 8 | 19.36 | 2197 | 0.18 | 4.58 | 92.7 |
| 9 | 20.46 | 996 | 0.31 | 4.34 | 42.0 |
| 10 | 21.40 | 672 | 0.41 | 4.15 | 28.4 |
| 11 | 23.05 | 2371 | 0.18 | 3.86 | 100.0 |
| 12 | 27.35 | 1072 | 0.18 | 3.26 | 45.2 |
| 13 | 28.17 | 353 | 0.26 | 3.17 | 14.9 |
| 14 | 29.80 | 241 | 0.51 | 3.00 | 10.2 |
| 15 | 34.13 | 85 | 0.31 | 2.63 | 3.6 |

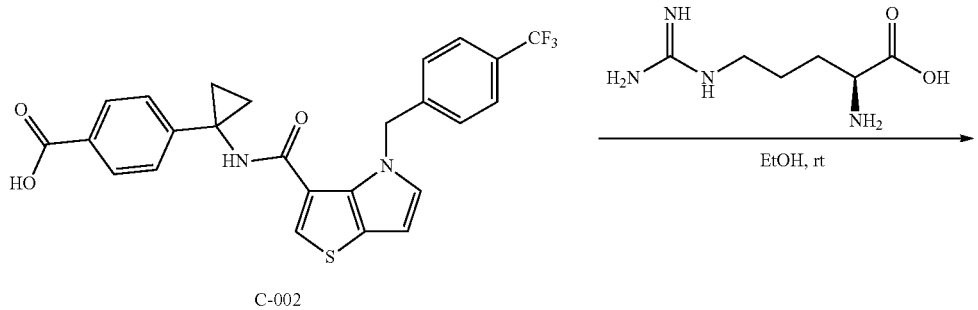

Scheme 1

C-002

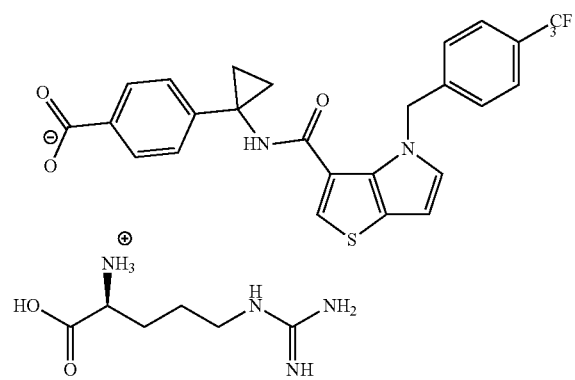

Example 4. Preparation of C002-Dihydroxylethylamine Salt

Scheme 2

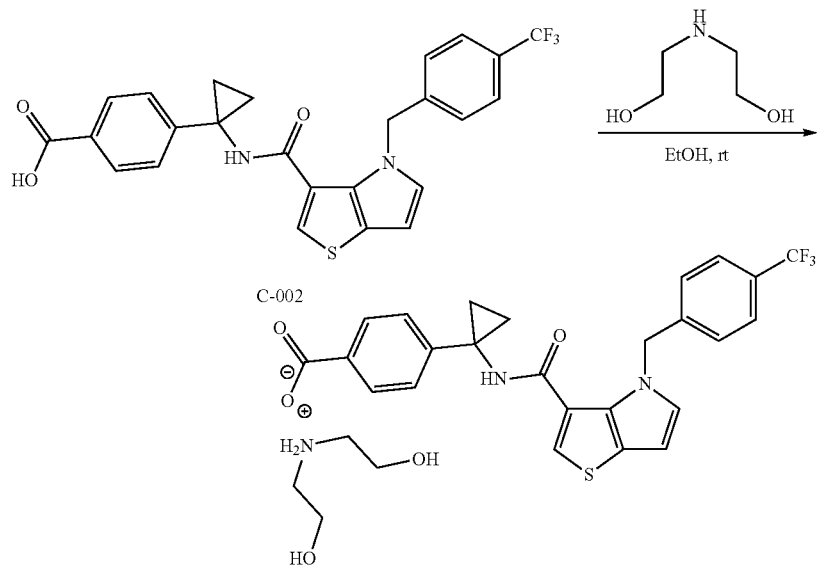

Compound of Example 1 (55 mg, 0.114 mmol) was added to a flask with EtOH (2.0 ml) to result in white suspension. Diethanolamine (14 mg, 0.136 mmol) was added in one portion and the reaction mixture turned clear. After stirring for 30 minutes, a white precipitate was observed. After further stirring overnight, a white solid was collected to afford the salt as a white solid (47 mg, 70% yield). The XRPD data of this salt are listed below in Table 3.

TABLE 3

XRPD 2-theta of C002/diethanolamine salt

| NO. | Pos.[°2Th.] | Height[cts] | FWHM[°2Th.] | d(A) | Rel.Int.[%] |
|---|---|---|---|---|---|
| 1 | 3.79 | 593 | 0.15 | 23.34 | 8.3 |
| 2 | 7.57 | 1308 | 0.23 | 11.68 | 18.4 |
| 3 | 8.22 | 1369 | 0.20 | 10.76 | 19.3 |
| 4 | 9.23 | 865 | 0.13 | 9.58 | 12.2 |
| 5 | 10.52 | 202 | 0.20 | 8.41 | 2.9 |
| 6 | 11.95 | 166 | 0.20 | 7.40 | 2.3 |
| 7 | 13.59 | 1334 | 0.18 | 6.52 | 18.8 |
| 8 | 14.64 | 708 | 0.13 | 6.05 | 10.0 |
| 9 | 15.26 | 1718 | 0.20 | 5.81 | 24.2 |

TABLE 3-continued

XRPD 2-theta of C002/diethanolamine salt

| NO. | Pos.[°2Th.] | Height[cts] | FWHM[°2Th.] | d(A) | Rel.Int.[%] |
|---|---|---|---|---|---|
| 10 | 16.49 | 7107 | 0.23 | 5.38 | 100.0 |
| 11 | 17.45 | 1485 | 0.15 | 5.08 | 20.9 |
| 12 | 17.89 | 1179 | 0.18 | 4.96 | 16.6 |
| 13 | 18.68 | 1799 | 0.23 | 4.75 | 25.3 |
| 14 | 19.29 | 1187 | 0.20 | 4.60 | 16.7 |
| 15 | 20.22 | 2876 | 0.23 | 4.39 | 40.5 |
| 16 | 21.52 | 1178 | 0.15 | 4.13 | 16.6 |
| 17 | 22.33 | 1044 | 0.15 | 3.98 | 14.7 |
| 18 | 23.13 | 5086 | 0.26 | 3.85 | 71.6 |
| 19 | 24.15 | 1824 | 0.26 | 3.69 | 25.7 |
| 20 | 25.00 | 1264 | 0.41 | 3.56 | 17.8 |
| 21 | 25.76 | 1120 | 0.15 | 3.46 | 15.8 |
| 22 | 26.86 | 896 | 0.26 | 3.32 | 12.6 |
| 23 | 27.82 | 1453 | 0.15 | 3.21 | 20.4 |
| 24 | 28.99 | 1085 | 0.26 | 3.08 | 15.3 |

Example 5. Preparation of C002-1,1,1-Tris(Hydroxymethyl)-Methylamine Salt

Scheme 3

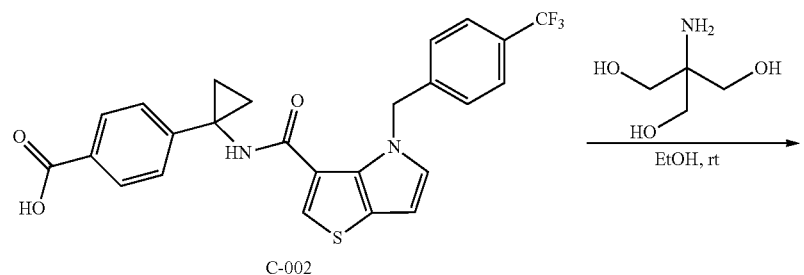

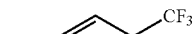
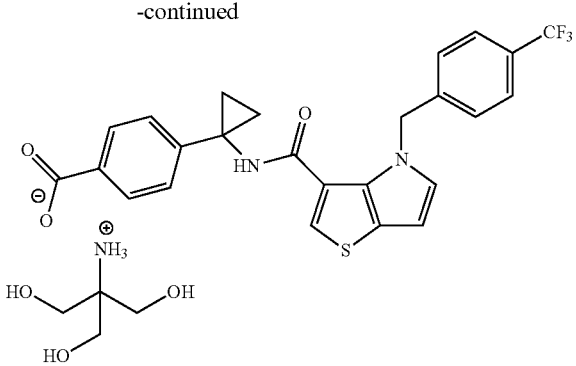

Compound of Example 1 (200 mg, 0.41 mmol) was added to a flask with EtOH (4.0 mL) to result in a white suspension. 1,1,1-Tris(Hydroxymethyl)-methylamine base (60 mg, 0.50 mmol) was added in one portion and the reaction mixture turned clear. After stirring for 30 mins, a white precipitate was observed. After further stirring overnight, a white solid was collected to afford the target salt as a white solid (215 mg, 86% yield). The XRPD data of this salt are listed below in Table 4.

TABLE 4

XRPD 2-theta of C002/1,1,1-Tris(Hydroxymethyl)-Methylamine salt

| NO. | Pos.[°2Th.] | Height[cts] | FWHM[°2Th.] | d(A) | Rel.Int.[%] |
|---|---|---|---|---|---|
| 1 | 5.63 | 6188 | 0.15 | 15.69 | 34.2 |
| 2 | 8.45 | 18112 | 0.18 | 10.46 | 100.0 |
| 3 | 9.04 | 6321 | 0.23 | 9.78 | 34.9 |
| 4 | 11.30 | 2776 | 0.20 | 7.83 | 15.3 |
| 5 | 12.54 | 857 | 0.15 | 7.06 | 4.7 |
| 6 | 13.11 | 746 | 0.20 | 6.76 | 4.1 |
| 7 | 14.12 | 4868 | 0.23 | 6.27 | 26.9 |
| 8 | 14.62 | 1762 | 0.18 | 6.06 | 9.7 |
| 9 | 15.69 | 3485 | 0.28 | 5.65 | 19.2 |
| 10 | 16.25 | 565 | 0.15 | 5.45 | 3.1 |
| 11 | 16.97 | 1366 | 0.18 | 5.22 | 7.5 |
| 12 | 17.51 | 3782 | 0.26 | 5.06 | 20.9 |
| 13 | 18.26 | 3733 | 0.28 | 4.86 | 20.6 |
| 14 | 18.79 | 992 | 0.20 | 4.72 | 5.5 |
| 15 | 19.63 | 3411 | 0.26 | 4.52 | 18.8 |
| 16 | 20.13 | 2975 | 0.18 | 4.41 | 16.4 |
| 17 | 20.57 | 2291 | 0.23 | 4.32 | 12.7 |
| 18 | 21.55 | 2263 | 0.15 | 4.12 | 12.5 |
| 19 | 22.05 | 5084 | 0.26 | 4.03 | 28.1 |
| 20 | 22.59 | 1519 | 0.15 | 3.94 | 8.4 |
| 21 | 23.70 | 1081 | 0.18 | 3.75 | 6.0 |
| 22 | 24.36 | 1589 | 0.28 | 3.65 | 8.8 |
| 23 | 25.59 | 1909 | 0.26 | 3.48 | 10.5 |
| 24 | 26.37 | 1003 | 0.10 | 3.38 | 5.5 |
| 25 | 27.68 | 675 | 0.18 | 3.22 | 3.7 |

Example 6. Preparation of C002-Diethylamine Salt

Scheme 4

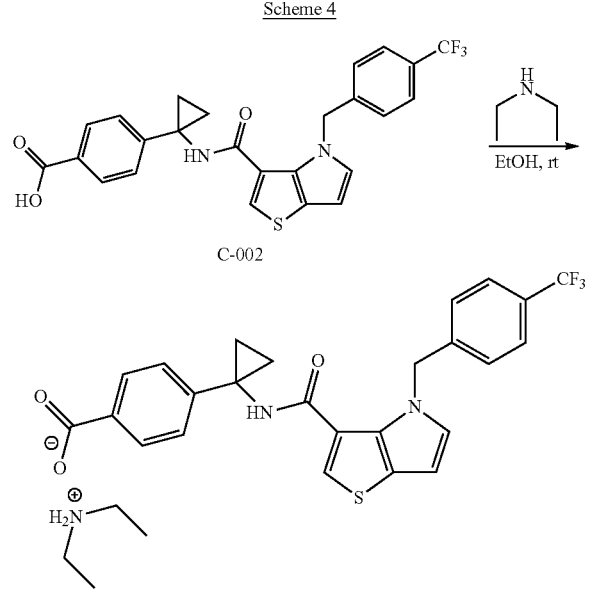

C-002 (200 mg, 0.40 mmol) was added to a flask with EtOH (2.0 mL) to get a white suspension. Diethylamine (38 mg, 0.5 mmol) was added in one portion. The reaction turned clear. After stirred for 30 mins, a white precipitate appeared and reaction was stirred overnight. The white solid was collected to afford the target compound as a white solid (180 mg, 80% yield). The XRPD data of this compound are listed in Table 5.

TABLE 5

XRPD 2-theta of C002/diethylamine salt

| NO. | Pos.[°2Th.] | Height[cts] | FWHM[°2Th.] | D(A) | Rel.Int.[%] |
|---|---|---|---|---|---|
| 1 | 3.82 | 1595 | 0.18 | 23.11 | 50.8 |
| 2 | 7.59 | 619 | 0.15 | 11.66 | 19.7 |
| 3 | 8.28 | 650 | 0.23 | 10.67 | 20.7 |
| 4 | 9.31 | 169 | 0.31 | 9.50 | 5.4 |
| 5 | 12.11 | 136 | 0.31 | 7.31 | 4.3 |
| 6 | 13.78 | 730 | 0.23 | 6.42 | 23.2 |
| 7 | 14.74 | 524 | 0.20 | 6.01 | 16.7 |
| 8 | 15.34 | 1341 | 0.20 | 5.78 | 42.7 |
| 9 | 16.69 | 2480 | 0.26 | 5.31 | 79.0 |
| 10 | 17.76 | 1680 | 0.26 | 4.99 | 53.5 |

TABLE 5-continued

| XRPD 2-theta of C002/diethylamine salt | | | | |
|---|---|---|---|---|
| NO. | Pos.[°2Th.] | Height[cts] | FWHM[°2Th.] | D(A) | Rel.Int.[%] |
| 11 | 18.62 | 823 | 0.15 | 4.76 | 26.2 |
| 12 | 19.30 | 900 | 0.18 | 4.60 | 28.7 |
| 13 | 20.17 | 2965 | 0.31 | 4.40 | 94.4 |
| 14 | 21.53 | 1019 | 0.20 | 4.13 | 32.5 |
| 15 | 23.16 | 3141 | 0.23 | 3.84 | 100.0 |
| 16 | 24.42 | 1510 | 0.23 | 3.65 | 48.1 |
| 17 | 25.95 | 772 | 0.31 | 3.43 | 24.6 |
| 18 | 27.93 | 612 | 0.36 | 3.20 | 19.5 |
| 19 | 30.41 | 385 | 0.31 | 2.94 | 12.2 |
| 20 | 36.76 | 78 | 0.31 | 2.44 | 2.5 |

Example 7. Preparation of C003-Sodium Salt

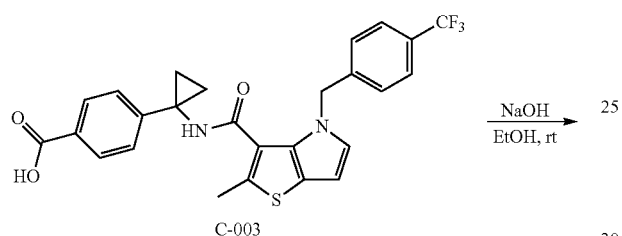

Scheme 5

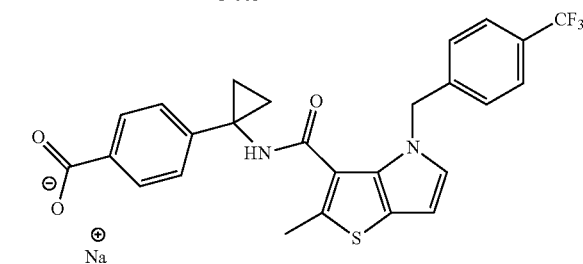

About 50 mg of C003 free acid was weighed and put into a glass vial, and then it was dissolved by 1 mL ethanol with sonication. Afterwards, 26 μl of sodium hydroxide solution (4 mol/L in water) was added into the vial by drop wise. The sample was kept stirring for 24 h on a magnetic stirrer at room temperature. After stirring for 24 hrs, the solid precipitation of suspensions was isolated by centrifugation method, and further dried under condition of low pressure at 40° C. for a few hours. If needed, the dried solid was re-crystallized in isopropyl alcohol:water (9:1). For example: About 150 mg of C003-sodium salt was suspended in 5 mL of isopropyl alcohol:water (9:1) for 24 hrs. The solid precipitation was isolated by centrifugation method and further dried in vacuum oven at 80° C. for a few hours. The XRPD data of this salt are provided in Table 6 below.

TABLE 6

| XRPD 2-theta of C003-Na-salt | | | | | | | |
|---|---|---|---|---|---|---|---|
| No. | 2-Theta | d(A) | BG | Height | I % | Area | I % | FWHM |
| 1 | 6.84 | 12.92 | 68 | 132 | 24.7 | 1947 | 18.7 | 0.25 |
| 2 | 9.30 | 9.50 | 66 | 354 | 66.2 | 10405 | 100 | 0.50 |
| 3 | 9.95 | 8.88 | 78 | 42 | 7.9 | 234 | 2.2 | 0.10 |
| 4 | 11.50 | 7.69 | 66 | 332 | 62.1 | 5810 | 55.8 | 0.30 |
| 5 | 13.84 | 6.39 | 128 | 218 | 40.7 | 3593 | 34.5 | 0.28 |

TABLE 6-continued

| XRPD 2-theta of C003-Na-salt | | | | | | | |
|---|---|---|---|---|---|---|---|
| No. | 2-Theta | d(A) | BG | Height | I % | Area | I % | FWHM |
| 6 | 14.80 | 5.98 | 137 | 535 | 100 | 8995 | 86.4 | 0.29 |
| 7 | 15.60 | 5.68 | 126 | 74 | 13.8 | 695 | 6.7 | 0.16 |
| 8 | 16.36 | 5.41 | 117 | 405 | 75.7 | 6577 | 63.2 | 0.28 |
| 9 | 17.24 | 5.14 | 108 | 46 | 8.6 | 263 | 2.5 | 0.10 |
| 10 | 18.20 | 4.87 | 145 | 221 | 41.3 | 5009 | 48.1 | 0.39 |
| 11 | 18.75 | 4.73 | 175 | 49 | 9.2 | 1026 | 9.9 | 0.36 |
| 12 | 19.44 | 4.56 | 198 | 158 | 29.5 | 3347 | 32.2 | 0.36 |
| 13 | 19.88 | 4.46 | 205 | 109 | 20.4 | 2974 | 28.6 | 0.46 |
| 14 | 21.02 | 4.22 | 215 | 111 | 20.7 | 3584 | 34.4 | 0.55 |
| 15 | 21.80 | 4.07 | 202 | 166 | 31 | 2124 | 20.4 | 0.22 |
| 16 | 22.60 | 3.93 | 182 | 114 | 21.3 | 2663 | 25.6 | 0.40 |
| 17 | 23.04 | 3.86 | 173 | 79 | 14.8 | 2466 | 23.7 | 0.53 |
| 18 | 24.70 | 3.60 | 167 | 127 | 23.7 | 3380 | 32.5 | 0.45 |
| 19 | 26.58 | 3.35 | 175 | 83 | 15.5 | 1477 | 14.2 | 0.30 |
| 20 | 27.70 | 3.22 | 167 | 53 | 9.9 | 503 | 4.8 | 0.16 |
| 21 | 28.51 | 3.13 | 150 | 68 | 12.7 | 2100 | 20.2 | 0.53 |
| 22 | 29.87 | 2.99 | 154 | 46 | 8.6 | 244 | 2.3 | 0.09 |
| 23 | 30.72 | 2.91 | 140 | 68 | 12.7 | 497 | 4.8 | 0.12 |
| 24 | 31.84 | 2.81 | 128 | 62 | 11.6 | 1338 | 12.9 | 0.37 |

Example 8. Preparation of C003-Magnesium Salt

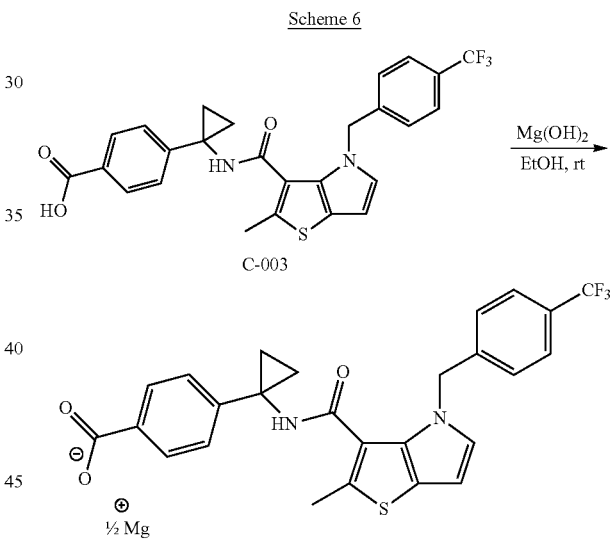

Scheme 6

About 50 mg of C003 free acid was weighed and put into a glass vial, and then it was dissolved by 1 mL ethanol with sonication. Afterwards, 6.21 mg of magnesium hydroxide was added into the vial. The sample was kept stirring for 24 hrs on a magnetic stirrer at room temperature. After stirring for 24 hrs, the solid precipitation of suspensions was isolated by centrifugation method, and further dried under condition of low pressure at 40° C. for a few hours to give the target salt. The XRPD data of this salt are provide in Table 7 below.

TABLE 7

| XRPD 2-theta of C003-Mg-salt | | | | | | | |
|---|---|---|---|---|---|---|---|
| NO. | 2-Theta | d(A) | BG | Height | I % | Area | I % | FWHM |
| 1 | 7.60 | 11.62 | 61 | 217 | 22.5 | 3950 | 20.5 | 0.31 |
| 2 | 9.30 | 9.50 | 58 | 146 | 15.2 | 3192 | 16.6 | 0.37 |
| 3 | 11.40 | 7.76 | 56 | 352 | 36.6 | 7538 | 39.2 | 0.36 |

TABLE 7-continued

XRPD 2-theta of C003-Mg-salt

| NO. | 2-Theta | d(A) | BG | Height | I % | Area | I % | FWHM |
|---|---|---|---|---|---|---|---|---|
| 4 | 14.26 | 6.21 | 97 | 659 | 68.4 | 12522 | 65 | 0.32 |
| 5 | 15.26 | 5.80 | 97 | 315 | 32.7 | 5854 | 30.4 | 0.32 |
| 6 | 17.42 | 5.09 | 90 | 344 | 35.7 | 7272 | 37.8 | 0.36 |
| 7 | 18.58 | 4.77 | 115 | 963 | 100 | 19254 | 100 | 0.34 |
| 8 | 19.16 | 4.63 | 149 | 81 | 8.4 | 1031 | 5.4 | 0.22 |
| 9 | 20.90 | 4.25 | 121 | 831 | 86.3 | 18111 | 94.1 | 0.37 |
| 10 | 22.84 | 3.89 | 113 | 259 | 26.9 | 5183 | 26.9 | 0.34 |
| 11 | 23.88 | 3.72 | 119 | 89 | 9.2 | 1224 | 6.4 | 0.23 |
| 12 | 24.58 | 3.62 | 113 | 147 | 15.3 | 2790 | 14.5 | 0.32 |
| 13 | 25.66 | 3.47 | 121 | 167 | 17.3 | 2907 | 15.1 | 0.30 |
| 14 | 26.66 | 3.34 | 137 | 43 | 4.5 | 571 | 3 | 0.23 |
| 15 | 27.54 | 3.24 | 124 | 106 | 11 | 1254 | 6.5 | 0.20 |
| 16 | 29.16 | 3.06 | 117 | 101 | 10.5 | 2097 | 10.9 | 0.35 |
| 17 | 29.98 | 2.98 | 117 | 143 | 14.8 | 3276 | 17 | 0.39 |
| 18 | 32.04 | 2.79 | 74 | 152 | 15.8 | 3676 | 19.1 | 0.41 |
| 19 | 34.86 | 2.57 | 75 | 57 | 5.9 | 1541 | 8 | 0.46 |
| 20 | 36.85 | 2.44 | 79 | 65 | 6.7 | 1088 | 5.7 | 0.29 |
| 21 | 38.02 | 2.36 | 73 | 417 | 43.3 | 8396 | 43.6 | 0.34 |
| 22 | 41.47 | 2.18 | 64 | 34 | 3.5 | 680 | 3.5 | 0.34 |
| 23 | 42.04 | 2.15 | 63 | 41 | 4.3 | 943 | 4.9 | 0.39 |

Example 9. Preparation of C003-Calcium Salt

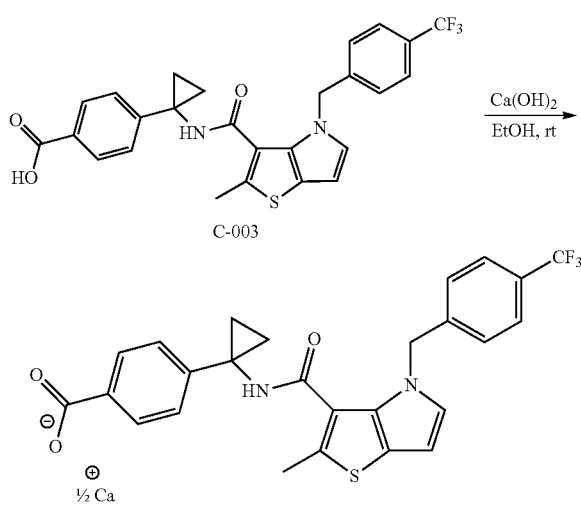

Scheme 7

About 50 mg of C0003 free acid was weighed and put into a glass vial, and then it was dissolved by 1 mL ethanol with sonication. Afterwards, 8.22 mg of calcium hydroxide was added into the vial. The sample was kept stirring for 24 hrs on a magnetic stirrer at room temperature. After stirring for 24 hrs, the solid precipitation of suspensions was isolated by centrifugation method, and further dried under condition of low pressure at 40° C. for a few hours, to give the target salt. The XRPD data of this salt are provided below in Table 8.

TABLE 8

XRPD 2-theta value of C003-Ca-salt

| NO. | 2-Theta | d(A) | BG | Height | I % | Area | I % | FWHM |
|---|---|---|---|---|---|---|---|---|
| 1 | 5.56 | 15.88 | 81 | 57 | 11.9 | 891 | 8.4 | 0.27 |
| 2 | 7.84 | 11.27 | 65 | 57 | 11.9 | 898 | 8.4 | 0.27 |
| 3 | 8.80 | 10.04 | 63 | 79 | 16.4 | 2389 | 22.4 | 0.51 |
| 4 | 9.48 | 9.32 | 71 | 35 | 7.3 | 204 | 1.9 | 0.10 |
| 5 | 11.58 | 7.64 | 56 | 198 | 41.2 | 5423 | 50.9 | 0.47 |
| 6 | 14.40 | 6.15 | 77 | 163 | 33.9 | 3470 | 32.6 | 0.36 |
| 7 | 15.48 | 5.72 | 92 | 118 | 24.5 | 2290 | 21.5 | 0.33 |
| 8 | 17.58 | 5.04 | 116 | 80 | 16.6 | 507 | 4.8 | 0.11 |
| 9 | 18.20 | 4.87 | 103 | 481 | 100 | 10654 | 100 | 0.38 |
| 10 | 19.38 | 4.58 | 98 | 36 | 7.5 | 484 | 4.5 | 0.23 |
| 11 | 21.04 | 4.22 | 118 | 192 | 39.9 | 4764 | 44.7 | 0.42 |
| 12 | 22.98 | 3.87 | 101 | 111 | 23.1 | 1963 | 18.4 | 0.30 |
| 13 | 24.04 | 3.70 | 87 | 51 | 10.6 | 430 | 4 | 0.14 |
| 14 | 25.90 | 3.44 | 93 | 53 | 11 | 608 | 5.7 | 0.20 |
| 15 | 27.69 | 3.22 | 89 | 59 | 12.3 | 1135 | 10.7 | 0.33 |
| 16 | 28.86 | 3.09 | 91 | 53 | 11 | 1361 | 12.8 | 0.44 |
| 17 | 32.25 | 2.77 | 56 | 50 | 10.4 | 824 | 7.7 | 0.28 |
| 18 | 34.18 | 2.62 | 58 | 352 | 73.2 | 8260 | 77.5 | 0.40 |
| 19 | 43.62 | 2.07 | 51 | 29 | 6 | 359 | 3.4 | 0.21 |
| 20 | 47.28 | 1.92 | 54 | 174 | 36.2 | 4359 | 40.9 | 0.43 |

Example 10. Preparation of C003-Ammonium Salt

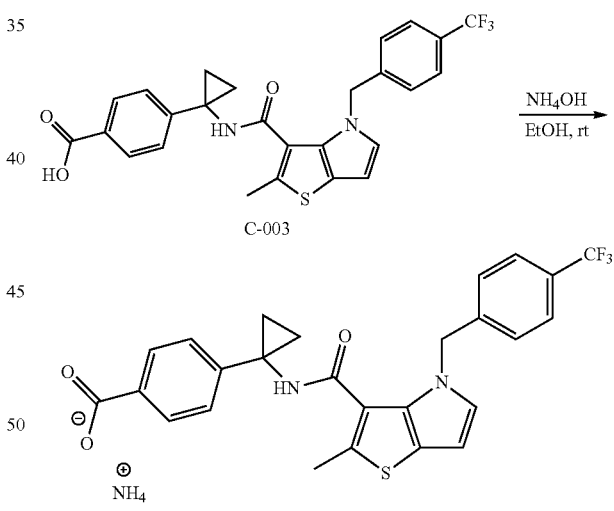

Scheme 8

About 200 mg of C003 free acid was weighed out and put into a glass vial, and then it was dissolved by 10 mL of acetone. Afterwards, 211 μl of ammonium hydroxide solution (2 mol/L in water) was added into the vial by drop wise at 60'C. When the counter-ion was added, some brown precipitation was observed. The sample was kept stirring for 16 hrs on a magnetic stirrer at 40° C. and continued stirring in ice-water bath for 6 hrs. After that the solid precipitation was isolated by centrifugation method, and further dried under reducing pressure condition at 40° C. for a few hours to give rise to the target salt. The XRPD data are provided below in Table 9.

TABLE 9

XRPD 2-theta value of C003/NH4OH

| NO. | 2-Theta | d(A) | BG | Height | I % | Area | I % | FWHM |
|---|---|---|---|---|---|---|---|---|
| 1 | 7.12 | 12.40 | 79 | 83 | 15.5 | 921 | 5.5 | 0.19 |
| 2 | 7.88 | 11.21 | 70 | 138 | 25.8 | 1914 | 11.4 | 0.24 |
| 3 | 8.96 | 9.86 | 71 | 147 | 27.5 | 2499 | 14.9 | 0.29 |
| 4 | 9.55 | 9.26 | 83 | 103 | 19.3 | 1025 | 6.1 | 0.17 |
| 5 | 10.00 | 8.84 | 76 | 58 | 10.9 | 436 | 2.6 | 0.13 |
| 6 | 10.28 | 8.60 | 74 | 64 | 12 | 309 | 1.8 | 0.08 |
| 7 | 11.39 | 7.77 | 66 | 64 | 12 | 1376 | 8.2 | 0.37 |
| 8 | 11.80 | 7.49 | 65 | 121 | 22.7 | 2109 | 12.6 | 0.30 |
| 9 | 13.40 | 6.60 | 76 | 208 | 39 | 4758 | 28.4 | 0.39 |
| 10 | 13.92 | 6.36 | 115 | 391 | 73.2 | 8732 | 52.2 | 0.38 |
| 11 | 14.36 | 6.16 | 176 | 100 | 18.7 | 808 | 4.8 | 0.14 |
| 12 | 14.98 | 5.91 | 128 | 286 | 53.6 | 4498 | 26.9 | 0.27 |
| 13 | 16.10 | 5.50 | 163 | 61 | 11.4 | 971 | 5.8 | 0.27 |
| 14 | 16.76 | 5.29 | 154 | 534 | 100 | 8406 | 50.3 | 0.27 |
| 15 | 18.00 | 4.92 | 137 | 285 | 53.4 | 4741 | 28.3 | 0.28 |
| 16 | 18.54 | 4.78 | 211 | 417 | 78.1 | 16726 | 100 | 0.68 |
| 17 | 19.18 | 4.62 | 271 | 183 | 34.3 | 6284 | 37.6 | 0.58 |
| 18 | 20.32 | 4.37 | 256 | 146 | 27.3 | 2758 | 16.5 | 0.32 |
| 19 | 21.54 | 4.12 | 281 | 95 | 17.8 | 729 | 4.4 | 0.13 |
| 20 | 22.10 | 4.02 | 287 | 195 | 36.5 | 5342 | 31.9 | 0.47 |
| 21 | 22.48 | 3.95 | 266 | 186 | 34.8 | 7313 | 43.7 | 0.67 |
| 22 | 22.86 | 3.89 | 258 | 92 | 17.2 | 3400 | 20.3 | 0.63 |
| 23 | 23.87 | 3.73 | 228 | 60 | 11.2 | 525 | 3.1 | 0.15 |
| 24 | 25.24 | 3.53 | 205 | 79 | 14.8 | 3085 | 18.4 | 0.66 |
| 25 | 25.88 | 3.44 | 210 | 138 | 25.8 | 2833 | 16.9 | 0.35 |
| 26 | 27.65 | 3.22 | 190 | 56 | 10.5 | 379 | 2.3 | 0.12 |
| 27 | 27.67 | 3.22 | 167 | 57 | 10.7 | 1573 | 9.4 | 0.47 |
| 28 | 28.24 | 3.16 | 173 | 69 | 12.9 | 1762 | 10.5 | 0.43 |
| 29 | 30.22 | 2.95 | 141 | 65 | 12.2 | 693 | 4.1 | 0.18 |
| 30 | 34.05 | 2.63 | 115 | 41 | 7.7 | 503 | 3 | 0.21 |
| 31 | 35.32 | 2.54 | 111 | 43 | 8.1 | 1549 | 9.3 | 0.61 |
| 32 | 38.74 | 2.32 | 107 | 61 | 11.4 | 1896 | 11.3 | 0.53 |

Example 11. Preparation of C003-Arginine Salt

About 200 mg of C003 free acid was weighed out and put into a glass vial, and then it was dissolved by 10 mL of acetone. Afterwards, 422 µl of L-arginine solution (1 mol/L in water) was added into the vial by drop wise at 60° C. When the counter-ion was added, some brown precipitation was observed. The sample was kept stirring for 24 hrs on a magnetic stirrer at room temperature. The solid precipitation was isolated by centrifugation method, and further dried under reducing pressure condition at 40° C. If needed, the dry solid was re-crystallized in ethanol:water (5:1). For example: about 30 mg of L-arginine-salt was suspended in 1.0 ml of ethanol:water (5:1), and kept stirring overnight. The wet solid was isolated by centrifugation method and further dried in vacuum oven at 60° C. for a few hours. After continued stirring overnight, a white solid was collected to afford the target salt as a white solid (180 mg, 67% yield). The salt's XRPD data are provided in Table 10 below.

TABLE 10

XRPD 2-theta of C003-Arginine-salt

| NO. | 2-Theta | d(A) | BG | Height | I % | Area | I % | FWHM |
|---|---|---|---|---|---|---|---|---|
| 1 | 7.66 | 11.53 | 65.00 | 59 | 32.8 | 1110 | 20.6 | 0.32 |
| 2 | 9.29 | 9.51 | 76.00 | 60 | 33.3 | 1596 | 29.6 | 0.45 |
| 3 | 10.10 | 8.75 | 77.00 | 51 | 28.3 | 830 | 15.4 | 0.28 |
| 4 | 12.10 | 7.31 | 67.00 | 51 | 28.3 | 1138 | 21.1 | 0.38 |
| 5 | 13.86 | 6.38 | 101.00 | 125 | 69.4 | 3557 | 66 | 0.48 |
| 6 | 14.31 | 6.18 | 113.00 | 39 | 21.7 | 1462 | 27.1 | 0.64 |
| 7 | 15.18 | 5.83 | 115.00 | 131 | 72.8 | 5343 | 99.2 | 0.69 |
| 8 | 15.60 | 5.68 | 116.00 | 154 | 85.6 | 5336 | 99.1 | 0.59 |
| 9 | 19.90 | 4.46 | 252.00 | 180 | 100 | 5387 | 100 | 0.51 |
| 10 | 20.86 | 4.25 | 240.00 | 78 | 43.3 | 568 | 10.5 | 0.12 |
| 11 | 22.28 | 3.99 | 190.00 | 136 | 75.6 | 4058 | 75.3 | 0.51 |
| 12 | 22.56 | 3.94 | 198.00 | 104 | 57.8 | 3693 | 68.6 | 0.60 |
| 13 | 24.84 | 3.58 | 190.00 | 56 | 31.1 | 1858 | 34.5 | 0.56 |

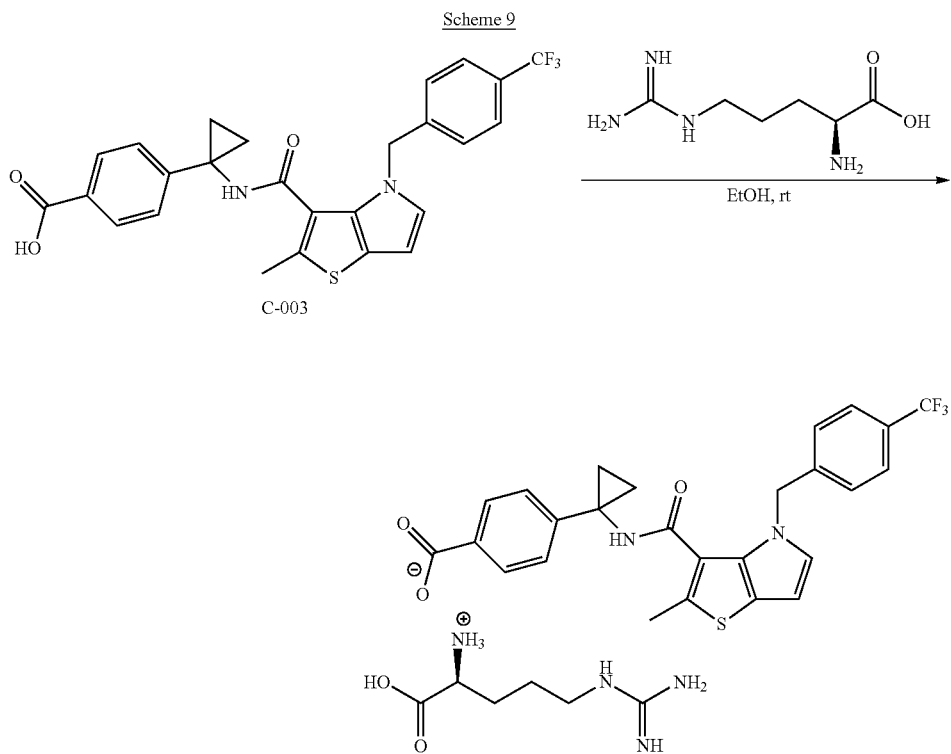

TABLE 10-continued

| XRPD 2-theta of C003-Arginine-salt |||||||||
| NO. | 2-Theta | d(A) | BG | Height | I % | Area | I % | FWHM |
| --- | --- | --- | --- | --- | --- | --- | --- | --- |
| 14 | 25.26 | 3.52 | 186.00 | 86 | 47.8 | 1973 | 36.6 | 0.39 |
| 15 | 30.64 | 2.92 | 125.00 | 83 | 46.1 | 1420 | 26.4 | 0.29 |
| 16 | 31.92 | 2.80 | 113.00 | 39 | 21.7 | 643 | 11.9 | 0.28 |

Example 12. Preparation of C003-Lysine Salt

Scheme 10

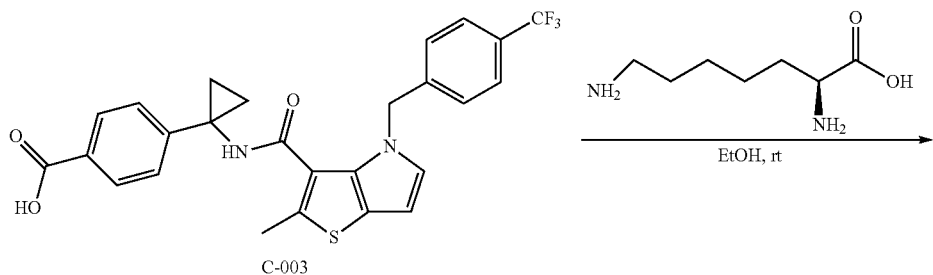

About 200 mg of C003 free acid was weighed out and put into a glass vial, and then it was dissolved by 10 mL of acetone. Afterwards, 422 µl of L-lysine solution (1 mol/L in water) was added into the vial by drop wise at 60° C. When the counter-ion was added, some brown precipitation was observed. The sample was kept stirring for 16 hrs at 40° C. at first and 50° C. for 6 hrs. After that, the sample was continued stirring for 16 hrs at room temperature and brown precipitation was still observed. The solid precipitation was isolated by centrifugation method, and further dried under reducing pressure condition at 40° C. If needed, the dry solid was re-crystallized in ethanol:water (5:1). For example: About 30 mg of L-lysine-salt was suspended in 1.0 ml of ethanol:water (5:1), and kept stirring overnight. The wet solid was isolated by centrifugation method and further dried in vacuum oven at 60° C. for a few hours to give rise to the target salt. This salt's XRPD data are provided below in Table 11.

TABLE 11

| XRPD 2-theta value of C003-L-lysine-salt |||||||||
| NO. | 2-Theta | d(A) | BG | Height | I % | Area | I % | FWHM |
| --- | --- | --- | --- | --- | --- | --- | --- | --- |
| 1 | 8.08 | 10.94 | 73 | 71 | 25.3 | 1293 | 12.7 | 0.31 |
| 2 | 9.00 | 9.82 | 72 | 134 | 47.7 | 2825 | 27.8 | 0.36 |
| 3 | 10.72 | 8.25 | 55 | 67 | 23.8 | 1638 | 16.1 | 0.42 |
| 4 | 12.40 | 7.13 | 60 | 56 | 19.9 | 1190 | 11.7 | 0.36 |

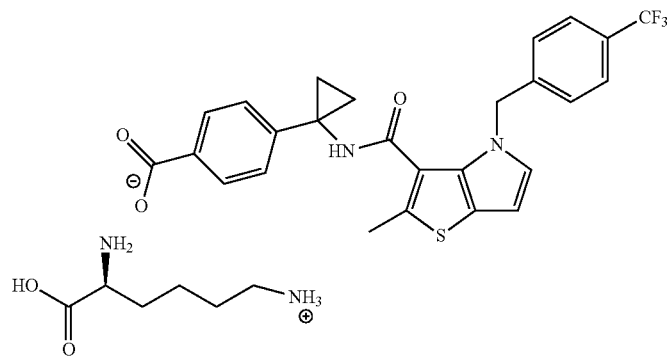

TABLE 11-continued

| XRPD 2-theta value of C003-L-lysine-salt |||||||||
| NO. | 2-Theta | d(A) | BG | Height | I % | Area | I % | FWHM |
| --- | --- | --- | --- | --- | --- | --- | --- | --- |
| 5 | 13.92 | 6.36 | 79 | 147 | 52.3 | 4562 | 44.9 | 0.53 |
| 6 | 14.26 | 6.21 | 87 | 101 | 35.9 | 3170 | 31.2 | 0.53 |
| 7 | 15.38 | 5.76 | 114 | 108 | 38.4 | 1780 | 17.5 | 0.28 |
| 8 | 16.12 | 5.49 | 112 | 142 | 50.5 | 3339 | 32.8 | 0.40 |
| 9 | 17.68 | 5.01 | 95 | 147 | 52.3 | 2437 | 24 | 0.28 |
| 10 | 18.26 | 4.85 | 96 | 162 | 57.7 | 7164 | 70.4 | 0.75 |
| 11 | 20.64 | 4.30 | 313 | 281 | 100 | 10170 | 100 | 0.62 |
| 12 | 22.63 | 3.93 | 298 | 66 | 23.5 | 1272 | 12.5 | 0.33 |
| 13 | 27.13 | 3.28 | 204 | 94 | 33.5 | 1968 | 19.4 | 0.36 |

Example 13. Preparation of C003-N-(2-Hydroxyethyl)-Pyrrolidine Salt

Scheme 11

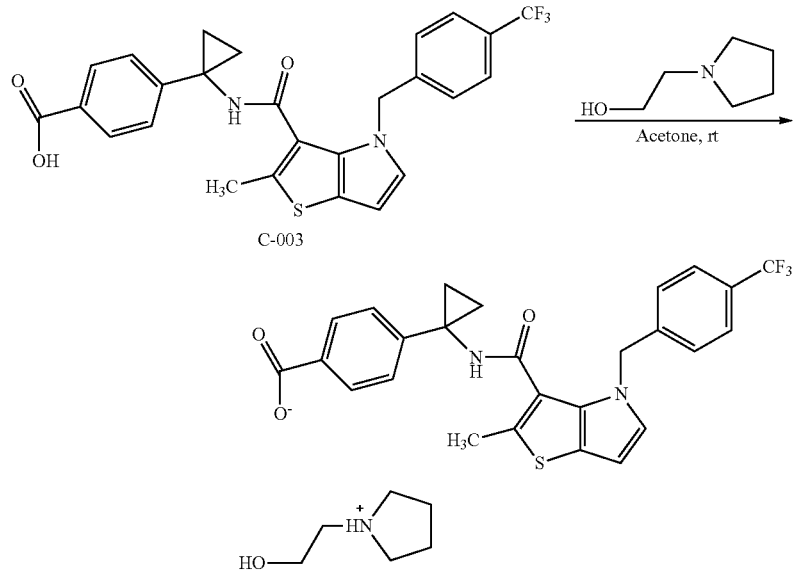

About 100 mg of C003 free acid was weighed out and put into a glass vial, and then it was dissolved by 5 mL acetone with sonication. Afterwards, 25.4 μl of N-(2-hydroxyethyl)-pyrrolidine was added into the vial by drop wise. The sample was kept stirring for 24 hrs at room temperature. After stirring for 24 hrs, brown solution was observed. The solvent was removed by spontaneous evaporation, and some solid was obtained. After that, the solid was re-crystallized in isopropyl alcohol (Form 1) or ethyl acetate (Form 2). For example: About 30 mg of C003-N-(2-Hydroxyethyl)-Pyrrolidine Salt was suspended in 0.5 ml ethyl acetate overnight. The solid precipitation was isolated by centrifugation method and further dried in vacuum oven at 60° C. for 5 hours. The resultant salt's XRPD data are listed below in Tables 12 and 13.

TABLE 12

XRPD 2-theta value of C003 N-(2-Hydroxyethyl)-Pyrrolidine salt Form 1

| NO. | 2-Theta | d(A) | BG | Height | I % | Area | I % | FWHM |
|---|---|---|---|---|---|---|---|---|
| 1 | 8.00 | 11.05 | 71 | 33 | 3.8 | 333 | 1.7 | 0.17 |
| 2 | 8.80 | 10.04 | 76 | 232 | 26.9 | 4139 | 21.5 | 0.30 |
| 3 | 9.26 | 9.54 | 74 | 126 | 14.6 | 3311 | 17.2 | 0.45 |
| 4 | 9.88 | 8.95 | 76 | 38 | 4.4 | 402 | 2.1 | 0.18 |
| 5 | 12.26 | 7.21 | 71 | 81 | 9.4 | 960 | 5 | 0.20 |
| 6 | 13.08 | 6.76 | 69 | 89 | 10.3 | 1213 | 6.3 | 0.23 |
| 7 | 14.12 | 6.27 | 89 | 305 | 35.4 | 4086 | 21.2 | 0.23 |
| 8 | 15.76 | 5.62 | 107 | 225 | 26.1 | 8935 | 46.3 | 0.68 |
| 9 | 16.44 | 5.39 | 126 | 332 | 38.6 | 7625 | 39.6 | 0.39 |
| 10 | 17.58 | 5.04 | 99 | 177 | 20.6 | 4750 | 24.6 | 0.46 |
| 11 | 17.96 | 4.93 | 99 | 235 | 27.3 | 6729 | 34.9 | 0.49 |
| 12 | 18.62 | 4.76 | 210 | 416 | 48.3 | 13884 | 72 | 0.57 |
| 13 | 19.00 | 4.67 | 191 | 861 | 100 | 19278 | 100 | 0.38 |
| 14 | 19.66 | 4.51 | 165 | 91 | 10.6 | 1315 | 6.8 | 0.25 |
| 15 | 20.66 | 4.30 | 150 | 462 | 53.7 | 8102 | 42 | 0.30 |
| 16 | 21.18 | 4.19 | 203 | 161 | 18.7 | 5751 | 29.8 | 0.61 |
| 17 | 21.78 | 4.08 | 268 | 216 | 25.1 | 4344 | 22.5 | 0.34 |
| 18 | 22.57 | 3.94 | 220 | 104 | 12.1 | 1773 | 9.2 | 0.29 |
| 19 | 23.22 | 3.83 | 187 | 267 | 31 | 3561 | 18.5 | 0.23 |
| 20 | 24.50 | 3.63 | 139 | 241 | 28 | 7299 | 37.9 | 0.52 |
| 21 | 25.08 | 3.55 | 158 | 244 | 28.3 | 5183 | 26.9 | 0.36 |
| 22 | 26.42 | 3.37 | 139 | 297 | 34.5 | 8678 | 45 | 0.50 |
| 23 | 27.74 | 3.21 | 136 | 130 | 15.1 | 5086 | 26.4 | 0.67 |
| 24 | 28.22 | 3.16 | 126 | 186 | 21.6 | 6320 | 32.8 | 0.58 |
| 25 | 30.62 | 2.92 | 138 | 70 | 8.1 | 1690 | 8.8 | 0.41 |
| 26 | 31.12 | 2.87 | 123 | 67 | 7.8 | 1684 | 8.7 | 0.43 |
| 27 | 31.99 | 2.80 | 110 | 44 | 5.1 | 875 | 4.5 | 0.34 |
| 28 | 35.35 | 2.54 | 107 | 37 | 4.3 | 1104 | 5.7 | 0.51 |
| 29 | 37.70 | 2.38 | 111 | 41 | 4.8 | 709 | 3.7 | 0.29 |
| 30 | 39.96 | 2.25 | 109 | 59 | 6.9 | 1124 | 5.8 | 0.32 |

TABLE 13

XRPD 2-theta value of C003 N-(2-Hydroxyethyl)-Pyrrolidine salt Form 2

| NO. | 2-Theta | d(A) | BG | Height | I % | Area | I % | FWHM |
|---|---|---|---|---|---|---|---|---|
| 1 | 7.94 | 11.13 | 61 | 63 | 7 | 628 | 3.9 | 0.17 |
| 2 | 9.24 | 9.56 | 66 | 200 | 22.1 | 2654 | 16.5 | 0.23 |
| 3 | 10.12 | 8.73 | 67 | 171 | 18.9 | 3151 | 19.6 | 0.31 |
| 4 | 10.78 | 8.20 | 69 | 215 | 23.8 | 2674 | 16.6 | 0.21 |
| 5 | 11.82 | 7.48 | 56 | 58 | 6.4 | 660 | 4.1 | 0.19 |
| 6 | 13.28 | 6.66 | 67 | 91 | 10.1 | 2955 | 18.3 | 0.55 |
| 7 | 14.04 | 6.30 | 85 | 249 | 27.5 | 3567 | 22.1 | 0.24 |
| 8 | 14.78 | 5.99 | 87 | 359 | 39.7 | 5531 | 34.3 | 0.26 |
| 9 | 15.98 | 5.54 | 78 | 114 | 12.6 | 3585 | 22.3 | 0.54 |
| 10 | 16.48 | 5.37 | 83 | 225 | 24.9 | 5591 | 34.7 | 0.42 |
| 11 | 17.52 | 5.06 | 139 | 93 | 10.3 | 877 | 5.4 | 0.16 |
| 12 | 18.50 | 4.79 | 200 | 904 | 100 | 16111 | 100 | 0.30 |
| 13 | 19.38 | 4.58 | 233 | 141 | 15.6 | 2434 | 15.1 | 0.29 |
| 14 | 19.94 | 4.45 | 226 | 140 | 15.5 | 3268 | 20.3 | 0.40 |

TABLE 13-continued

XRPD 2-theta value of C003 N-(2-Hydroxyethyl)-Pyrrolidine salt Form 2

| NO. | 2-Theta | d(A) | BG | Height | I % | Area | I % | FWHM |
|---|---|---|---|---|---|---|---|---|
| 15 | 20.50 | 4.33 | 241 | 365 | 40.4 | 4810 | 29.9 | 0.22 |
| 16 | 21.12 | 4.20 | 234 | 60 | 6.6 | 1257 | 7.8 | 0.36 |
| 17 | 21.56 | 4.12 | 231 | 199 | 22 | 4671 | 29 | 0.40 |
| 18 | 22.08 | 4.02 | 243 | 125 | 13.8 | 1218 | 7.6 | 0.17 |
| 19 | 22.58 | 3.93 | 244 | 60 | 6.6 | 327 | 2 | 0.09 |
| 20 | 23.12 | 3.84 | 204 | 340 | 37.6 | 10777 | 66.9 | 0.54 |
| 21 | 23.60 | 3.77 | 195 | 185 | 20.5 | 5632 | 35 | 0.52 |
| 22 | 24.48 | 3.63 | 162 | 124 | 13.7 | 1482 | 9.2 | 0.20 |
| 23 | 25.26 | 3.52 | 195 | 271 | 30 | 4004 | 24.9 | 0.25 |
| 24 | 26.08 | 3.41 | 168 | 206 | 22.8 | 4098 | 25.4 | 0.34 |
| 25 | 27.24 | 3.27 | 190 | 170 | 18.8 | 1755 | 10.9 | 0.18 |
| 26 | 27.71 | 3.22 | 122 | 162 | 17.9 | 9314 | 57.8 | 0.98 |
| 27 | 28.12 | 3.17 | 170 | 188 | 20.8 | 4774 | 29.6 | 0.43 |
| 28 | 29.22 | 3.05 | 127 | 73 | 8.1 | 2061 | 12.8 | 0.48 |
| 29 | 29.82 | 2.99 | 127 | 65 | 7.2 | 1818 | 11.3 | 0.48 |
| 30 | 30.58 | 2.92 | 123 | 145 | 16 | 3007 | 18.7 | 0.35 |
| 31 | 31.10 | 2.87 | 122 | 48 | 5.3 | 1103 | 6.8 | 0.39 |
| 32 | 33.15 | 2.70 | 102 | 62 | 6.9 | 1026 | 6.4 | 0.28 |
| 33 | 34.34 | 2.61 | 105 | 91 | 10.1 | 1804 | 11.2 | 0.34 |
| 34 | 35.37 | 2.54 | 99 | 55 | 6.1 | 753 | 4.7 | 0.23 |
| 35 | 36.32 | 2.47 | 104 | 92 | 10.2 | 1580 | 9.8 | 0.29 |
| 36 | 40.20 | 2.24 | 99 | 69 | 7.6 | 1502 | 9.3 | 0.37 |
| 37 | 41.68 | 2.17 | 107 | 49 | 5.4 | 755 | 4.7 | 0.26 |
| 38 | 42.09 | 2.14 | 107 | 41 | 4.5 | 690 | 4.3 | 0.29 |
| 39 | 43.94 | 2.06 | 99 | 51 | 5.6 | 745 | 4.6 | 0.25 |
| 40 | 45.21 | 2.00 | 93 | 39 | 4.3 | 340 | 2.1 | 0.15 |
| 41 | 47.21 | 1.92 | 91 | 41 | 4.5 | 1042 | 6.5 | 0.43 |
| 42 | 47.88 | 1.90 | 87 | 37 | 4.1 | 1305 | 8.1 | 0.60 |

Example 14. Preparation of C003-N-Benzyl-2-phenylethanamine Salt

About 100 mg of C003 free acid was weighed out and put into a glass vial, and then it was dissolved by 5 mL acetone with sonication. Afterwards, 47.6 µl of N-(2-hydroxyethyl)-pyrrolidine was added into the vial by drop wise. The sample was kept stirring for 24 hrs at room temperature. After stirring for 24 hrs, brown solution was observed. The solvent was removed by spontaneous evaporation, and some solid was obtained (Form 1). After that, the solid was re-crystallized in isopropyl alcohol (Form 2) or ethyl acetate (Form 2). About 30 mg of C003-N-benzyl-2-phenylethanamine salt was suspended in 0.3 ml ethyl acetate overnight. The solid precipitation was isolated by centrifugation method and further dried in vacuum oven at 60° C. for 2 hours. The resultant salt's XRPD data are provide below in Tables 14-15.

TABLE 14

XRPD 2-theta of C-003/N-Benzyl-2-phenylethanamine salt (Form 1)

| NO. | 2-Theta | d(A) | BG | Height | I % | Area | I % | FWHM |
|---|---|---|---|---|---|---|---|---|
| 1 | 5.21 | 16.97 | 162 | 130 | 7.7 | 996 | 1.7 | 0.13 |
| 2 | 6.36 | 13.88 | 155 | 599 | 35.3 | 13138 | 22.4 | 0.37 |
| 3 | 10.36 | 8.53 | 82 | 140 | 8.2 | 2792 | 4.8 | 0.34 |
| 4 | 12.13 | 7.29 | 103 | 55 | 3.2 | 1705 | 2.9 | 0.53 |
| 5 | 12.64 | 7.00 | 127 | 97 | 5.7 | 2324 | 4 | 0.41 |
| 6 | 14.40 | 6.15 | 196 | 214 | 12.6 | 3776 | 6.4 | 0.30 |
| 7 | 15.48 | 5.72 | 224 | 216 | 12.7 | 3994 | 6.8 | 0.31 |
| 8 | 18.56 | 4.78 | 249 | 977 | 57.6 | 29740 | 50.7 | 0.52 |
| 9 | 18.94 | 4.68 | 315 | 1697 | 100 | 58669 | 100 | 0.59 |
| 10 | 19.78 | 4.48 | 597 | 389 | 22.9 | 4532 | 7.7 | 0.20 |
| 11 | 20.60 | 4.31 | 423 | 303 | 17.9 | 6150 | 10.5 | 0.35 |
| 12 | 21.66 | 4.10 | 318 | 146 | 8.6 | 1831 | 3.1 | 0.21 |
| 13 | 22.58 | 3.93 | 299 | 239 | 14.1 | 5726 | 9.8 | 0.41 |

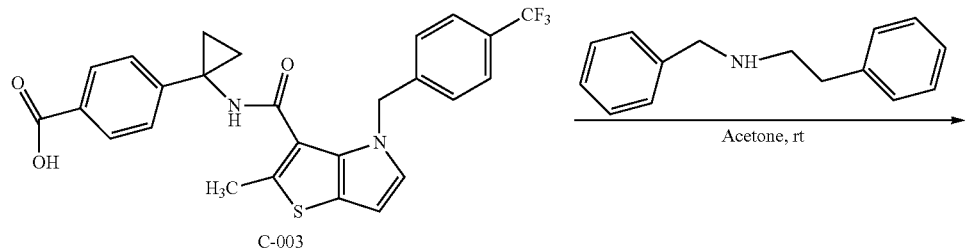

Scheme 12

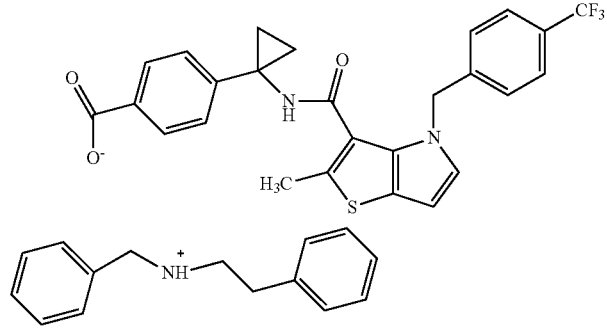

TABLE 14-continued

XRPD 2-theta of C-003/N-Benzyl-2-phenylethanamine salt (Form 1)

| NO. | 2-Theta | d(A) | BG | Height | I % | Area | I % | FWHM |
|---|---|---|---|---|---|---|---|---|
| 14 | 24.28 | 3.66 | 268 | 138 | 8.1 | 4596 | 7.8 | 0.57 |
| 15 | 24.64 | 3.61 | 275 | 251 | 14.8 | 7713 | 13.1 | 0.52 |
| 16 | 25.82 | 3.45 | 277 | 79 | 4.7 | 840 | 1.4 | 0.18 |
| 17 | 26.74 | 3.33 | 257 | 57 | 3.4 | 1032 | 1.8 | 0.31 |
| 18 | 29.38 | 3.04 | 180 | 58 | 3.4 | 771 | 1.3 | 0.23 |
| 19 | 30.04 | 2.97 | 185 | 79 | 4.7 | 1752 | 3 | 0.38 |
| 20 | 31.83 | 2.81 | 170 | 64 | 3.8 | 882 | 1.5 | 0.23 |
| 21 | 36.62 | 2.45 | 140 | 70 | 4.1 | 2188 | 3.7 | 0.53 |

TABLE 15

XRPD 2-theta of C-003/N-Benzyl-2-phenylethanamine salt (Form 2)

| NO. | 2-Theta | d(A) | BG | Height | I % | Area | I % | FWHM |
|---|---|---|---|---|---|---|---|---|
| 1 | 7.78 | 11.36 | 67 | 233 | 41.5 | 3899 | 41.3 | 0.28 |
| 2 | 10.56 | 8.37 | 62 | 96 | 17.1 | 1367 | 14.5 | 0.24 |
| 3 | 11.26 | 7.85 | 63 | 57 | 10.2 | 582 | 6.2 | 0.17 |
| 4 | 12.06 | 7.33 | 72 | 74 | 13.2 | 1129 | 12 | 0.26 |
| 5 | 13.34 | 6.63 | 86 | 90 | 16 | 2416 | 25.6 | 0.46 |
| 6 | 13.87 | 6.38 | 89 | 65 | 11.6 | 1353 | 14.3 | 0.35 |
| 7 | 14.72 | 6.01 | 131 | 115 | 20.5 | 1677 | 17.8 | 0.25 |
| 8 | 15.60 | 5.68 | 146 | 388 | 69.2 | 6096 | 64.5 | 0.27 |
| 9 | 16.24 | 5.45 | 124 | 72 | 12.8 | 689 | 7.3 | 0.16 |
| 10 | 17.68 | 5.01 | 119 | 289 | 51.5 | 9447 | 100 | 0.56 |
| 11 | 18.20 | 4.87 | 253 | 341 | 60.8 | 5337 | 56.5 | 0.27 |
| 12 | 18.86 | 4.70 | 281 | 491 | 87.5 | 8311 | 88 | 0.29 |
| 13 | 19.50 | 4.55 | 271 | 561 | 100 | 7350 | 77.8 | 0.22 |
| 14 | 20.32 | 4.37 | 253 | 239 | 42.6 | 4969 | 52.6 | 0.35 |
| 15 | 20.76 | 4.27 | 228 | 258 | 46 | 6738 | 71.3 | 0.44 |
| 16 | 22.72 | 3.91 | 187 | 251 | 44.7 | 5654 | 59.8 | 0.38 |
| 17 | 23.50 | 3.78 | 199 | 61 | 10.9 | 284 | 3 | 0.08 |
| 18 | 24.22 | 3.67 | 175 | 375 | 66.8 | 8225 | 87.1 | 0.37 |
| 19 | 25.50 | 3.49 | 142 | 250 | 44.6 | 3932 | 41.6 | 0.27 |
| 20 | 26.42 | 3.37 | 137 | 49 | 8.7 | 674 | 7.1 | 0.23 |
| 21 | 27.26 | 3.27 | 137 | 67 | 11.9 | 953 | 10.1 | 0.24 |
| 22 | 28.08 | 3.18 | 147 | 127 | 22.6 | 2007 | 21.2 | 0.27 |
| 23 | 28.98 | 3.08 | 162 | 62 | 11.1 | 553 | 5.9 | 0.15 |
| 24 | 30.24 | 2.95 | 145 | 77 | 13.7 | 1180 | 12.5 | 0.26 |
| 25 | 31.00 | 2.88 | 133 | 127 | 22.6 | 2176 | 23 | 0.29 |
| 26 | 32.20 | 2.78 | 105 | 67 | 11.9 | 832 | 8.8 | 0.21 |
| 27 | 34.20 | 2.62 | 101 | 59 | 10.5 | 597 | 6.3 | 0.17 |
| 28 | 36.44 | 2.46 | 98 | 60 | 10.7 | 1412 | 14.9 | 0.40 |
| 29 | 37.44 | 2.40 | 92 | 66 | 11.8 | 1272 | 13.5 | 0.33 |
| 30 | 39.80 | 2.26 | 91 | 39 | 7 | 952 | 10.1 | 0.42 |
| 31 | 41.40 | 2.18 | 91 | 47 | 8.4 | 1143 | 12.1 | 0.41 |
| 32 | 44.82 | 2.02 | 83 | 41 | 7.3 | 562 | 5.9 | 0.23 |

Example 15. Preparation of C003/Diethylamine Salt

Scheme 13

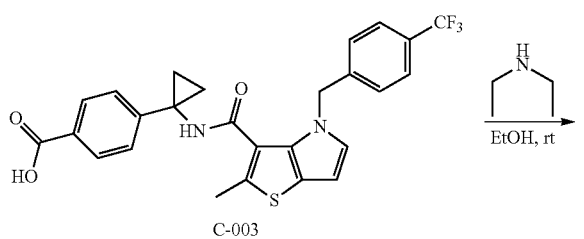

C-003

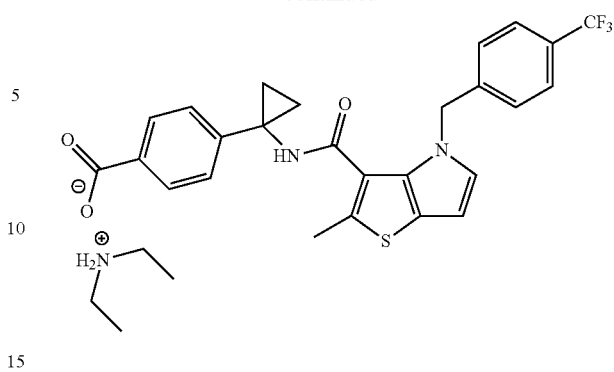

Compound of Example 2 (200 mg, 0.40 mmol) was added to a flask with EtOH (2.0 mL) to get a white suspension. Diethylamine (35.2 mg, 0.48 mmol) was added in one portion, the reaction turned to be clear. After stirred for 30 min, a white precipitate came out. And the solution was continually stirred overnight and the white solid was collected to afford the target compound as a white solid (192 mg, 84% yield). This compound's XRPD data are provided below in Table 16.

TABLE 16

XRPD 2-theta of C003/Diethylamine salt

| NO. | Pos.[°2Th.] | Height[cts] | FWHM[°2Th.] | d(A) | Rel.Int.[%] |
|---|---|---|---|---|---|
| 1 | 6.76 | 5113 | 0.13 | 13.08 | 53.7 |
| 2 | 7.04 | 3789 | 0.13 | 12.55 | 39.8 |
| 3 | 9.69 | 248 | 0.15 | 9.13 | 2.6 |
| 4 | 10.54 | 1342 | 0.20 | 8.39 | 14.1 |
| 5 | 11.46 | 612 | 0.10 | 7.72 | 6.4 |
| 6 | 11.75 | 707 | 0.15 | 7.53 | 7.4 |
| 7 | 13.71 | 1281 | 0.15 | 6.46 | 13.5 |
| 8 | 14.12 | 1845 | 0.10 | 6.27 | 19.4 |
| 9 | 14.48 | 3581 | 0.23 | 6.12 | 37.6 |
| 10 | 15.67 | 9516 | 0.18 | 5.65 | 100.0 |
| 11 | 16.32 | 8923 | 0.20 | 5.43 | 93.8 |
| 12 | 17.25 | 1878 | 0.23 | 5.14 | 19.7 |
| 13 | 17.77 | 1054 | 0.18 | 4.99 | 11.1 |
| 14 | 18.23 | 1594 | 0.15 | 4.87 | 16.8 |
| 15 | 19.30 | 7038 | 0.23 | 4.60 | 74.0 |
| 16 | 19.55 | 2400 | 0.10 | 4.54 | 25.2 |
| 17 | 20.31 | 3738 | 0.18 | 4.37 | 39.3 |
| 18 | 20.61 | 2086 | 0.08 | 4.31 | 21.9 |
| 19 | 20.90 | 2371 | 0.18 | 4.25 | 24.9 |
| 20 | 21.27 | 1995 | 0.10 | 4.18 | 21.0 |
| 21 | 21.67 | 4436 | 0.15 | 4.10 | 46.6 |
| 22 | 21.99 | 4385 | 0.18 | 4.04 | 46.1 |
| 23 | 22.60 | 1762 | 0.18 | 3.93 | 18.5 |
| 24 | 23.05 | 595 | 0.31 | 3.86 | 6.3 |
| 25 | 23.72 | 1189 | 0.13 | 3.75 | 12.5 |
| 26 | 24.49 | 1339 | 0.18 | 3.64 | 14.1 |
| 27 | 25.42 | 1854 | 0.23 | 3.50 | 19.5 |
| 28 | 26.40 | 979 | 0.26 | 3.38 | 10.3 |
| 29 | 27.16 | 1809 | 0.20 | 3.28 | 19.0 |
| 30 | 28.39 | 1808 | 0.15 | 3.14 | 19.0 |
| 31 | 29.14 | 1012 | 0.26 | 3.06 | 10.6 |
| 32 | 29.88 | 680 | 0.31 | 2.99 | 7.2 |
| 33 | 30.20 | 640 | 0.15 | 2.96 | 6.7 |
| 34 | 31.77 | 1001 | 0.18 | 2.82 | 10.5 |
| 35 | 33.13 | 565 | 0.20 | 2.70 | 5.9 |
| 36 | 34.51 | 289 | 0.20 | 2.60 | 3.0 |
| 37 | 35.38 | 377 | 0.15 | 2.54 | 4.0 |
| 38 | 36.51 | 308 | 0.20 | 2.46 | 3.2 |
| 39 | 37.96 | 107 | 0.31 | 2.37 | 1.1 |

Example 16. Preparation of C0003-Dihydroxylethylamine Salt

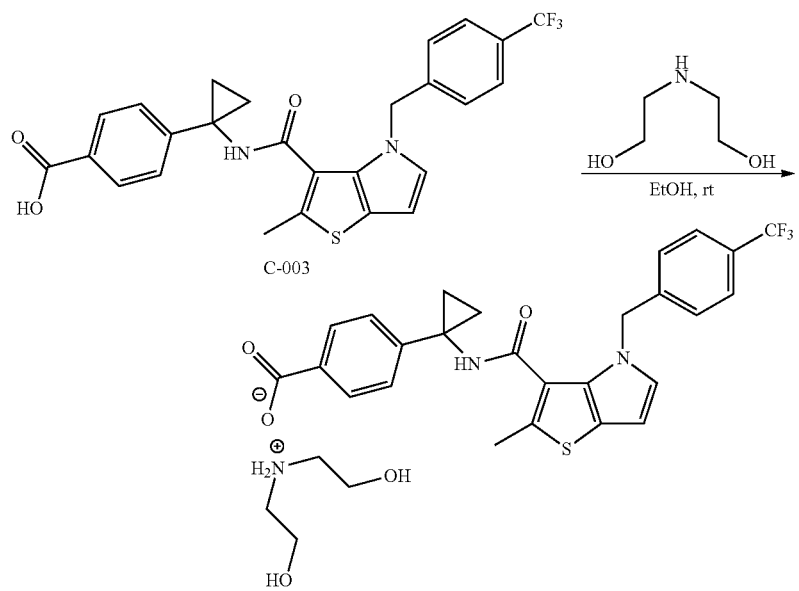

Scheme 14

Compound of Example 2 (100 mg, 0.20 mmol) was added to a flask with EtOH (1.0 mL) to get a white suspension. Diethanolamine (25 mg, 0.24 mmol) was added in one portion and the reaction mixture turned clear. After stirring for 30 minutes, a white precipitate was observed. After continued stirring overnight and adding 2 mL EtOH, a white solid was collected to afford the target salt as a white solid (82 mg, 68% yield). This salt's XRPD data are provided in Table 17 below.

TABLE 17

XRPD 2-theta of C003/diethanolamine salt

| NO. | Pos.[°2Th.] | Height[cts] | FWHM[°2Th.] | d(A) | Rel.Int.[%] |
|---|---|---|---|---|---|
| 1 | 3.81 | 626 | 0.15 | 23.20 | 16.8 |
| 2 | 7.84 | 417 | 0.15 | 11.28 | 11.2 |
| 3 | 8.26 | 376 | 0.20 | 10.71 | 10.1 |
| 4 | 9.67 | 528 | 0.20 | 9.14 | 14.1 |
| 5 | 10.24 | 1174 | 0.20 | 8.64 | 31.4 |
| 6 | 11.52 | 397 | 0.18 | 7.68 | 10.6 |
| 7 | 12.65 | 1247 | 0.26 | 7.00 | 33.4 |
| 8 | 13.40 | 1303 | 0.18 | 6.61 | 34.9 |
| 9 | 13.79 | 3735 | 0.23 | 6.42 | 100.0 |
| 10 | 14.29 | 1006 | 0.15 | 6.20 | 27.0 |
| 11 | 15.31 | 1669 | 0.20 | 5.79 | 44.7 |

TABLE 17-continued

XRPD 2-theta of C003/diethanolamine salt

| NO. | Pos.[°2Th.] | Height[cts] | FWHM[°2Th.] | d(A) | Rel.Int.[%] |
|---|---|---|---|---|---|
| 12 | 16.09 | 703 | 0.15 | 5.51 | 18.8 |
| 13 | 16.84 | 1973 | 0.18 | 5.26 | 52.8 |
| 14 | 17.48 | 146 | 0.15 | 5.07 | 3.9 |
| 15 | 18.47 | 1198 | 0.41 | 4.80 | 32.1 |
| 16 | 19.17 | 1256 | 0.20 | 4.63 | 33.6 |
| 17 | 20.07 | 2491 | 0.23 | 4.42 | 66.7 |
| 18 | 20.59 | 2111 | 0.13 | 4.31 | 56.5 |
| 19 | 21.10 | 1241 | 0.15 | 4.21 | 33.2 |
| 20 | 22.34 | 1516 | 0.31 | 3.98 | 40.6 |
| 21 | 23.05 | 1891 | 0.36 | 3.86 | 50.6 |
| 22 | 26.31 | 262 | 0.20 | 3.39 | 7.0 |
| 23 | 27.01 | 323 | 0.41 | 3.30 | 8.6 |
| 24 | 27.90 | 448 | 0.26 | 3.20 | 12.0 |
| 25 | 28.40 | 545 | 0.20 | 3.14 | 14.6 |
| 26 | 29.76 | 343 | 0.26 | 3.00 | 9.2 |
| 27 | 33.99 | 128 | 0.31 | 2.64 | 3.4 |
| 28 | 35.65 | 171 | 0.41 | 2.52 | 4.6 |

Example 17. Preparation of C003-1,1,1-Tris(Hydroxymethyl)-Methylamine Salt

Scheme 10

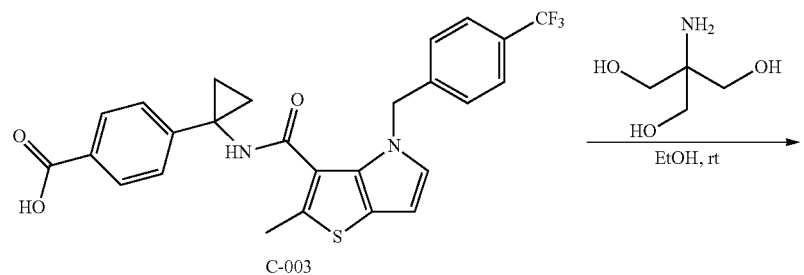

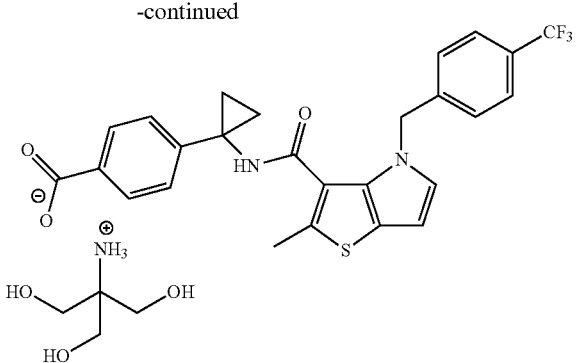

Compound of Example 2 (200 mg, 0.40 mmol) was added to a flask with EtOH (4.0 mL) to result in a white suspension. Tris(Hydroxymethyl)-Methylamine base (58 mg, 0.48 mmol) was added in one portion and the reaction mixture turned clear. After stirred for 30 minutes, a white precipitate was observed and kept stirring overnight, a white solid was collected to afford the target salt as a white solid (227 mg, 91% yield). This salt's XRPD data are provided in Table 18 below.

TABLE 18

XRPD 2-theta of C-003/1,1,1-Tris(Hydroxymethyl)-Methylamine salt

| NO. | Pos.[°2Th.] | Height[cts] | FWHM[°2Th.] | d(A) | Rel.Int.[%] |
|---|---|---|---|---|---|
| 1 | 4.39 | 179 | 0.15 | 20.13 | 6.9 |
| 2 | 5.63 | 375 | 0.20 | 15.70 | 14.5 |
| 3 | 6.43 | 353 | 0.20 | 13.74 | 13.6 |
| 4 | 8.47 | 1926 | 0.18 | 10.44 | 74.3 |
| 5 | 8.77 | 1178 | 0.13 | 10.09 | 45.5 |
| 6 | 9.57 | 407 | 0.36 | 9.24 | 15.7 |
| 7 | 11.02 | 869 | 0.13 | 8.03 | 33.6 |
| 8 | 13.05 | 910 | 0.20 | 6.79 | 35.1 |
| 9 | 13.40 | 1257 | 0.18 | 6.61 | 48.5 |
| 10 | 14.44 | 1881 | 0.20 | 6.14 | 72.6 |
| 11 | 15.50 | 2590 | 0.20 | 5.72 | 100.0 |
| 12 | 15.88 | 1158 | 0.18 | 5.58 | 44.7 |
| 13 | 17.17 | 592 | 0.26 | 5.16 | 22.9 |
| 14 | 17.66 | 315 | 0.20 | 5.02 | 12.2 |
| 15 | 19.62 | 2484 | 0.18 | 4.53 | 95.9 |
| 16 | 20.73 | 447 | 0.20 | 4.29 | 17.2 |
| 17 | 21.33 | 278 | 0.15 | 4.17 | 10.7 |
| 18 | 22.08 | 740 | 0.15 | 4.03 | 28.6 |
| 19 | 22.95 | 1193 | 0.23 | 3.88 | 46.0 |
| 20 | 24.23 | 727 | 0.13 | 3.67 | 28.1 |
| 21 | 25.71 | 556 | 0.41 | 3.47 | 21.5 |
| 22 | 26.59 | 379 | 0.31 | 3.35 | 14.6 |
| 23 | 27.33 | 402 | 0.26 | 3.26 | 15.5 |
| 24 | 28.77 | 428 | 0.26 | 3.10 | 16.5 |
| 25 | 30.02 | 363 | 0.26 | 2.98 | 14.0 |
| 26 | 31.25 | 441 | 0.26 | 2.86 | 17.0 |
| 27 | 33.12 | 256 | 0.26 | 2.70 | 9.9 |
| 28 | 34.79 | 345 | 0.26 | 2.58 | 13.3 |
| 29 | 35.89 | 144 | 0.51 | 2.50 | 5.6 |
| 30 | 37.65 | 291 | 0.41 | 2.39 | 11.2 |

Example 18. C003 Tris-Salt Form 1

The start crystal form was crystallized in mixture solvents (ethanol: MTBE) or acetone. In the polymorph screening study, the Form 1 was not changed in isopropyl alcohol, acetone, acetonitrile, ethyl acetate, isopropyl acetate, MEK, MIBK, MTBE, toluene, DCM, heptane, and cyclohexane by slurry method. Form 1 is an anhydrous form. The XRPD data are provided below in Table 19.

TABLE 19

XRPD 2-theta of C003 tris-salt Form 1

| NO. | 2-Theta | d(A) | BG | Height | I % | Area | I % | FWHM |
|---|---|---|---|---|---|---|---|---|
| 1 | 5.70 | 15.49 | 71 | 155 | 8.9 | 1566 | 5.3 | 0.17 |
| 2 | 8.48 | 10.42 | 58 | 804 | 46.4 | 13490 | 45.5 | 0.29 |
| 3 | 9.18 | 9.63 | 49 | 1733 | 100 | 23376 | 78.9 | 0.23 |
| 4 | 10.36 | 8.53 | 55 | 77 | 4.4 | 881 | 3.0 | 0.20 |
| 5 | 11.26 | 7.85 | 59 | 375 | 21.6 | 5071 | 17.1 | 0.23 |
| 6 | 12.76 | 6.93 | 63 | 209 | 12.1 | 3435 | 11.6 | 0.28 |
| 7 | 13.44 | 6.58 | 72 | 102 | 5.9 | 1028 | 3.5 | 0.17 |
| 8 | 14.16 | 6.25 | 58 | 276 | 15.9 | 7182 | 24.2 | 0.44 |
| 9 | 14.58 | 6.07 | 56 | 266 | 15.3 | 6169 | 20.8 | 0.39 |
| 10 | 16.60 | 5.34 | 85 | 331 | 19.1 | 6616 | 22.3 | 0.34 |
| 11 | 16.94 | 5.23 | 95 | 227 | 13.1 | 3162 | 10.7 | 0.24 |
| 12 | 17.62 | 5.03 | 102 | 172 | 9.9 | 2551 | 8.6 | 0.25 |
| 13 | 18.12 | 4.89 | 106 | 56 | 3.2 | 749 | 2.5 | 0.23 |
| 14 | 19.06 | 4.65 | 140 | 136 | 7.8 | 1528 | 5.2 | 0.19 |
| 15 | 20.10 | 4.41 | 179 | 1043 | 60.2 | 29625 | 100.0 | 0.48 |
| 16 | 20.90 | 4.25 | 200 | 142 | 8.2 | 1361 | 4.6 | 0.16 |
| 17 | 21.56 | 4.12 | 198 | 338 | 19.5 | 4886 | 16.5 | 0.25 |
| 18 | 22.08 | 4.02 | 166 | 284 | 16.4 | 7123 | 24.0 | 0.43 |
| 19 | 22.46 | 3.96 | 131 | 159 | 9.2 | 4877 | 16.5 | 0.52 |
| 20 | 23.10 | 3.85 | 117 | 265 | 15.3 | 5362 | 18.1 | 0.34 |
| 21 | 23.56 | 3.77 | 101 | 83 | 4.8 | 1957 | 6.6 | 0.40 |
| 22 | 24.32 | 3.66 | 94 | 62 | 3.6 | 608 | 2.1 | 0.17 |
| 23 | 25.04 | 3.55 | 104 | 124 | 7.2 | 4373 | 14.8 | 0.60 |
| 24 | 25.50 | 3.49 | 112 | 144 | 8.3 | 4354 | 14.7 | 0.51 |
| 25 | 26.94 | 3.31 | 157 | 155 | 8.9 | 1918 | 6.5 | 0.21 |
| 26 | 27.52 | 3.24 | 117 | 101 | 5.8 | 3248 | 11.0 | 0.55 |
| 27 | 27.88 | 3.20 | 142 | 134 | 7.7 | 2417 | 8.2 | 0.31 |
| 28 | 29.68 | 3.01 | 106 | 106 | 6.1 | 3198 | 10.8 | 0.51 |
| 29 | 30.04 | 2.97 | 114 | 50 | 2.9 | 2364 | 8.0 | 0.80 |
| 30 | 30.60 | 2.92 | 117 | 183 | 10.6 | 3348 | 11.3 | 0.31 |
| 31 | 31.28 | 2.86 | 119 | 65 | 3.8 | 1128 | 3.8 | 0.30 |
| 32 | 31.94 | 2.80 | 119 | 87 | 5 | 1661 | 5.6 | 0.33 |
| 33 | 32.48 | 2.75 | 119 | 137 | 7.9 | 3316 | 11.2 | 0.41 |
| 34 | 33.12 | 2.70 | 108 | 50 | 2.9 | 1489 | 5.0 | 0.51 |
| 35 | 33.38 | 2.68 | 105 | 49 | 2.8 | 1092 | 3.7 | 0.38 |
| 36 | 36.50 | 2.46 | 100 | 94 | 5.4 | 3481 | 11.8 | 0.63 |
| 37 | 36.84 | 2.44 | 102 | 138 | 8 | 3932 | 13.3 | 0.48 |
| 38 | 37.90 | 2.37 | 96 | 54 | 3.1 | 1078 | 3.6 | 0.34 |
| 39 | 38.24 | 2.35 | 101 | 37 | 2.1 | 1460 | 4.9 | 0.67 |
| 40 | 38.70 | 2.32 | 103 | 41 | 2.4 | 803 | 2.7 | 0.33 |
| 41 | 39.92 | 2.26 | 100 | 112 | 6.5 | 1724 | 5.8 | 0.26 |
| 42 | 41.08 | 2.20 | 97 | 85 | 4.9 | 1847 | 6.2 | 0.37 |
| 43 | 41.66 | 2.17 | 101 | 41 | 2.4 | 708 | 2.4 | 0.29 |
| 44 | 42.61 | 2.12 | 101 | 63 | 3.6 | 887 | 3.0 | 0.24 |
| 45 | 44.20 | 2.05 | 95 | 143 | 8.3 | 3004 | 10.1 | 0.36 |
| 46 | 45.85 | 1.98 | 93 | 47 | 2.7 | 436 | 1.5 | 0.16 |
| 47 | 46.71 | 1.94 | 84 | 38 | 2.2 | 477 | 1.6 | 0.21 |
| 48 | 49.10 | 1.85 | 72 | 70 | 4 | 1540 | 5.2 | 0.37 |

Example 19. C0003 Tris-Salt Form 2

About 50 mg of C0003 Tris-salt was fully dissolved in good solvent such as ethanol at room temperature. Then the sample was spontaneously evaporated at room temperature for 1~2 weeks. The XRPD data are provided in Table 20 below.

TABLE 20

XRPD 2-theta of C0003 tris-salt Form 2

| NO. | 2-Theta | d(A) | BG | Height | I % | Area | I % | FWHM |
|---|---|---|---|---|---|---|---|---|
| 1 | 5.78 | 15.29 | 71 | 43 | 9.1 | 929 | 3.9 | 0.37 |
| 2 | 6.57 | 13.45 | 65 | 33 | 7 | 304 | 1.3 | 0.16 |
| 3 | 8.66 | 10.20 | 73 | 193 | 41 | 4040 | 17.2 | 0.36 |
| 4 | 8.94 | 9.89 | 80 | 136 | 28.9 | 2886 | 12.3 | 0.36 |
| 5 | 9.96 | 8.87 | 73 | 47 | 10 | 381 | 1.6 | 0.14 |
| 6 | 11.14 | 7.94 | 68 | 106 | 22.5 | 1384 | 5.9 | 0.22 |
| 7 | 13.11 | 6.75 | 89 | 83 | 17.6 | 1724 | 7.3 | 0.35 |
| 8 | 13.54 | 6.53 | 96 | 104 | 22.1 | 2716 | 11.5 | 0.44 |
| 9 | 14.50 | 6.10 | 111 | 181 | 38.4 | 3015 | 12.8 | 0.28 |
| 10 | 15.74 | 5.63 | 109 | 347 | 73.7 | 7406 | 31.5 | 0.36 |
| 11 | 17.56 | 5.05 | 127 | 135 | 28.7 | 5124 | 21.8 | 0.65 |
| 12 | 18.06 | 4.91 | 149 | 129 | 27.4 | 3870 | 16.4 | 0.51 |
| 13 | 18.80 | 4.72 | 194 | 100 | 21.2 | 1058 | 4.5 | 0.18 |
| 14 | 19.72 | 4.50 | 216 | 418 | 88.7 | 15102 | 64.2 | 0.61 |
| 15 | 20.12 | 4.41 | 241 | 471 | 100 | 23527 | 100 | 0.85 |
| 16 | 20.62 | 4.30 | 220 | 384 | 81.5 | 9328 | 39.6 | 0.41 |
| 17 | 21.64 | 4.10 | 245 | 67 | 14.2 | 582 | 2.5 | 0.15 |
| 18 | 22.32 | 3.98 | 253 | 137 | 29.1 | 7081 | 30.1 | 0.88 |
| 19 | 22.98 | 3.87 | 248 | 184 | 39.1 | 8338 | 35.4 | 0.77 |
| 20 | 24.32 | 3.66 | 194 | 68 | 14.4 | 765 | 3.3 | 0.19 |
| 21 | 25.26 | 3.52 | 185 | 91 | 19.3 | 2596 | 11 | 0.49 |
| 22 | 25.64 | 3.47 | 194 | 162 | 34.4 | 4491 | 19.1 | 0.47 |
| 23 | 26.61 | 3.35 | 215 | 61 | 13 | 658 | 2.8 | 0.18 |
| 24 | 27.60 | 3.23 | 206 | 102 | 21.7 | 1536 | 6.5 | 0.26 |
| 25 | 29.01 | 3.08 | 177 | 47 | 10 | 739 | 3.1 | 0.27 |
| 26 | 30.20 | 2.96 | 168 | 70 | 14.9 | 1034 | 4.4 | 0.25 |
| 27 | 34.79 | 2.58 | 117 | 41 | 8.7 | 523 | 2.2 | 0.22 |
| 28 | 37.46 | 2.40 | 117 | 73 | 15.5 | 1976 | 8.4 | 0.46 |

Example 20. C0003 Tris-Salt Form 3

About 50 mg of C0003 Tris-salt was fully dissolved in good solvent DMF to form an early saturated solution. Then the anti-solvents ethyl acetate, acetonitrile or MTBE was added drop-wise, until plenty of solid precipitated out. The sample was kept stirring overnight at room temperature. After that, the solid was isolated by centrifugation and dried at 40° C. under reducing pressure condition. Form 3 is DMF solvate. Its XRPD data are provided below in Table 21.

TABLE 21

XRPD 2-theta of C0003 tris-salt Form 3

| NO. | 2-Theta | d(A) | BG | Height | I % | Area | I % | FWHM |
|---|---|---|---|---|---|---|---|---|
| 1 | 6.50 | 13.59 | 63 | 129 | 40.6 | 2148 | 17.9 | 0.28 |
| 2 | 7.49 | 11.80 | 56 | 52 | 16.4 | 422 | 3.5 | 0.14 |
| 3 | 9.46 | 9.34 | 54 | 58 | 18.2 | 1550 | 12.9 | 0.45 |
| 4 | 9.84 | 8.98 | 50 | 58 | 18.2 | 1671 | 13.9 | 0.49 |
| 5 | 13.60 | 6.51 | 71 | 175 | 55 | 4236 | 35.3 | 0.41 |
| 6 | 14.00 | 6.32 | 84 | 198 | 62.3 | 4413 | 36.8 | 0.38 |
| 7 | 14.78 | 5.99 | 81 | 163 | 51.3 | 2378 | 19.8 | 0.25 |
| 8 | 16.84 | 5.26 | 101 | 163 | 51.3 | 3185 | 26.5 | 0.33 |
| 9 | 17.76 | 4.99 | 117 | 199 | 62.6 | 3526 | 29.4 | 0.30 |
| 10 | 18.18 | 4.88 | 150 | 270 | 84.9 | 12002 | 100 | 0.76 |
| 11 | 18.60 | 4.77 | 192 | 210 | 66 | 7450 | 62.1 | 0.60 |
| 12 | 18.96 | 4.68 | 203 | 95 | 29.9 | 1442 | 12 | 0.26 |
| 13 | 19.58 | 4.53 | 188 | 196 | 61.6 | 4888 | 40.7 | 0.42 |
| 14 | 20.08 | 4.42 | 166 | 318 | 100 | 8959 | 74.6 | 0.48 |
| 15 | 20.64 | 4.30 | 171 | 81 | 25.5 | 1136 | 9.5 | 0.24 |
| 16 | 22.52 | 3.94 | 254 | 104 | 32.7 | 2718 | 22.6 | 0.44 |
| 17 | 23.14 | 3.84 | 217 | 139 | 43.7 | 8079 | 67.3 | 0.99 |
| 18 | 23.80 | 3.74 | 225 | 159 | 50 | 2708 | 22.6 | 0.29 |
| 19 | 24.82 | 3.58 | 131 | 137 | 43.1 | 3081 | 25.7 | 0.38 |
| 20 | 25.31 | 3.52 | 113 | 61 | 19.2 | 1383 | 11.5 | 0.39 |

TABLE 21-continued

XRPD 2-theta of C0003 tris-salt Form 3

| NO. | 2-Theta | d(A) | BG | Height | I % | Area | I % | FWHM |
|---|---|---|---|---|---|---|---|---|
| 21 | 26.38 | 3.38 | 120 | 202 | 63.5 | 4387 | 36.6 | 0.37 |
| 22 | 26.90 | 3.31 | 133 | 83 | 26.1 | 1793 | 14.9 | 0.37 |
| 23 | 27.74 | 3.21 | 141 | 59 | 18.6 | 1220 | 10.2 | 0.35 |
| 24 | 28.28 | 3.15 | 138 | 172 | 54.1 | 4162 | 34.7 | 0.41 |
| 25 | 29.26 | 3.05 | 136 | 82 | 25.8 | 1169 | 9.7 | 0.24 |
| 26 | 30.56 | 2.92 | 116 | 120 | 37.7 | 2337 | 19.5 | 0.33 |
| 27 | 34.02 | 2.63 | 108 | 102 | 32.1 | 1441 | 12 | 0.24 |
| 28 | 34.75 | 2.58 | 100 | 36 | 11.3 | 516 | 4.3 | 0.24 |
| 29 | 36.18 | 2.48 | 94 | 86 | 27 | 2162 | 18 | 0.43 |
| 30 | 38.44 | 2.34 | 97 | 127 | 39.9 | 1873 | 15.6 | 0.25 |
| 31 | 40.01 | 2.25 | 94 | 36 | 11.3 | 621 | 5.2 | 0.29 |
| 32 | 47.74 | 1.90 | 78 | 36 | 11.3 | 481 | 4 | 0.23 |

Example 22. C0003 Tris-Salt Form 4

About 50 mg of C0003 Tris-salt was fully dissolved in good solvent methanol to form a nearly saturated solution. Then the anti-solvents toluene was added drop-wise, until plenty of solid precipitated out. The sample was kept stirring overnight at room temperature. After that, the solid was isolated by centrifugation and dried at 40° C. under reducing pressure condition. Form 4 is an anhydrate form and its XRPD data are provided below in Table 22.

TABLE 22

XRPD 2-theta of C0003 tris-salt Form 4

| NO. | 2-Theta | d(A) | BG | Height | I % | Area | I % | FWHM |
|---|---|---|---|---|---|---|---|---|
| 1 | 7.42 | 11.90 | 78 | 94 | 9.7 | 3165 | 11.6 | 0.57 |
| 2 | 7.80 | 11.33 | 82 | 88 | 9.1 | 3026 | 11.1 | 0.59 |
| 3 | 8.96 | 9.86 | 84 | 136 | 14 | 2664 | 9.8 | 0.33 |
| 4 | 10.22 | 8.65 | 79 | 37 | 3.8 | 473 | 1.7 | 0.22 |
| 5 | 11.12 | 7.95 | 73 | 49 | 5.1 | 690 | 2.5 | 0.24 |
| 6 | 13.88 | 6.37 | 108 | 968 | 100 | 27214 | 100 | 0.48 |
| 7 | 14.40 | 6.15 | 196 | 272 | 28.1 | 13035 | 47.9 | 0.82 |
| 8 | 14.82 | 5.97 | 234 | 80 | 8.3 | 448 | 1.6 | 0.10 |
| 9 | 16.56 | 5.35 | 171 | 115 | 11.9 | 2608 | 9.6 | 0.39 |
| 10 | 18.16 | 4.88 | 182 | 378 | 39 | 11097 | 40.8 | 0.50 |
| 11 | 20.34 | 4.36 | 253 | 131 | 13.5 | 3932 | 14.4 | 0.51 |
| 12 | 21.14 | 4.20 | 253 | 125 | 12.9 | 2951 | 10.8 | 0.40 |
| 13 | 21.66 | 4.10 | 239 | 81 | 8.4 | 2156 | 7.9 | 0.45 |
| 14 | 22.92 | 3.88 | 209 | 151 | 15.6 | 4488 | 16.5 | 0.51 |
| 15 | 23.34 | 3.81 | 192 | 86 | 8.9 | 4966 | 18.2 | 0.98 |
| 16 | 25.28 | 3.52 | 181 | 53 | 5.5 | 1353 | 5 | 0.43 |
| 17 | 26.70 | 3.34 | 175 | 123 | 12.7 | 2621 | 9.6 | 0.36 |
| 18 | 27.98 | 3.19 | 165 | 67 | 6.9 | 1987 | 7.3 | 0.50 |
| 19 | 29.29 | 3.05 | 170 | 48 | 5 | 632 | 2.3 | 0.22 |
| 20 | 35.60 | 2.52 | 128 | 54 | 5.6 | 1665 | 6.1 | 0.52 |

Example 23. C0003 Tris-Salt Form 5

About 50 mg of C0003 Tris-salt was fully dissolved in good solvent methanol to form a nearly saturated solution. Then the anti-solvents MTBE was added drop-wise, until plenty of solid precipitated out. The sample was kept stirring overnight at room temperature. After that, the solid was isolated by centrifugation and dried at 40° C. under reducing pressure condition. Its XRPD data are provided below in Table 23.

TABLE 23

XRPD 2-theta of C003 tris-salt Form 5

| NO. | 2-Theta | d(A) | BG | Height | I % | Area | I % | FWHM |
|---|---|---|---|---|---|---|---|---|
| 1 | 7.26 | 12.17 | 81 | 65 | 18.4 | 998 | 10.1 | 0.26 |
| 2 | 9.74 | 9.07 | 73 | 81 | 22.9 | 2234 | 22.7 | 0.47 |
| 3 | 10.98 | 8.05 | 72 | 42 | 11.9 | 425 | 4.3 | 0.17 |
| 4 | 13.94 | 6.35 | 98 | 274 | 77.6 | 7173 | 72.7 | 0.45 |
| 5 | 15.88 | 5.58 | 169 | 209 | 59.2 | 7723 | 78.3 | 0.63 |
| 6 | 18.18 | 4.88 | 229 | 353 | 100 | 9860 | 100 | 0.48 |
| 7 | 19.46 | 4.56 | 295 | 61 | 17.3 | 1464 | 14.8 | 0.41 |
| 8 | 19.71 | 4.50 | 311 | 77 | 21.8 | 1440 | 14.6 | 0.32 |
| 9 | 19.74 | 4.49 | 286 | 118 | 33.4 | 3474 | 35.2 | 0.50 |
| 10 | 20.33 | 4.36 | 282 | 94 | 26.6 | 3958 | 40.1 | 0.72 |
| 11 | 22.70 | 3.91 | 320 | 92 | 26.1 | 2064 | 20.9 | 0.38 |
| 12 | 23.27 | 3.82 | 274 | 122 | 34.6 | 4967 | 50.4 | 0.69 |
| 13 | 23.42 | 3.80 | 288 | 60 | 17 | 2085 | 21.1 | 0.59 |
| 14 | 23.64 | 3.76 | 271 | 57 | 16.1 | 2134 | 21.6 | 0.64 |
| 15 | 25.37 | 3.51 | 217 | 57 | 16.1 | 1191 | 12.1 | 0.36 |
| 16 | 25.47 | 3.49 | 219 | 73 | 20.7 | 1171 | 11.9 | 0.27 |
| 17 | 26.24 | 3.39 | 216 | 58 | 16.4 | 524 | 5.3 | 0.15 |
| 18 | 35.26 | 2.54 | 121 | 53 | 15 | 884 | 9 | 0.28 |
| 19 | 38.81 | 2.32 | 115 | 41 | 11.6 | 552 | 5.6 | 0.23 |
| 20 | 47.07 | 1.93 | 87 | 37 | 10.5 | 628 | 6.4 | 0.29 |

Example 24. C003 Tris-Salt Form 6

About 100 mg of 003-Tris-salt was dissolved completely in ethanol to form saturated solution at 60° C. (filtration if turbid). After that, cool the solution to room temperature slowly. If no enough amount of solid precipitated out at room temperature, the sample was put into −20° C. refrigerator or 4° C. refrigerator for crystallization. The solid was isolated by centrifugation and dried at 40° C. under vacuum condition overnight. Its XRPD data are provided below in Table 24.

TABLE 24

XRPD 2-theta of C003 tris-salt Form 6

| NO. | 2-Theta | d(A) | BG | Height | I % | Area | I % | FWHM |
|---|---|---|---|---|---|---|---|---|
| 1 | 6.51 | 13.56 | 73 | 43 | 13.8 | 260 | 2.8 | 0.10 |
| 2 | 8.14 | 10.86 | 75 | 41 | 13.1 | 657 | 7.1 | 0.27 |
| 3 | 9.34 | 9.46 | 74 | 258 | 82.7 | 8797 | 95.6 | 0.58 |
| 4 | 9.74 | 9.07 | 72 | 312 | 100 | 9201 | 100 | 0.50 |
| 5 | 11.48 | 7.70 | 72 | 144 | 46.2 | 2687 | 29.2 | 0.32 |
| 6 | 13.88 | 6.38 | 89 | 285 | 91.3 | 6561 | 71.3 | 0.39 |
| 7 | 16.22 | 5.46 | 115 | 77 | 24.7 | 2467 | 26.8 | 0.55 |
| 8 | 16.58 | 5.34 | 126 | 102 | 32.7 | 2426 | 26.4 | 0.40 |
| 9 | 18.02 | 4.92 | 182 | 282 | 90.4 | 8072 | 87.7 | 0.49 |
| 10 | 19.04 | 4.66 | 223 | 109 | 34.9 | 3760 | 40.9 | 0.59 |
| 11 | 19.16 | 4.63 | 228 | 116 | 37.2 | 3896 | 42.3 | 0.57 |
| 12 | 19.56 | 4.54 | 245 | 175 | 56.1 | 5361 | 58.3 | 0.52 |
| 13 | 20.42 | 4.35 | 254 | 92 | 29.5 | 1942 | 21.1 | 0.36 |
| 14 | 20.74 | 4.28 | 242 | 62 | 19.9 | 1201 | 13.1 | 0.33 |
| 15 | 22.62 | 3.93 | 182 | 112 | 35.9 | 2952 | 32.1 | 0.45 |
| 16 | 24.21 | 3.67 | 199 | 65 | 20.8 | 941 | 10.2 | 0.25 |
| 17 | 25.64 | 3.47 | 200 | 134 | 42.9 | 5287 | 57.5 | 0.67 |
| 18 | 25.96 | 3.43 | 206 | 146 | 46.8 | 4738 | 51.5 | 0.55 |
| 19 | 27.71 | 3.22 | 181 | 57 | 18.3 | 1643 | 17.9 | 0.49 |
| 20 | 27.91 | 3.19 | 181 | 71 | 22.8 | 1637 | 17.8 | 0.39 |
| 21 | 28.08 | 3.18 | 180 | 54 | 17.3 | 1658 | 18 | 0.52 |
| 22 | 29.08 | 3.07 | 171 | 53 | 17 | 735 | 8 | 0.24 |
| 23 | 33.55 | 2.67 | 122 | 44 | 14.1 | 786 | 8.5 | 0.30 |
| 24 | 36.28 | 2.47 | 126 | 44 | 14.1 | 1002 | 10.9 | 0.39 |
| 25 | 45.00 | 2.01 | 97 | 37 | 11.9 | 527 | 5.7 | 0.24 |

Example 25. C0003 Tris-Salt Form 7

Form 7 of C0003 tris-salt was prepared by heat-treated at 100° C. from Form 2 and its XRPD data are provided below in Table 25.

TABLE 25

XRPD 2-theta of C003 tris-salt Form 7

| NO. | 2-Theta | d(A) | BG | Height | I % | Area | I % | FWHM |
|---|---|---|---|---|---|---|---|---|
| 1 | 6.22 | 14.19 | 64 | 40 | 13.6 | 971 | 7.9 | 0.41 |
| 2 | 9.12 | 9.69 | 53 | 191 | 65 | 4626 | 37.5 | 0.41 |
| 3 | 10.64 | 8.31 | 58 | 56 | 19 | 583 | 4.7 | 0.18 |
| 4 | 12.28 | 7.20 | 67 | 37 | 12.6 | 904 | 7.3 | 0.42 |
| 5 | 12.48 | 7.09 | 70 | 58 | 19.7 | 904 | 7.3 | 0.27 |
| 6 | 13.54 | 6.53 | 78 | 50 | 17 | 546 | 4.4 | 0.19 |
| 7 | 15.20 | 5.82 | 87 | 203 | 69 | 6179 | 50.1 | 0.52 |
| 8 | 15.58 | 5.68 | 87 | 133 | 45.2 | 3152 | 25.6 | 0.40 |
| 9 | 17.50 | 4.87 | 147 | 79 | 26.9 | 935 | 7.6 | 0.20 |
| 10 | 18.75 | 4.71 | 169 | 67 | 22.8 | 405 | 3.3 | 0.10 |
| 11 | 20.00 | 4.41 | 223 | 191 | 65 | 8631 | 70 | 0.77 |
| 12 | 21.24 | 4.35 | 190 | 294 | 100 | 12334 | 100 | 0.71 |
| 13 | 22.49 | 3.99 | 171 | 99 | 33.7 | 2523 | 20.5 | 0.43 |
| 14 | 23.74 | 3.97 | 171 | 93 | 31.6 | 3135 | 25.4 | 0.57 |
| 15 | 24.99 | 3.92 | 179 | 139 | 47.3 | 4043 | 32.8 | 0.49 |
| 16 | 26.24 | 3.86 | 184 | 86 | 29.3 | 3793 | 30.8 | 0.75 |
| 17 | 24.20 | 3.67 | 163 | 65 | 22.1 | 475 | 3.9 | 0.12 |
| 18 | 25.52 | 3.49 | 147 | 89 | 30.3 | 2213 | 17.9 | 0.42 |
| 19 | 25.90 | 3.44 | 158 | 78 | 26.5 | 2197 | 17.8 | 0.48 |
| 20 | 27.56 | 3.23 | 161 | 51 | 17.3 | 991 | 8 | 0.33 |
| 21 | 29.00 | 3.08 | 138 | 44 | 15 | 368 | 3 | 0.14 |
| 22 | 30.40 | 2.94 | 128 | 50 | 17 | 821 | 6.7 | 0.28 |
| 23 | 32.22 | 2.78 | 111 | 47 | 16 | 266 | 2.2 | 0.10 |
| 24 | 45.31 | 2.00 | 83 | 37 | 12.6 | 898 | 7.3 | 0.41 |

Example 26. C0003 Tris-Salt Form 8

C0003 tris-salt Form 8 was prepared by heat-treated at 100° C. or 140° C. from Form 5. Its XRPD data are provided below in Table 26.

TABLE 26

XRPD 2-theta of C003 tris-salt Form 8

| NO. | 2-Theta | d(A) | BG | Height | I % | Area | I % | FWHM |
|---|---|---|---|---|---|---|---|---|
| 1 | 7.46 | 11.84 | 60 | 78 | 14.1 | 1908 | 10.6 | 0.42 |
| 2 | 7.88 | 11.21 | 61 | 53 | 9.5 | 1033 | 5.7 | 0.33 |
| 3 | 8.96 | 9.87 | 58 | 112 | 20.2 | 1538 | 8.5 | 0.23 |
| 4 | 10.14 | 8.72 | 57 | 79 | 14.2 | 991 | 5.5 | 0.21 |
| 5 | 11.18 | 7.91 | 56 | 52 | 9.4 | 534 | 3 | 0.18 |
| 6 | 14.00 | 6.32 | 93 | 199 | 35.9 | 4250 | 23.6 | 0.36 |
| 7 | 14.48 | 6.11 | 84 | 142 | 25.6 | 5427 | 30.1 | 0.65 |
| 8 | 14.84 | 5.96 | 111 | 145 | 26.1 | 2504 | 13.9 | 0.29 |
| 9 | 15.92 | 5.56 | 98 | 62 | 11.2 | 1232 | 6.8 | 0.34 |
| 10 | 16.50 | 5.37 | 105 | 201 | 36.2 | 4098 | 22.7 | 0.35 |
| 11 | 18.26 | 4.85 | 101 | 555 | 100 | 18018 | 100 | 0.55 |
| 12 | 18.62 | 4.76 | 173 | 291 | 52.4 | 11261 | 62.5 | 0.66 |
| 13 | 19.18 | 4.62 | 213 | 51 | 9.2 | 488 | 2.7 | 0.16 |
| 14 | 19.82 | 4.48 | 208 | 50 | 9 | 947 | 5.3 | 0.32 |
| 15 | 20.05 | 4.43 | 211 | 51 | 9.2 | 927 | 5.1 | 0.31 |
| 16 | 20.78 | 4.27 | 219 | 137 | 24.7 | 1458 | 8.1 | 0.18 |
| 17 | 21.76 | 4.08 | 196 | 140 | 25.2 | 2324 | 12.9 | 0.28 |
| 18 | 23.22 | 3.83 | 199 | 215 | 38.7 | 5855 | 32.5 | 0.46 |
| 19 | 24.14 | 3.68 | 197 | 49 | 8.8 | 428 | 2.4 | 0.15 |
| 20 | 25.49 | 3.49 | 164 | 70 | 12.6 | 2721 | 15.1 | 0.66 |
| 21 | 28.11 | 3.17 | 145 | 45 | 8.1 | 675 | 3.7 | 0.26 |
| 22 | 28.92 | 3.09 | 148 | 102 | 18.4 | 2251 | 12.5 | 0.38 |
| 23 | 31.02 | 2.88 | 117 | 41 | 7.4 | 341 | 1.9 | 0.14 |
| 24 | 32.39 | 2.76 | 104 | 50 | 9 | 862 | 4.8 | 0.29 |
| 25 | 32.54 | 2.75 | 107 | 37 | 6.7 | 674 | 3.7 | 0.31 |
| 26 | 37.98 | 2.37 | 93 | 55 | 9.9 | 1415 | 7.9 | 0.44 |
| 27 | 41.38 | 2.18 | 86 | 44 | 7.9 | 827 | 4.6 | 0.32 |
| 28 | 44.84 | 2.02 | 74 | 36 | 6.5 | 630 | 3.5 | 0.30 |
| 29 | 47.12 | 1.93 | 72 | 34 | 6.1 | 514 | 2.9 | 0.26 |

What is claimed is:

1. A pharmaceutically acceptable salt formed between tris (hydroxymethyl) aminomethane and 4-(1-{[2-Methyl-4-(4-trifluoromethyl-benzyl)-4H-thieno [3,2-b]pyrrole-3-carbonyl]amino}cyclopropyl) benzoic acid or 4-(1- {[4-(4-Trifluoromethyl-benzyl)-4H-thieno [3,2-b]pyrrole-3-carbonyl]-amino}-cyclopropyl)-benzoic acid.

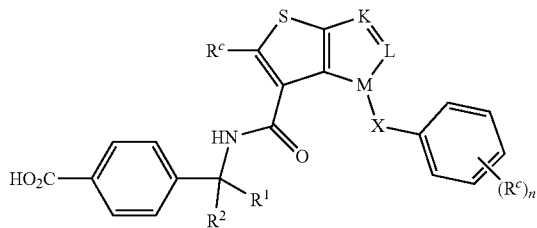

2. A pharmaceutical composition, comprising a pharmaceutically acceptable salt of claim 1 and a pharmaceutically acceptable carrier.

3. A method for treating cancer or an inflammatory disease, comprising administering to a subject in need thereof a pharmaceutically acceptable salt of claim 1.

4. The method of claim 3, wherein the cancer is breast cancer, endometrial cancer, cervix cancer, ovary cancer, lung cancer, head and neck cancer, brain cancer, thyroid cancer, oesophagus cancer, stomach cancer, colon & rectal cancer, liver cancer, pancreatic cancer, skin cancer, kidney cancer, bladder cancer, prostate cancer, testis cancer, bone cancer, Lymphoma, or blood cancer; and the inflammatory disease is arthritis, acne vulgaris, asthma, autoimmune diseases, autoinflammatory diseases, Celiac disease, chronic prostatitis, colitis, diverticulitis, glomerulonephritis, hidradenitis suppurativa, hypersensitivities, inflammatory bowel diseases, interstitial cystitis, Mast Cell Activation Syndrome, mastocytosis, otitis, pelvic inflammatory disease, reperfusion injury, rheumatic fever, rheumatoid arthritis, rhinitis, sarcoidosis, or vasculitis.

5. The method of claim 3 further comprising administering a second therapeutic agent or action selected from the group consisting of radiation, antibodies to cytotoxic t-lymphocyte antigen 4 (anti-CTLA4), antibodies to programmed death ligand 1 (anti-PDL1), antibodies to programmed cell death protein 1 (anti-PD1), and antimetabolites.

* * * * *